United States Patent
Altug et al.

(10) Patent No.: US 10,571,606 B2
(45) Date of Patent: Feb. 25, 2020

(54) NANOANTENNA ARRAYS FOR NANOSPECTROSCOPY, METHODS OF USE AND METHODS OF HIGH-THROUGHPUT NANOFABRICATION

(75) Inventors: Hatice Altug, Watertown, MA (US); Ahmet Ali Yanik, Brighton, MA (US); Shyamsunder Erramilli, Quincy, MA (US); Ronen Adato, Boston, MA (US); Serap Aksu, Allston, MA (US); Min Huang, Boston, MA (US); Alp Artar, Brighton, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 533 days.

(21) Appl. No.: 13/509,545

(22) PCT Filed: Oct. 22, 2010

(86) PCT No.: PCT/US2010/053757
§ 371 (c)(1),
(2), (4) Date: Jul. 25, 2012

(87) PCT Pub. No.: WO2011/050272
PCT Pub. Date: Apr. 28, 2011

(65) Prior Publication Data
US 2013/0148194 A1 Jun. 13, 2013

Related U.S. Application Data

(60) Provisional application No. 61/279,588, filed on Oct. 23, 2009, provisional application No. 61/352,654,
(Continued)

(51) Int. Cl.
*G02B 5/00* (2006.01)
*G01N 21/65* (2006.01)
(Continued)

(52) U.S. Cl.
CPC ........... *G02B 5/008* (2013.01); *G01N 21/554* (2013.01); *G01N 21/658* (2013.01); *B82Y 15/00* (2013.01);
(Continued)

(58) Field of Classification Search
CPC ........ G01J 3/02; G01J 3/44; G01J 5/02; H01J 3/26; H01J 9/142; G01N 23/00;
(Continued)

(56) References Cited

U.S. PATENT DOCUMENTS

| 5,912,095 | A | 6/1999 | Katakura |
| 2002/0027124 | A1* | 3/2002 | Bashir ..................... B82Y 5/00 216/11 |

(Continued)

FOREIGN PATENT DOCUMENTS

| WO | 2010/120531 A2 | 10/2010 |
| WO | 20100120531 A2 | 10/2010 |

(Continued)

OTHER PUBLICATIONS

Atkinson et al, Anisotropic optical properties of arrays of gold nanorods embedded in alumina, Phys. Rev. B, &3, 235402 (Jun. 5, 2006), pp. 1-8.*

(Continued)

*Primary Examiner* — Stephone B Allen
*Assistant Examiner* — Jyotsna V Dabbi
(74) *Attorney, Agent, or Firm* — Nixon Peabody, LLP

(57) ABSTRACT

The present invention generally relates to nanoantenna arrays and fabrication methods of said nanoantenna arrays. In particular, one aspect relates to nanoantenna arrays including nanostructures of predefined shapes in predefined patterns, which results in collective excitement of surface plasmons. The nanoantenna arrays can be used for spectroscopy and nanospectroscopy. Another aspects of the present
(Continued)

invention relate to a method of high-throughput fabrication of nanoantenna arrays includes fabricating a reusable nanostencil for nanostensil lithography (NSL) which provides a mask to deposit materials onto virtually any support, such as flexible and thin-film stretchable supports. The nanostencil lithography methods enable high quality, high-throughput fabrication of nanostructures on conducting, non-conducting and magnetic supports. The nanostencil can be prepared by etching nanoapertures of predefined patterns into a waffer or ceramic membrane. In some embodiments, a nanoantenna array includes plasmonic nanostructures or non-plasmonic nanostructures.

27 Claims, 39 Drawing Sheets

Related U.S. Application Data filed on Jun. 8, 2010, provisional application No. 61/367,246, filed on Jul. 23, 2010.

(51) Int. Cl.
*G01N 21/552* (2014.01)
*B82Y 20/00* (2011.01)
*B82Y 30/00* (2011.01)
*B82Y 15/00* (2011.01)

(52) U.S. Cl.
CPC ............... *B82Y 20/00* (2013.01); *B82Y 30/00* (2013.01); *Y10S 977/932* (2013.01)

(58) Field of Classification Search
CPC ........ G01N 21/658; G01N 21/553–554; G03F 9/00; G03F 2009/005; G02B 5/008; G02B 5/00; G02B 5/1809; G02B 1/105; G02B 5/201; B82Y 10/00; B82Y 15/00; B82Y 30/00; B82Y 20/00; Y10S 977/932
USPC .................................................. 359/350, 359
See application file for complete search history.

(56) References Cited

U.S. PATENT DOCUMENTS

| | | | |
|---|---|---|---|
| 2004/0174521 A1 | 9/2004 | Drachev et al. | |
| 2006/0175551 A1 | 8/2006 | Fan et al. | |
| 2006/0192115 A1 | 8/2006 | Thomas et al. | |
| 2008/0083881 A1 | 4/2008 | Gorrell et al. | |
| 2009/0299110 A1* | 12/2009 | Sarker | C10G 1/10 585/14 |
| 2009/0321261 A1* | 12/2009 | Vlahovic | B82Y 15/00 204/545 |
| 2011/0229706 A1* | 9/2011 | Epstein | B82Y 30/00 428/292.1 |

FOREIGN PATENT DOCUMENTS

| | | |
|---|---|---|
| WO | 2010/129319 A2 | 11/2010 |
| WO | 20100129319 A2 | 11/2010 |

OTHER PUBLICATIONS

Olcum et al, Tunable surface plasmon resonance on an elastomeric substrate (Optics Express vol. 17, No. 10, pp. 8542-8547, May 11, 2009).*
McAlpine et al (Highly ordered nanowire arrays on plastic substrates for ultrasensitive flexible chemical sensors, Nat. Mater., May 2007, 6(5):379-384).*
Merlein et al (Nanomechanical control of an optical antenna, Mar. 2, 2008, Nature Photonics, pp. 1-4 ).*
Yanik, et al., "Hybridized nanocavities as single-polarized plasmonic antennas" Opt. Express 17(23):20900 (2009).
Zou, et al., "Silver nanoparticle array structures that produce giant enhancements in electromagnetic fields" Chem. Phys. Lett. 403:62-67 (2005).
Zou, et al., "Silver nanoparticle array structures that produce remarkably narrow plasmon lineshapes" J. Chem. Phy. 120:10871-10875 (2004).
Zou, et al., "Theoretical studies of plasmon resonances in one-dimensional nanoparticle chains: narrow lineshapes with tunable widths" Nano Tech 17:2813-2820 (2006).
Adato, et al., "Ultra-sensitive vibrational spectroscopy of protein monolayers with plasmonic nanoantenna arrays" Proc. Nat. Acad. Sci. USA 106(46):19227-1932 (2009).
Alu, et al., "Tuning the scattering response of optical nanoantennas with nanocircuit loads" Nature Photonic 2:307-310 (2008).
Artar, et al., "Fabry-Pérot nanocavities in multilayered plasmonic crystals for enhanced biosensing" Appl. Phys. Lett. 95, 051105; doi: 10.1063/1.3202391 (2009).
Ataka, et al., "Biochemical applications of surface-enhanced infrared absorption spectroscopy" Analytical Bioanalytical Chemistry 388(1):47-54 (2007).
Auguie, et al., "Collective resonances in gold nanoparticle arrays" Phys Rev. Letts 101(14):143902 (2008).
Auguie, et al., "Diffractive coupling in gold nanoparticle arrays and the effect of disorder" Opt. Lett 34(4):401-3 (2009).
Bendana, et al., "Confined collective excitations of self-standing and supported planar periodic particle arrays" Opt. Express 17(21):18826-35 (2009).
Bukasov, et al., "Silver nanocrescents with infrared plasmonic properties as tunable substrates for surface enhanced infrared absorption spectroscopy" Anal. Chem. 81(11):4531-4535 (2009).
Chen, et al., "Surface-enhanced second-hariiionic generation and Raman scattering" Phys. Rev 27(4):1965-1979 (1983).
Crozier, et al., "Optical antennas: Resonators for local field enhancement" J. Applied Physics 94(7):4632-4642 (2003).
Cubukcu, et al., "Optical nanorod antennas as dispersive one-dimensional Fabry-Pérot resonators for surface plasmons" Appli. Phys. Lett. 95, 201101 (2009).
Datta, "Electrical resistance: an atomistic view" Nanotech 15:S433-S451 (2004).
Della Valle, et al., "Efficient suppression of radiation damping in resonant retardation-based plasmonic structures" Phys. Rev. B 79 113410 (2009).
Klar, et al., "Surface-Plasmon Resonances in Single Metallic Nanoparticles" Phys. Rev. Lett. 80(19):4249-4252 (1998).
Enders, et al., "Surface enhanced infrared absorption of octadecanethiol on wet-chemically prepared Au nanoparticle films" Appl. Phys. Lett. 88, 184104 (2006).
Ferry, et al., "Plasmonic Nanostructure Design for Efficient Light Coupling into Solar Cells" Nano Lett 8 (12):4391-4397 (2008).
Frey, et al., "High-Resolution Imaging of Single Fluorescent Molecules with the Optical Near-Field of a Metal Tip" Phys. Rev. Lett 93(20): 2008012-2008014 (2004).
Genet, et al., "Light in tiny holes" Nature 445(4):39-46 (2007).
Homola, et al., "Surface plasmon resonance sensors: review" Sens. Actuators B 53, pp. 3-15 (1999).
Jensen, et al., "Surface-Enhanced Infrared Spectroscopy: A Comparison of Metal Island Films with Discrete and Nondiscrete Surface Plasmons" Appl. Spectroscopy 54:371-377 (2000).
Jensen, et al., "Electrodynamics of Noble Metal Nanoparticles and Nanoparticle Clusters" Journal of Cluster Science, 10(2):296-317 (1999).
Kneipp, et al., "Single Molecule Detection Using Surface-Enhanced Raman Scattering (SERS)" Phys. Rev. Letts 78(9):1667-1670 (1997).
Kravets, et al., "Extremely Narrow Plasmon Resonances Based on Diffraction Coupling of Localized Plasmons in Arrays of Metallic Nanoparticles" Phys. Rev. Lett 101PRL 101, 087403 (2008).
Kundu, et al., "Surface enhanced infrared absorption (SEIRA) spectroscopy on nanoshell aggregate substrates" Chem. Phys. Lett. 452:115-119 (2008).
Lal, et al., "Nano-optics from sensing to waveguiding" Nat. Photonics 1:641-648 (2007).

(56) References Cited

OTHER PUBLICATIONS

Lamprecht, et al., "Metal Nanoparticle Gratings: Influence of Dipolar Particle Interaction on the Plasmon Resonance" Phys. Rev. Lett 84(20):4721-4724 (2000).
Lawrence, et al., "Processing methods to control silk fibroin film biomaterial features" J. Mater. Sci 43:6967-6985 (2008).
Lee et al., "Gold and Silver Nanoparticles in Sensing and Imaging: Sensitivity of Plasmon Response to Size, Shape, and Metal Composition" J. Phys. Chem. B 110:19220-19225 (2006).
Markel, et al., "Divergence of dipole sums and the nature of non-Lorentzian exponentially narrow resonances in one-dimensional periodic arrays of nanospheres" J. Phys. B: At. Mol. Opt. Phys. 38:L115-L121 (2005).
Meier, et al., "Enhanced fields on rough surfaces: dipolar interactions among particles of sizes exceeding the Rayleigh limit" J. Optical Society of America 2(6):931-949 (1985).
Meier, et al., "Enhanced fields on large metal particles: dynamic depolarization" Opt. Lett 8(11):581-583 (1983).
Neubrech, et al., "Resonant Plasmonic and Vibrational Coupling in a Tailored Nanoantenna for Infrared Detection." Phys. Rev. Lett. PRL 101, 157403 (2008).
Novotny, "Effective Wavelength Scaling for Optical Antennas" Phys. Rev. Lett. PRL 98 266802 (2007).
Omenetto, et al., "A new route for silk" Nature Photonics 2:641-643 (2008).
Osawa, et al., "Surface-Enhanced Infrared Absorption of p-Nltrobenzolc Acid Deposited on Silver Island Films: Contributions of Electromagnetic and Chemical Mechanisms" J. Phys. Chem. 95:9914-9919 (1991).
Ozbay, "Plasmonics: Merging Photonics and Electronics at Nanoscale Dimensions" Science 311:189-193 (2006).
Rakic, et al., "Optical properties of metallic films for vertical-cavity optoelectronic devices" Appl. Opt. 37(22):5271-5283 (1998).
Sanchez, et al., "Near-Field Fluorescence Microscopy Based on Two-Photon Excitation with Metal Tips" Phys. Rev. Lett. 82(20):4014-4017 (1999).
Sashina, et al., "Structure and Solubility of Natural Silk Fibroin" Russian J. Appl. Chem. 79(6);869-876 (2006).
Schnell, et al., "Controlling the near-field oscillations of loaded plasmonic nanoantennas" Nature Photonics 3:287-291 (2009).
Sonnichsen, et al., "Drastic Reduction of Plasmon Damping in Gold Nanorods" Phys. Rev. Lett. 88(7):077402 (2002).
Stockman, et al.,"Enhanced Raman scattering by fractal clusters: Scale-invariant theory" Phys. Rev. B 46(5):2821 (1992).
Tolstoy, et al., "3.10. Determination of optical constants of isotropic ultrathin films: Experimental errors in reflectivity measurements" Handnook of Infrared Spectroscopy of Ultrathin Films (John Wiley & Sons Inc, Hoboken, NJ) pp. 243-286 (2003).
Urzhumov et al., "Applications of Nanoparticle Arrays to Coherent Anti-Stokes Raman Spectroscopy of Chiral Molecules" Proc. SPIE, 5927 59271D (2005).
Wang et al., "General Properties of Local Plasmons in Metal Nanostructures" Phys. Rev. Lett PRL 97, 206806 (2006).
Warwicker, "The Crystal Structure of Silk Fibroin" Acta Crystal 7:565-573 (1954).
White et al., "On the performance quantification of resonant refractive index sensors" Opt. Express 16:1020-1028 (2008).
Williams, et al., "Accessing Surface Plasmons with Ni Microarrays for Enhanced IR Absorption by Monolayers" J. Phys. Chem B . 107:11871-11879 (2003).
Yanik, et al., "Quantum transport with spin dephasing: A nonequlibrium Green's function approach" Phys. Rev. B 76:045213 (2007).
Yanik, et al., "Extraordinary midinfrared transmission of rectangular coaxial nanoaperture arrays" Appl. Phys. Lett. 93:081104 (2008).
Cass. S., Technology Review, Nov. 8, 2010 "A Bendable, light bending material." (available at http://www.technologyreview.com/printer_friendly_article.aspx?id=26684).
Di Falco, et al., "Flexible metamaterials at visible wavelengths" New Journal of Physics, 2010,12: 113006 (first published Nov. 4. 2010).
Huang, el al., "Actively tuned plasmons on Elastometically Driven Au Nanoparticle dimers" NANO letters, 2010, 10; 1787-1792 (published online on Apr. 21, 2010.
Pryce, et al., "Highly Strained Compliant Optical metamaterials with large Frequency Tunability" NANO letters, 2010, 10; 4222-4227. (Published online on Sep. 21, 2010).
Cass, "A Bendable, Light-Bending Material" Technology Review, Published by MIT, Nov. 8, 2010.
Difalco et al., "Flexible metamaterials at visible wavelengths" New Journal of Physics 12:1-7 (2010).
Huang et al., "Actively Tuned Plasmons on Elastomerically Driven Au Nanoparticle Dimers" Nano Lett. 10:1787-1792 (2010).
Price et al., "Highly Strained Compliant Optical Metamaterials with Large Frequency Tunability" Nano Lett. 10: 4222-4227 (2010).

\* cited by examiner

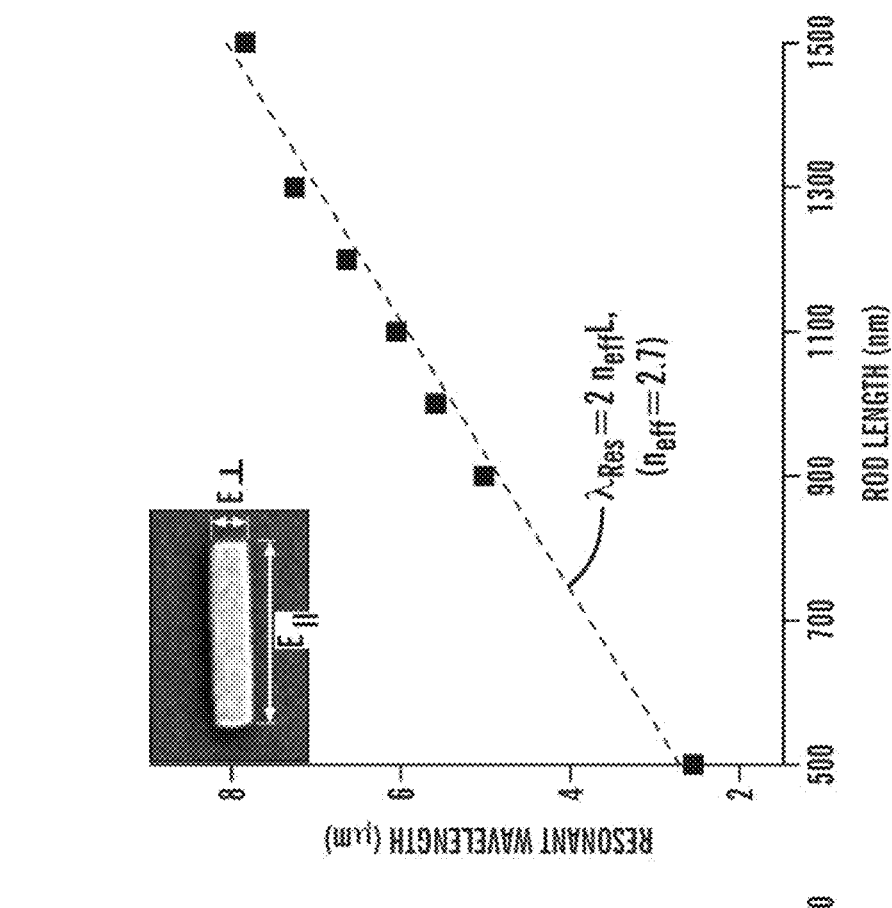
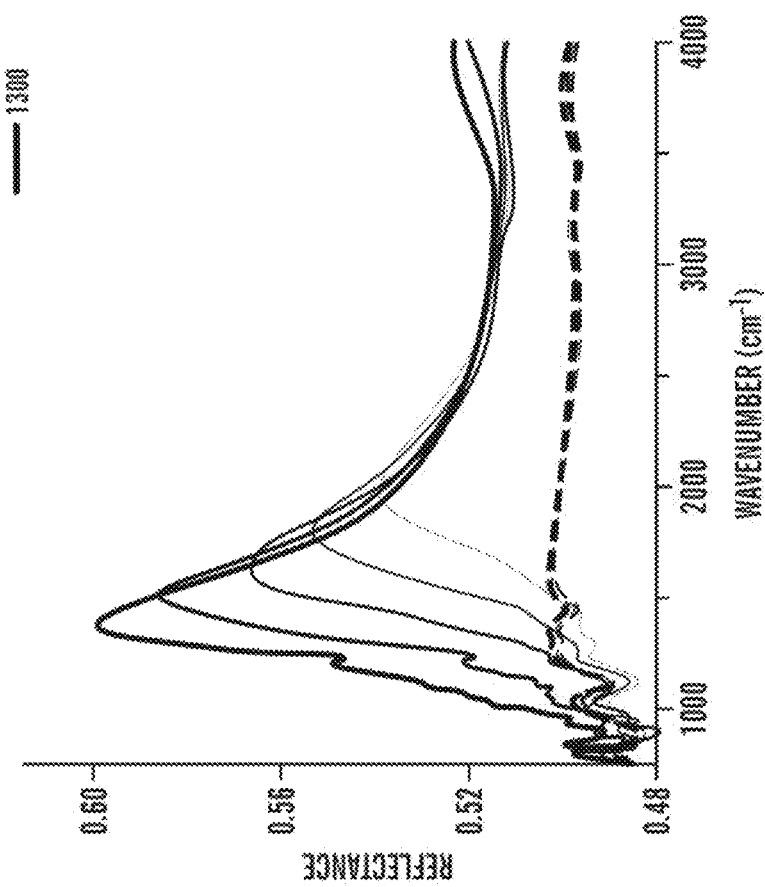
FIG. 1B
FIG. 1A

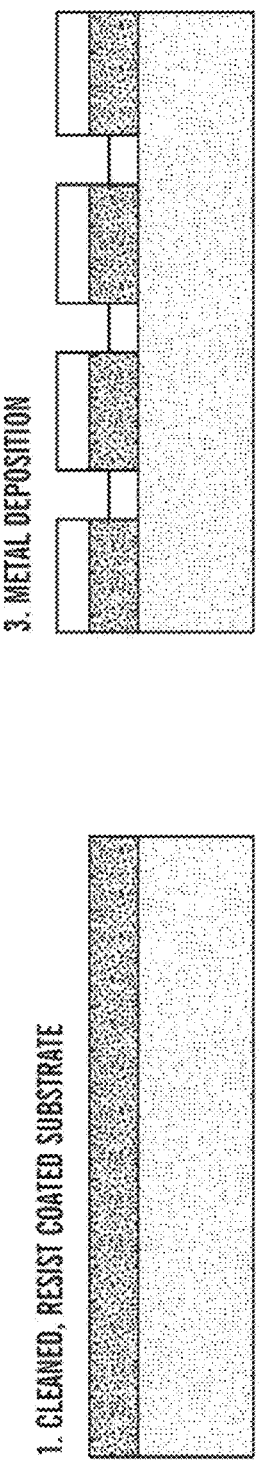
FIG. 8C
FIG. 8A
FIG. 8D
FIG. 8B

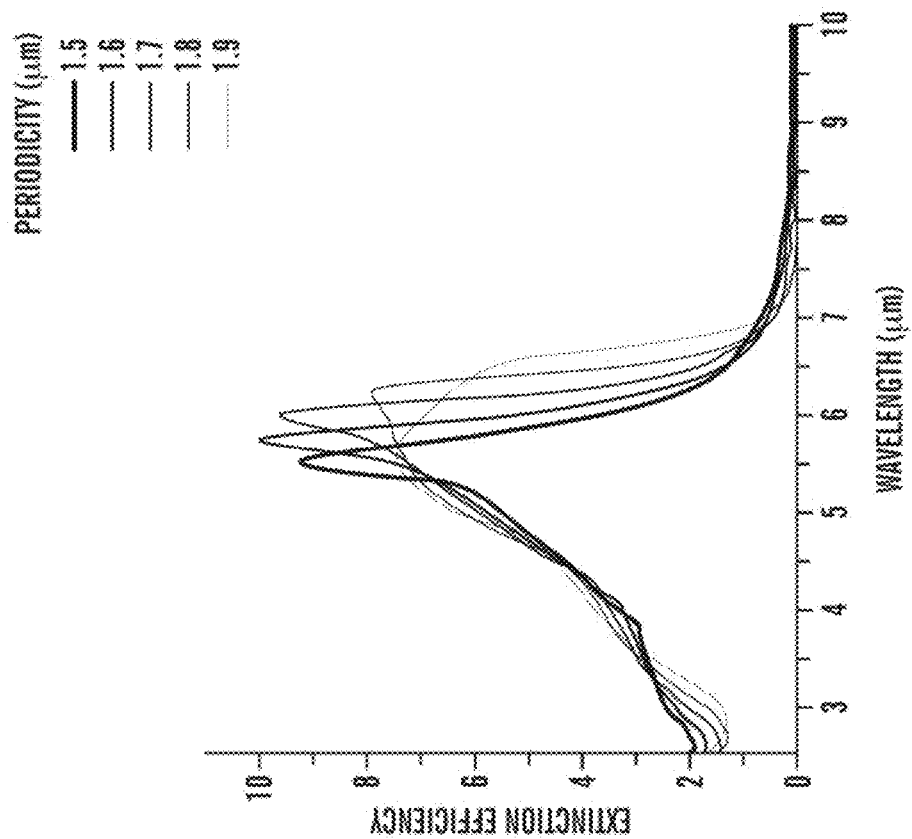
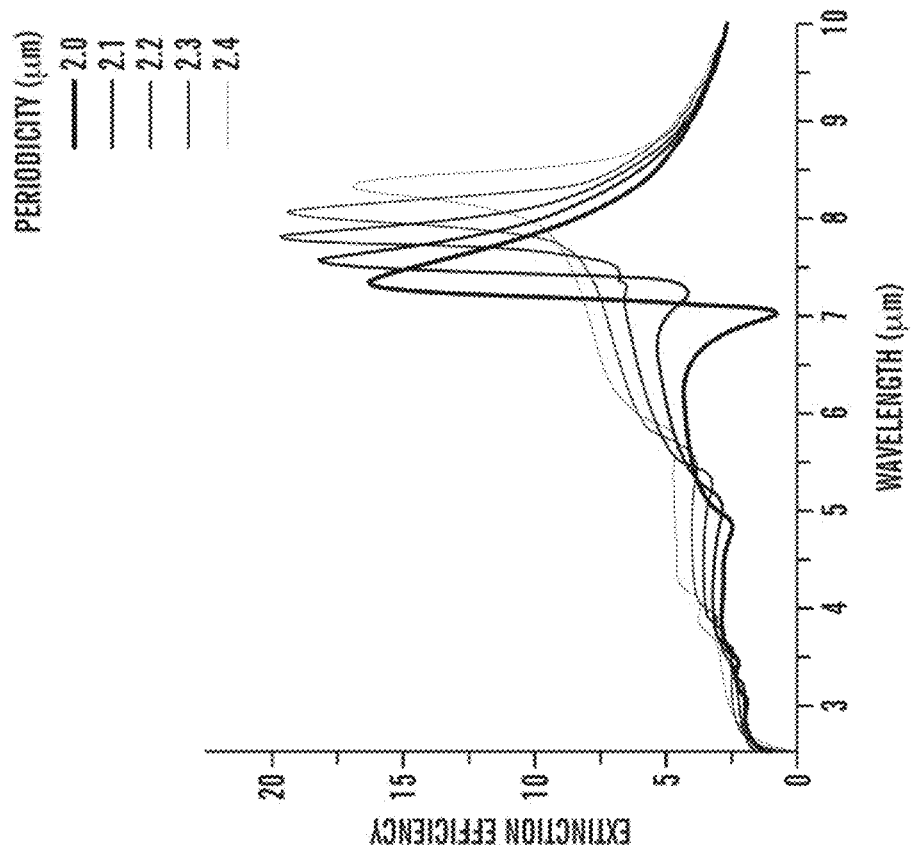
FIG. 15B
FIG. 15A

NANOANTENNA ARRAYS FOR NANOSPECTROSCOPY, METHODS OF USE AND METHODS OF HIGH-THROUGHPUT NANOFABRICATION

CROSS REFERENCE TO RELATED APPLICATION

This application is a 35 U.S.C. § 371 National Phase Entry Application of International Application No. PCT/US2010/053757 filed Oct. 22, 2010, which designates the U.S., and which claims benefit under 35 U.S.C. § 119(e) of U.S. Provisional Patent Application Ser. No. 61/279,588 filed on Oct. 23, 2009 and U.S. Provisional Patent Application Ser. No. 61/352,654 filed on 8 Jun. 2010 and U.S. Provisional Patent Application Ser. No. 61/367,246, filed on 23 Jul. 2010, the content of which are incorporated herein by reference in their entirety.

GOVERNMENT SUPPORT

This invention was made with Government Support under Contract Nos. ECCS-0849603, ECCS-0954790 and EEC-0812056 awarded by the National Science Foundation and Contract No. N0001410-1-0742 awarded by the Office of Naval Research. The Government has certain rights in the invention.

FIELD OF THE INVENTION

The present invention is directed to nanoantenna arrays, such as plasmonic nanoantenna arrays and fabrication of nanoantenna arrays. More specifically, the invention provides a nanoantenna arrays comprising plasmonic nanostructures, and method of use and fabrication. Another aspect of the present invention relates to a high-throughput, nanofabrication process for producing complex nanostructures on virtually any support using nanostencil lithography, for example, for fabrication of plasmonic nanoantenna antenna arrays and nanoantenna arrays comprising non-plasmonic nanostructures.

BACKGROUND OF THE INVENTION

Nanoplasmonics relates to optical studies of tailored metallic nanostructures and their applications, and has emerged as a growing field in recent years. Nanoplasmonics allows for sub-wavelength light localization and dramatically strong local fields. Plasmons have been used to enhance linear and non-linear optical phenomena including fluorescence, surface enhanced Raman spectroscopy, and high-order harmonic generation. Proof of concept devices such as plasmon lasers, super-lenses, and metamaterials have been demonstrated.

A new generation of antennas operating at the optical and infrared frequencies is emerging from the well developed concepts in microwave antenna theory. Plasmonic nanoantennas, with their unique ability of focusing light beyond the diffraction limit, are at the core of a myriad of new exciting opportunities in photonics (Lal et al., (2007), Nat. Photonics 1:641-648; Genet C et al., (2007), Nature 455:39-46; Artar et al., (2009)). By exploiting extremely strong and localized fields in the visible wavelength range, signal enhancements of several orders of magnitude have been demonstrated in second harmonic generation (Chen et al., (1983) Phys. Rev. B 27:1965-1979.4), fluorescence (Genet C et al., (2007), Nature 455:39-46, Frey et al., (2004), Phys. Rev. Letts 93:2008015) and surface enhanced Raman scattering (SERS) (Lal et al., (2007), Nat. Photonics 1:641-648; Genet C et al., (2007), Nature 455:39-46, Kneipp et al., (1997), Phys. Rev. Letts 78:1667-1670).

The plasmonic enhancement of optical near-fields can also be extended to the infrared frequencies enabling dramatic signal enhancement in infrared (IR) spectroscopy. In analogy to SERS, this method is called surface enhanced infrared absorption (SEIRA) spectroscopy (Osawa et al., (1991) J. Physical Chemistry. 95:9914-9919; Jensen et al., (2000). Applied Spectroscopy 54:371-377; Williams et al., (2003) J. Phys. Chem. B 107:11871-11879; Enders et al., (2006) Applied Physics Letters 88:184104; Kundu et al., (2008) Chemical Physics Letters. 452:115-119; Neubrech et al., (2008) Physical Review Letters 101:157403; Bukasov et al., (2009). Analytical Chemistry 81:4531-4535; Ataka et al., (2007) Analytical Bioanalytical Chemistry 308:47-54.). Until recently, the bulk of SEIRA studies have revolved around enhancements achieved via chemically prepared or roughened metal surfaces. In these supports, however, signal enhancement factors have been limited to 10-100 range due to their random nature (Ataka et al., (2007) Analytical Bioanalytical Chemistry 308:47-54). Uncontrolled surface geometries also cause poor spectral overlap between plasmonic resonances and the molecular vibrational modes of interest. These limitations result in weaker absorption signals preventing reproducible vibrational measurements from protein monolayer films.

Additionally, advances in nanoplasmonics are critically dependent on the ability to structure metals in a controllable way at sub-100 nm resolution. The most common top-down nanopatterning techniques with high resolution are electron beam and focused ion beam lithography. Electron beam lithography (EBL) is mostly used for on-chip plasmonic nanoparticle array fabrication, while focused ion beam (FIB) tools are reserved primarily to fabricate nanoapertures in metallic films. Both EBL and FIB can offer flexibility in creating a variety of nanostructure geometries and patterns at high resolution. However, their major drawback is the low-throughput. Due to their serial nature, each nanostructure has to be created one at a time, which is both slow and expensive. In addition, for EBL, the choice of supports is also limited due to the dependence of the e-beam exposure on the support conductivity. For example, patterning on glass supports could be done by adding a conductive film (such as ITO). But, this conductive layer can interfere with the optical responses of the fabricated nanostructures. Plasmonic nanoparticle and nanowire fabrication with EBL often involves a lift-off process, which can be restrictive in creating nanostructures with high aspect ratios. While multilayer lithographic processes can be used to create nanostructures with high aspect ratios, they are cumbersome due to the involvement of multiple fabrication steps.

SUMMARY OF THE INVENTION

The present invention is generally directed to plasmonic nanoantenna arrays and methods of their high-throughput fabrication. The nanoantenna arrays and high-throughput processes and techniques as described herein, support collective plasmon resonances which lead to spectrally narrow far-field extinction resonances and strong near-field enhancements, and are extremely important for surface enhanced spectroscopy methods.

One aspect of the present invention relates to nanoantenna arrays comprising a plurality of nanostructures arranged in a predefined pattern for collective excitement of surface plasmons. Another aspect of the present invention described herein relates in part, to nanostencils and methods of fabricating complex plasmonic nanoantenna arrays, for example nanoantenna arrays comprising plasmonic or non-plasmonic nanostructures. By enabling optical and electrical signal transmission through the same metal circuitry, nanoplasmonics using the devices and methods described herein can lead to large scale on-chip integration of electronic and photonic components with high-fidelity.

Without wishing to be limited to theory, infrared absorption spectroscopy enables direct access to vibrational fingerprints of the molecular structure, and is a powerful method for functional studies of bio-molecules. While the intrinsic absorption cross-sections of infra-red (IR) active modes of proteins are nearly 10 orders of magnitude larger than the corresponding Raman cross-sections, they are still small compared to that of fluorescence-label based methods.

Herein, the inventors have fabricated a nanoantenna array as a tool for collective excitation of plasmonic resonances, and have demonstrated direct detection of vibrational signatures of single protein monolayers. The nanoantenna arrays have been tailored with specific predefined patterns and predefined shapes of a plurality of individual nanostructures (e.g. nanoantennas, also referred herein as "plasmonic nanostructures") to form resonant structures that match the molecular vibrational modes. The inventors surprisingly discovered that when the nanoantennas (or plasmonic nanostructures) are specifically configured to be arranged in specific predefined geometric shape and predefined patterns and spatial configurations (as opposed to a random configuration), that their in-phase dipolar coupling leads to a collective excitation of the ensemble with strongly enhanced near-fields. Additionally the inventors surprisingly discovered that the combined collective and individual plasmonic responses of the predefined shapes of the nanoantennas, arranged in a predefined pattern on the array play a critical role in attaining signal enhancement factors of $10^4$-$10^5$. The inventors also demonstrate efficient measurement of the vibrational spectra of proteins at zepto-mole levels for the entire nanoantenna array, corresponding to only 145 molecules per antenna, demonstrating the nanoantenna arrays as disclosed herein are useful for nanospectroscopy (e.g., spectroscopy using a small number or molecules). The near-field nature of the plasmonic enhancement of the absorption signals is also demonstrated herein with progressive loading of the nanoantennas (or plasmonic nanostructures) with varying protein film thicknesses. Finally, the inventors use an advanced model based on Non-Equilibrium Greens Function formalism to demonstrate the observed Fano-type absorption line-shapes and to tailor the use of the nanoantenna array for specific tuning for different absorption strengths with the antenna resonance.

Thus, the inventors have demonstrate herein that nanostructures, e.g., plasmonic nanostructures of a predefined shape and a pre-defined pattern results in a collective resonant excitation. Accordingly, in the nanoantenna arrays as disclosed herein comprise nanoantennas (or plasmonic nanostructures) which have predefined shapes and are organized on the nanoantenna array in a predefined pattern (as opposed to configured at random), to result in radiative dipolar coupling and the interference of the multiple scattering from antennas in the array can be utilized for the spectral narrowing of the far field response. These collective resonances are linked to the strongly enhanced near-field intensities, and can be used for a much stronger or enhanced coupling between the incident field and the transition dipole moments of the proteins as compared to the individual nanoantennas, randomly organized nanoantennas or chemically prepared supports.

Accordingly, the present invention relates to a method of use of the nanoantenna arrays for an ultra-sensitive collectively enhanced IR absorption (CEIRA) spectroscopy technique, allowing direct identification of vibrational signatures of single proteins and protein monolayers, for example, silk fibroin. Measurement of vibrational signatures with zepto-mole level protein detection limits are achieved due to the $10^4$-$10^5$ signal enhancements, demonstrating the use of the nanoantenna arrays for nanospectroscopy. Absorption signals for the nanostructures on the nanoantenna arrays as disclosed herein are demonstrated herein with high reliability and reproducibility and far surpass those of the individual nanostructures by themselves.

Additionally, the inventors have also surprisingly discovered that significantly longer plasmon lifetimes and stronger near-field enhancements can be achieved by embedding the plasmonic nanostructures, such as nanoantennas into the support of the nanoantenna array. The inventors demonstrated that embedding the plasmonic nanostructures, such as the nanoantennas are in the same plane, or below the surface of the support (e.g., depressed or in a recess) results in a more homogeneous dielectric background, allowing stronger diffractive couplings among plasmonic particles leading to strong suppression of the radiative damping. Using embedded plasmonic nanostructures results in near-field enhancements well beyond than those achievable with isolated nanoparticles. Such nanoantenna arrays, including those with raised (e.g., on-surface), or embedded plasmonic nanostructures enhances electromagnetic fields obtained in these structures and are useful for biosensing and non-linear photonics applications.

Accordingly, one aspect of the present invention is directed to plasmonic nanoantenna arrays as described herein.

Another aspect of the present invention is directed to methods and processes for high-throughput fabrication of nanoantenna arrays, including nanoantenna arrays comprising plasmonic nanostructures and nanoantenna arrays comprising non-plasmonic nanostructures. In some embodiments, the methods and processes for high-throughput fabrication of nanoantenna arrays involves nanostencil lithography (NSL) fabrication methods, enabling nanostructures (of plasmonic or non-plasmonic materials) of predefined shapes to be arranged in predefined patterns, e.g., in organized, or a periodic array configuration. In some embodiments, the nanostencil lithography (NSL) fabrication methods as disclosed herein enable plasmonic nanostructures to be arranged in a predefined pattern, e.g., a periodic pattern, for example, for an infrared plasmonic nanorod antenna array. In some embodiments, the plasmonic nanoantenna arrays are fabricated using novel nanostencil lithography according to the methods and devices described herein.

One aspect of the present invention relates to nanoantenna arrays comprising a support and a plurality of plasmonic nanostructures arranged in a predefined pattern, e.g., a periodic pattern for collective excitation of plasmons and increased plasmon resonance. In some embodiments, a plasmonic nanostructure is present on the surface of the support of the array, e.g., a nanostructure raised above or on the surface of the array support. In alternative embodiments, a plasmonic nanostructure is below (e.g., depressed), or at the same level (e.g. in the same plane) as the surface of the support of the array. Such an embodiment where the plasmonic nanostructure is below (e.g. depressed), or at the same plane as the surface of the support, is referred to herein as a "embedded plasmonic nanostructure". In some embodiments, where the plasmonic nanostructure is embedded below (e.g., depressed) the surface of the surface of the support of the array, there is a void above the embedded plasmonic nanostructure. In alternative embodiments, this void can be optionally filled with a non-wavelength refracting or wavelength permeable material. Accordingly, in some embodiments, where the plasmonic nanostructure is embedded, the void above the plasmonic nanostructure can be filled with a material which is permeable to an incident wavelength.

In some embodiments, a plasmonic nanostructure, whether raised or embedded, comprises plasmonic material, for example, a metallic material, for example, selected from gold, silver, nickel, copper, platinum, as well as other metallic materials as disclosed herein.

One aspect of the present invention relates to a nanoantenna array device comprising; (a.) a support; (b) a plurality of plasmonic nanostructures where the plasmonic nanostructures has a controlled shape (e.g., it does not have particle scattering surrounding the nanostructure), and wherein the plurality of plasmonic nanostructures have a predefined shape in a predefined pattern with respect to the support, and wherein the predefined pattern is a function of the collective excitation of plasmons and localized plasmon resonance. In some embodiments, the nanoantenna array can comprise nanostructures that are raised on the surface of the support, or embedded at or below the surface of the support, and can be, for example, depressed or present in a recess in the support, or can comprise any combination of raised or embedded nanostructures. In some embodiments, a plurality of plasmonic nanostructures embedded below the surface of the support is layered with a material that can be penetrated by an incident wavelength of electromagnetic radiation. In some embodiments, the predefined pattern is selected from a combination of a periodic pattern, a non-periodic pattern, a uniform pattern, a lattice, a super-periodic pattern. In some embodiments, the pattern is not a random pattern.

In some embodiments, the support of the nanoantenna array can be selected from a non-conductive layer, and can comprise silicon, and in some embodiments, the support is selected from the group consisting of: silicon, silicon dioxide, silicon nitride, MgF2, calcium fluoride (CaF2), a polymer, glass, diamond, ZnSe, Germanium, GaAs, quartz or a quartz based microscope slide.

In some embodiments, a predefined shape of a nanostructure can be selected from the group consisting of: nanorod, nanorectangle, nanosquare, nanodisc, nanocircle, nano-oval, nanotriangle, cross-shaped, nanowires, or irregular shaped. In some embodiments, nanostructures, or collections of nanostructures can be in patterns separated by a periodicity of between 100-10,000 nm, or separated by a periodicity of between 100-1000 nm.

In some embodiments, a nanoantenna arrays comprises an adhesive layer, wherein the adhesive layer is between the support and the plurality of plasmonic nanostructures, for example, comprising titanium or chromium or a combination thereof. In some embodiments, an adhesive layer is at least 50 nm in thickness, or less than 50 nm thick, or less than 25 nm thick, or less than 15 nm thick.

In some embodiments, a plasmonic nanostructure can comprise at least one plasmonic material, for example, at least two or more different plasmonic materials. In some embodiments, a plasmonic material is a metallic material, for example, selected from a Noble Metal, a transition metal or an alkali metal. In some embodiments, a plasmonic nanostructure can also comprise a non-plasmonic material. In some embodiments, a metallic material is selected from the group consisting of: gold (Au), Silver (Ag), rhodium, palladium, osmium, iridium, platinum (Pt), titanium (Ti) and Aluminum (Al), Palladium (Pd), or any combination thereof. In some embodiments, a metallic material is a Noble metal, which is selected from the group consisting of: gold (Au), Silver (Ag), rhodium, palladium, osmium, iridium and platinum (Pt). In some embodiments, a plasmonic material is selected from the group consisting of: gold (Au), Silver (Ag), platinum (Pt), Copper (Cu), Aluminum (Al), Palladium (Pd), iron, vanadium, molybdenum or alloys thereof, or any combination thereof.

In some embodiments, a plasmonic nanostructures is in a collection with one or more other nanostructures, e.g., in a collection or coupled to one or more other plasmonic nanostructures, where the collection is then organized into the predefined pattern on the support for collective resonance. In some embodiments, coupled plasmonic nanostructures comprises at least two or more nanorods in a parallel configuration. In some embodiments, a collection of nanostructures can comprise the same or a different size, shape and/or dimension of nanostructures. In some embodiments, coupled plasmonic nanostructures comprises two or more nanorods in a series configuration or in a dimer configuration. In some embodiments, coupled plasmonic nanostructures comprises two or more nanotriangles. In some embodiments, coupled plasmonic nanostructures comprises two or more nanotriangles in a bow-tie or dimer configuration. In some embodiments, coupled plasmonic nanostructures comprises two or more plasmonic nanostructures in a symmetrical configuration, for example but not limited to, a plurality of nanotriangles in a star or cross configuration.

In some embodiments, a plasmonic nanostructure can comprise a plurality of layers of two or more different plasmonic materials.

In some embodiments, the plasmonic nanostructures are arranged in a predefined pattern as a function of their localized plasmon resonance. For example, the plasmonic nanostructures are configured with respect to the surface of the support in a uniform configuration such that the collective resonances modify the quality factor or near-field enhancement properties of the resonance. In some embodiments, at least one of the nanoparticles forms a unit cell, and at least two unit cells are arranged in a pattern on the nanoantenna array to form a lattice, wherein light propagating from one unit cells to the next unit cell throughout the array results in a collective resonance on the nanoantenna array that differs from each unit cell's resonance in more than just an additive summing of each unit cell's resonance, wherein the unit cell's resonance results from light propagating from one unit cell to the next unit cell and wherein the light undergoes a fill integer multiple of $2\pi$ phase shift, and wherein the light forms a diffraction order that is evanescent, it does not propagate into the far-field, at wavelengths longer than the corresponding lattice mode and also radiative, it does not propagate into the far-field at wavelengths shorter than the corresponding lattice mode.

In some embodiments, the nanoantenna array comprises plasmonic nanostructures configured with respect to the surface of the support in a uniform configuration such that an acting electric field ($E_{acting,i}$) on a single neoplasmonic structure is the sum of the incident electric field ($E_{incident,i}$) and the sum of a retarded dipolar field due to the other neoplasmonic structures in the nanoantenna array, and is characterized by the formula:

$$\vec{E}_{acting,i} = \vec{E}_{incident,i} + \sum_{i \neq j} \vec{E}_{retarded,ij} = \vec{E}_0 e^{i\vec{k}\cdot\vec{r}_i} + \sum_{i \neq j} (\overleftrightarrow{c}_{ij} \cdot \vec{P}_j) e^{ikr_{ij}}$$

$E_0$ is the incident field, Pj is the induced polarization of j-th neoplasmonic structures in the array, and $c_{ij}$ is the dipolar interaction matrix among the plurality of neoplasmonic without the phase term.

In some embodiments, the predefined pattern of the plurality of plasmonic nanostructures on the nanoantenna array is in a lattice, and wherein the lattice is selected from the group of: a triangular lattice, a square lattice, a rectangular lattice, an octagonal lattice, a hexagonal lattice, and other lattices or combination of lattices. In some embodiments, a predefined pattern of the plurality of plasmonic nanostructures on the array is not in a lattice or in a non-periodic pattern with respect to each other.

In some embodiments, a nanoantenna array comprises a support which has a substantially planar surface, and in some embodiments, the support can include a thin membrane, or a thin film, or a thin membrane carrier support, or a solid support. In some embodiments, the support does not comprise a thin conductive film on the surface of the support. In some embodiments, a thin conductive film support is selected from the group of: a thin ITO layer, a thin sacrificial metal layer, a flexible substrate, a grapheme layer, a conducting polymer layer, or combinations thereof.

Another aspect of the present invention relates to the use of the nanoantenna array as disclosed herein with visible wavelength, or with mid-IR wavelength.

Another aspect of the present invention relates to the use of the nanoantenna array in spectrometry, for example, nanospectroscopy, for example with very small number of molecules (for example, for measurement of zepto-mole level of molecules, for example as demonstrated herein in the examples of protein detection by measuring the vibrational signatures zepto-mole level of proteins, where the nanoantenna array enabled a $10^4$-$10^5$ signal enhancement). In some embodiments, nanospectroscopy can be used for bioanalyte detection, chemical detection, toxin detection, gas detection, for example, where the bioanalyte is selected from the group consisting of: a protein, a small molecule compound, a metabolite, a peptide, a lipid, a polysaccharide, a nucleic acid, and a nucleic acid analogue. In some embodiments, the nanoantenna array can be used for spectrometry which uses spectrally narrow far-field extinction resonances, or for the spectrometry uses enhanced near-field intensities at the extinction resonances, for example, spectrometry which uses infra red wavelengths, or is vibrational spectroscopy.

Another aspect of the present invention relates to the use of a nanoantenna array as disclosed herein for enhancing near-field electromagnetic fields in spectrometry. Another aspect of the present invention relates to the use of a nanoantenna array as disclosed herein for enhancing near-field infra-red electromagnetic fields in spectrometry, for example, where the infra-red wavelength is mid-infrared frequency, such as, for example, amide-I (1660 cm-1) and amide-II (1537 cm-1) frequencies.

Another aspect of the present invention relates to the use of a nanoantenna array as disclosed herein for use in collective excitations of plasmons in spectrometry.

Another aspect of the present invention relates to the use of a nanoantenna array as disclosed herein in a method for chemical imaging a target molecule, for example, a target bioanalyte, or a target molecule selected from the group of: bioanalyte, chemical, metabolite, toxin, agent, pathogen, cell, gas, virus, prion.

Another aspect of the present invention relates to a method of making a nanostencil for nanostencil lithography fabrication of a nanoantenna array, for example a plasmonic nanoantenna array as disclosed herein, comprising: (a) coating a carrier wafer with a ceramic material to provide a first ceramic layer and a second ceramic layer; (b) cleaning the ceramic layers with an organic solvent; (c) applying a photoresist coating to the first ceramic layer; (d) defining a first aperture using photolithography; (e) etching the first ceramic layer to produce a first aperture in the first ceramic layer; (f) etching the carrier to extend the first aperture through the carrier wafer to the second ceramic layer; (g) applying an e-beam resist to the second ceramic layer; (h) applying an electron beam to the e-beam resist on the second ceramic layer to create a predefined pattern of nanoapertures in the e-beam resist; (i) developing the e-beam resist; and (j) etching the predefined pattern of nanoapertures through the second ceramic layer.

Another aspect of the present invention relates to a nanostencil for use in high-throughput nanostencil lithography fabrication of a nanoantenna array as disclosed herein.

In some embodiments, a carrier wafer includes a silicon wafer and the ceramic layers include $Si_yN_x$, materials, e.g. silicon nitrites and the like. In some embodiments, a second ceramic layer is a low pressure chemical vapor deposition silicon nitride film. In some embodiments, a carrier wafer is approximately 500 microns thick and the ceramic layers are approximately 400 nm thick, and in some embodiments, a predefined pattern of nanoapertures includes at least one aperture measuring approximately 1200 nm or less by 250 nm or less. In some embodiments, a predefined pattern of nanoapertures is any pattern suitable for a nanoantenna array as disclosed herein, for example, a periodic or non-periodic pattern, and the shapes of the nanoappertures include, but is not limited to a nanorod, a nanodisc, a nanoantenna, a nanowire, nanotriangle, or a nanoparticle, and can include nanoapertures in collections, for collections of corresponding nanostructures, e.g., dimers, trimers, bow-tie, and star collections and the like.

Another aspect of the present invention relates to a method of depositing a nanostructure on a support comprising: (a) preparing a nanostencil having a predefined pattern of one or more nanoapertures corresponding to a desired pattern; (b) placing the nanostencil membrane in contact with the support; (c) depositing the material on the support through the nanostencil membrane; and (d) removing the nanostencil from contact with the support to leave the nanostructure.

In some embodiments, a nanostructure is a plasmonic nanostructure, for example, comprising a plasmonic material. In some embodiments, a nanostensil has one or more nanoapertures corresponding to a desired shape and predefined desired pattern of the nanostructures, wherein the desired shape and pattern of nanostructures is a controlled geometric shape and controlled periodic pattern of the nanostructure with respect to other nanostructures designed for collective excitation of plasmons and localized plasmon resonance. In some embodiments, a nanostructure is not a plasmonic nanostructure, for example, where a nanostructure does not contain a plasmonic material. For example, in some embodiments, a non-plasmonic nanostructure comprises at least one or a combination of agents, nucleic acid, proteins, biomaterials, regrowth agents for other materials.

In some embodiments, a method of depositing a nanostructure on a support further comprises (a) cleaning the nanostencil membrane; (b) placing the nanostencil membrane in contact with a second support; (c) depositing the material on the second support through the nanostencil membrane; and (d) removing the mask from contact with the second support to leave the nanostructure.

In some embodiments, a deposited material is a plasmonic material, for example, a metallic material, including but not limited to, selected from the group consisting of: gold (Au), Silver (Ag), Rhodium (Rh), Palladium (Pd), Osmium (Os), Iridium (Ir), Platinum (Pt), Titanium (Ti) and Aluminum (Al), or any combination thereof. In some embodiments, a plasmonic material is selected from the group consisting of: Gold (Au), Silver (Ag), Platinum (Pt), Copper (Cu), Aluminum (Al), Palladium (Pd), Iron (Fe), Vanadium (V), Molybdenum (Mb) or alloys thereof, or any combination thereof.

In some embodiments, a deposited material is not a plasmonic material, for example, non-plasmonic material can be selected from at least one or a combination of biomaterials, agent, proteins, nucleic acids, nucleic acid analogues, regrowth agents for other materials. In some embodiments, the nanostructures are deposited in predefined pattern such as a periodic pattern, or a non-periodic pattern.

Another aspect of the present invention relates to a nanoantenna array fabricated according to the nanostencil lithography (NSL) method as disclosed herein.

Another aspect of the present invention relates to a method of depositing a nanostructure on a support comprising: (a) providing a nanostencil membrane having a predefined pattern of one or more nanoapertures corresponding to a desired pattern; (b) placing the nanostencil membrane in contact with the support; (c) depositing the material on the support through the nanostencil membrane; and (d) removing the nanostencil from contact with the support to leave the nanostructure. In some embodiments, the method further comprises: (e) cleaning the nanostencil membrane; (f) placing the nanostencil membrane in contact with a second support; (g) depositing the material on the second support through the nanostencil membrane; and (h) removing the mask from contact with the second support to leave the nanostructure.

In some embodiments, a nanostructure is a plasmonic nanostructure, for example, where the material deposited includes a plasmonic material, such as, for example, a noble metal. In some embodiments, a plasmonic material is a directional gold material, or a metallic material, for example, but not limited to, gold (Au), Silver (Ag), rhodium, palladium, osmium, iridium, platinum (Pt), titanium (Ti) and Aluminum (Al), Palladium (Pd), or any combination thereof. In some embodiments, a plasmonic material deposited is selected from the group consisting of: gold (Au), Silver (Ag), platinum (Pt), Copper (Cu), Aluminum (Al), Palladium (Pd), iron, vanadium, molybdenum or alloys thereof, or any combination thereof. In some embodiments, a plasmonic material is deposited at 3×10-6 Torr in an e-beam evaporator to produce a layer of plasmonic material at a predefined thickness on the support.

In alternative embodiments, a nanostructure generated is not a plasmonic nanostructure, as a result of the depositing of a material is not a plasmonic material, for example, where the non-plasmonic material is selected from at least one or a combination of biomaterials, proteins, nucleic acids, nucleic acid analogues, regrowth agents for other materials.

In some embodiments, a nanostencil membrane is a flexible nanostencil membrane. In some embodiments, a support which has material deposited on includes a sticky or elastic surface, or it includes a flexible support, which is useful for example, when it is desirable to wrap the flexible support around a curved element, for example, around the surface of a fiber optic cable. In some embodiments, a support is a thin-film support, for example, a stretchable support on elastic stretchable support, selected from, for example, but not limited to, LDPE film, parylene C, and PDMF thin film.

Another aspect of the present invention relates to a nanoantenna array device fabricated according to any of the methods as disclosed herein.

Another aspect of the present invention relates to a method of fabricating a nanostencil comprising; (a) fabricating a free-standing membrane having a substantially uniform thickness, and (b) producing a predefined pattern of one or more nanoapertures through the free standing membrane. Another aspect of the present invention relate to a method for detecting one or more molecular targets comprising; (a) providing a nanoantenna array of any of paragraphs 1 to 49; (b) contacting one or more samples comprising one or more target molecules to the surface of the nanoantenna array; (c) illuminating one or more surfaces of the nanoantenna array with an incident light source to produce surface plasmons, before and after the contacting with one or more samples, (d) collecting and measuring light displaced from the illuminated film with an optical detection system, before and after contacting with one or more samples, and (e) detecting one or more target molecules based on the change or difference in the measurement of light displaced from the illuminated film before and after contacting with the one or more samples. In some embodiments, a target molecule is a target bioanalyte, and can be a selected from the group of: bioanalyte, chemical, toxin, agent, pathogen, cell, gas, virus, prion.

Another aspect of the present invention provides for high-throughput fabrication of a nanoantenna array which has optical qualities comparable or superior to that of nanoantenna arrays fabricated by other means, for example, electron beam lithography. In some embodiments, the methods and processes for high-throughput fabrication of nanoantenna arrays involves nanostencil lithography (NSL) fabrication methods, enabling nanostructures (of plasmonic or non-plasmonic materials) of predefined shapes to be arranged in predefined patterns, e.g., in organized or a periodic array configuration. In addition, the nanostencil masks as described herein for the nanofabrication processes according to the invention can be reused many times to fabricate many series of nanostructures, or complex nanoantenna arrays with identical optical responses at a relatively low cost. Furthermore, the processes according to the invention provide the flexibility and the resolution to create complex plasmonic nanostructures on supports that are difficult to produce using e-beam and ion beam lithography tools. The inventors have shown that large field enhancements in nanoplasmonics can lead to ultra-sensitive infrared spectroscopy and have shown detection of vibrational signatures of proteins at zepto-mole sensitivity levels (Adato, R et al., *PNAS* 2009, 106, 46, 19227-19232)

The nanostencil lithography (NSL) fabrication methods as disclosed herein can be used for fabricating nanoantenna arrays comprising nanostructures compositing plasmonic material, or alternatively non-plasmonic materials, such as, but not limited to, viruses, pathogens, prions, bioanalytes, cells, proteins and regrowth agents and the like. In particular, in some embodiments, the nanostencil lithography (NSL) fabrication methods as disclosed herein can be used to deposit nanostructures comprising regrowth agents, e.g., carbon nanotubes, which serves as a seed for regrowth of additional carbon nanotubes at predefined locations.

Another aspect of the present invention relates to nanostencils (also referred to herein as "nanostencil mask") for high-throughput fabrication of a nanoantenna arrays, where in some embodiments, the nanostencils comprises nanoapertures in a membrane made from a ceramic material, such as a SiNx material. The membrane can be mounted to a silicon carrier. The nanoaperture pattern in the nanostencil can be applied to the membrane using an etching or electron beam lithography process. The resulting nanostencil mask can be used as a mask or template to directly deposit plasmonic nanostructures on virtually any desired support.

Also described herein are methods of fabricating complex patterns of plasmonic nanostructures, for example on a nanoplasmonic antenna array as described herein. Such plasmonic nanostructures and nanoantenna arrays can be fabricated by clamping the stencil mask directly to a support and directly depositing a plasmonic material onto the support through the nanostencil mask. When the nanostencil mask is removed, the plasmonic nanostructures remain affixed to the support in a pattern complimentary to the nanoaperture pattern.

In one aspect, methods of making or fabricating a nanostencil are described herein. Such methods comprise: (i) coating a carrier wafer with a ceramic material to provide a first ceramic layer and a second ceramic layer; (ii) cleaning the first and second ceramic layers with an organic solvent; (iii) applying a photoresist coating to the first ceramic layer; (iv) defining a first aperture using photolithography; (v) etching the first ceramic layer to produce a first aperture in the first ceramic layer; (vi) etching the carrier to extend the first aperture through the carrier wafer to the second ceramic layer; (vii) applying an e-beam resist to the second ceramic layer; (viii) applying an electron beam to the e-beam resist on the second ceramic layer to create a predefined pattern of nanoapertures in the e-beam resist; (ix) developing the e-beam resist; and (x) etching the predefined pattern of nanoapertures through the second ceramic layer.

Another method of fabricating a nanostencil comprises fabricating a free-standing membrane having a substantially uniform thickness, and producing a predefined pattern of one or more nanoapertures through the free standing membrane, thereby fabricating a nanostencil.

In some embodiments of these methods of fabricating nanostencils, the carrier wafer is a silicon wafer and the ceramic layers are SiNx materials. In some embodiments of the methods, the second ceramic layer is a low pressure chemical vapor deposition silicon nitride film. In some embodiments of the methods, the carrier wafer is approximately 500 microns thick and the ceramic layers are approximately 400 nm thick. In some embodiments of the methods, the predefined pattern of nanoapertures includes at least one aperture measuring approximately 1200 nm or less by 250 nm or less. In some embodiments of the methods, the predefined pattern of nanoapertures include a nanorod, a nanodisc, a nanoantenna, a nanowire, or a nanoparticle.

Another aspect described herein relates to methods of depositing at least one plasmonic nanostructure on a support. In such aspects, the methods comprise: (i) preparing a nanostencil having a predefined pattern of one or more nanoapertures corresponding to the desired shape of the plasmonic nanostructure according to any of the methods described herein for making a nanostencil; (ii) placing the nanostencil membrane in contact with the support; (iii) depositing the plasmonic material on the support through the nanostencil membrane; and (iv) removing the nanostencil from contact with the support to leave at least one plasmonic nanostructure on the support. Accordingly, the methods of depositing at least one plasmonic nanostructure on a support can be used to fabricate the nanoantenna arrays as disclosed herein, wherein the nanostensil has a plurality of nanoapertures which correspond to the desired spatial and geometric configurations of the plurality of plasmonic nanostructures of the nanoantenna array.

In some embodiments, the methods of depositing at least one plasmonic nanostructure on a support can further comprise: (i) cleaning the nanostencil membrane; (ii) placing the nanostencil membrane in contact with a second support; (iii) depositing the plasmonic material on the second support through the nanostencil membrane; and (iv) removing the mask from contact with the second support to leave the at least one plasmonic nanostructure on the support.

In such an aspect, another method of depositing at least one plasmonic nanostructure on a support comprises: (i) providing a nanostencil membrane having a predefined pattern of one or more nanoapertures corresponding to the desired shape of the plasmonic structure; (ii) placing the nanostencil membrane in contact with the support; (iii) depositing the plasmonic material on the support through the nanostencil membrane; and (iv) removing the nanostencil from contact with the support to leave the plasmonic nanostructure on the support.

Some embodiments of the methods of depositing a plasmonic structure on a support described herein further comprise: (i) cleaning the nanostencil membrane; (ii) placing the nanostencil membrane in contact with a second support; (iii) depositing the plasmonic material on the second support through the nanostencil membrane; and (iv) removing the mask from contact with the second support to leave the plasmonic structure. Accordingly, the methods of depositing at least one plasmonic nanostructure on a support can be used to fabricate the nanoantenna arrays as disclosed herein, wherein the nanostensil has a plurality of nanoapertures which correspond to the desired spatial and geometric configurations of the plurality of plasmonic nanostructures of the nanoantenna array.

In some embodiments of these methods of depositing plasmonic nanostructures, the plasmonic material is a directional gold material. In some embodiments, the plasmonic material can be deposited at $3\times10$-6 Torr, using, for example, an e-beam evaporator to produce a layer of plasmonic material at a predefined thickness on the support.

Other aspects provide novel plasmonic structures, e.g., nanoantenna arrays, fabricated according to any of the methods of depositing a plurality of plasmonic nanostructures on a support described herein. In some embodiments, the support of the plasmonic structures, e.g., nanoantenna arrays, fabricated according to the methods described herein comprise a support, for example, where the support is non-conducting material. In some embodiments, the support allows nanostructures to be embedded or attached to the surface of the support, where the nanostructures, e.g., nanoantenna arrays can comprise a conducting material, a non-conducting material, or a magnetic material. In some such embodiments, the conducting material comprises silicon. In some embodiments, the non-conducting material comprises glass, quartz, or calcium fluoride ($CaF_2$).

In some embodiments of the aspects, the plasmonic nanostructures fabricated according to the methods described herein can be any, or a combination of a nanorod, a nanodisc, a nanoantenna, a nanowire, a nanoparticle, or any combination therein. In some embodiments, a nanoantenna array as disclosed herein which comprises a plurality of plasmonic nanostructures can comprise any combination of plasmonic nanostructures of different plasmonic materials and geometric configurations, e.g., can comprise any combination of nanorods, nanodiscs, nanoantennas, nanowires, nanoparticles and the like.

BRIEF DESCRIPTION OF THE FIGURES

FIGS. 1A-1B show gold plasmonic nanorods offer antenna-like functionality in the Mid-IR frequency range. FIG. 1A shows the reflectance spectra of randomly arranged plasmonic nanorods yield the individual antenna behavior. The rod length is indicated in the legend (nm), and all structures are approximately 230 nm wide. The polarization of the incident electric field is aligned to be parallel to the long (short) axis of the rod for the solid (dashed) curves. FIG. 1B shows the resonant wavelength of the fundamental antenna resonance (blue squares) is approximately linearly dependent (dashed line shows a linear fit) on the rod length. The inset shows a scanning electron microscope (SEM) image of a nano-rod with polarization directions.

FIG. 2A shows cross-sections of the intensity distribution taken through the edge of the rod are shown for periodic (d=1.6 µm) and isolated antenna. FIG. 2B shows the evanescent (left) and radiative (right) diffractive coupling effects are illustrated.

FIG. 3A shows scanning electron microscope (SEM) images of a periodic array. FIG. 3B shows the reflectance spectra of periodic nanoantenna arrays. All the antennas are 1100 nm long. The wavenumbers corresponding to $1/\lambda_{Si(1,0)}$ for a given periodicity are indicated by the dashed lines at the top of the figure. FIG. 3C shows the variation in peak position (squares) and linewidth (triangles) with the grating period are shown. The dashed line indicates the wavelength at which the grating order transitions from evanescent to radiative in character. The grating order is evanescent in the shaded region.

FIG. 4A shows silk film thickness is measured by atomic force microscopy for a 4 nm thick film.

FIG. 5A shows incident light radiation driving the antenna and the coupling between the antenna and its protein load are described by the NEGF formalism. FIG. 5B shows the model reproduces the symmetric (asymmetric) lineshapes, when the antenna is resonant (offset) with the amide-II band (1537 cm$^{-1}$). FIG. 5C shows difference spectra of the antenna whose resonance is tuned to 1450 cm$^{-1}$ (red curve) and 1700 cm$^{-1}$ (green curve). Relative strength of the absorption peaks is controlled by the nanoantenna resonance.

FIG. 6A shows the different spectra for a periodic array with d=1.6 µm and 1100 nm long rods for different silk film thicknesses. The legend indicates the thickness values. FIG. 6B shows the signal strength of the amide-I absorption feature (left axis) as a function of film thickness for the 1.6 and 2 µm periodic and the randomized arrays (arrays have 1100 nm long rods). Signals are normalized to take into account the different numbers of rods in each array. The dashed green line shows the computed sampling volume's dependence on the silk film thickness for the 1.6 µm periodic antenna array.

FIGS. 8A-8D show an embodiment fabricating a nanoantenna array using a conventional liftoff process. Other embodiments for fabricating nanoantenna arrays use high-throughput fabrication as shown in FIG. 17A. FIG. 8A shows a layer of template material (e.g., PMMA) on the support (e.g., silicon support), FIG. 8B shows the next step of pattern development using any means known by one of skill in the art such as etching or laser, FIG. 8C shows the step of plasmonic material deposition (e.g., with a metallic material), and FIG. 8D shows lift-off of the template material to leave the nanostructures on the surface of the support.

FIG. 9A shows the dependence of the randomization procedure on nanostructure density on a nanoantenna array and rod length for 300 nm wide nanostructures. A relatively large variation in the predefined pattern of nanostructures density (or periodicity) of between 0.11 µm$^{-2}$ or 0.33 µm$^{-2}$ of different nanorod lengths results in essentially the same resonance behavior, demonstrating that the measurement of the far field response from a predefined pattern of nanostructures is repeatable and an accurate representation of the individual antenna behavior. FIG. 9B and FIG. 9C shows electron micrograph (EM) images of an embodiment where the nanostructure is a nanorod, where FIG. 9B shows the height (H2) of the nanorod as 71.33 nm and the length as 802.2 nm and the proximal and distal end having a tapering width of 77.75 nm. FIG. 9C shows EM images of a plurality of nanostructures of a predefined shape, e.g., nanorods, in a predefined pattern on the support surface of the array.

FIG. 10A shows a lattice sum and FIG. 10B shows extinction spectra are shown for 1D nanoparticle chains. The particles are gold ellipsoids with dimensions 1.6×0.3×0.1 µm and the background refractive index is 3. A modified long wavelength approximation (MWLA) is used for the single particle polarizability. The particles are arranged on a 2.8 µm periodic chain. Light is normally incident and polarized perpendicular to the chain axis. The real part of S diverges at the grating transition wavelength (vertical dashed line in (FIG. 10A)) while the imaginary part exhibits a drastic sign change. At wavelengths below the transition wavelength, a grating order has radiative (FIG. 10C) or evanescent (FIG. 10D)) in character.

FIG. 11A shows an embodiment of the fabrication process. FIG. 11B shows a nanoantenna array with on-support plasmonic nanostructures. FIG. 11C shows a nanoantenna array with embedded plasmonic nanostructures which are embedded below the surface of the support. FIG. 11C (inset) also shows a cross section view to show a vertical wall profile. FIG. 11D shows SEM images of nanoantenna arrays, with FIG. 11D(i) showing a fabricated random array and FIG. 11D(ii) showing periodic (in square lattice) on-support nanostructures (e.g., nanorods) on the nanoantenna arrays, and FIG. 11D(iii) showing a fabricated random array and FIG. 11D(iv) showing periodic (in square lattice) for embedded nanostructures (e.g., nanorods) on the nanoantenna arrays.

FIG. 12A shows length dependence of the resonance wavelength for Au rods on a Si support. Experimentally obtained resonances for the m=1 (black) and m=3 (blue) modes are shown fitted to dipole antenna relation given in Eq. (11). ($\lambda_{Res}$=$(2n_{eff}/m)L+C$). Effective indices determined from linear fits are indicated. The constant term, C, was 0.16 µm and 0.26 µm for the $1^{st}$ and $3^{rd}$ order modes, respectively. The insets correspond to the field distribution for z component of the electric field in a plane below the surface of the rod. FIG. 12B shows red-shifting of the resonances is experimentally observed for embedded (d=200 nm) individual nanoantennas as compared to on-support (d=0) ones. Analytical and numerical calculations based on the ideal dipole approximation (green dashed line) and 3D FEM simulations (black stars, red dashed line indicates linear fit) are shown for the embedded rods.

FIG. 13A shows extinction spectra for embedded nanostructures (d=200 nm) and FIG. 13B shows extinction spectra for on-support nanostructures on nanoantenna arrays. The diffraction edges are indicated by the dashed vertical lines at the bottom of the figures. The feature at ~8 µm in FIG. 17A is associated with the formation of a thin oxide layer on the Si supports.

FIG. 14A shows the real and imaginary parts of the lattice sum (S) for a 2D periodic (P=1.4 µm) array. S is calculated via truncated numerical evaluation as described in section 2. The grating transition wavelengths are indicated by the dotted vertical lines. FIG. 14B shows the computed extinction efficiency for a single ellipsoidal particle (black curve) and a 2D array of 10×10 particles (red curve) via the CD method are shown. FIG. 14C shows shifting in resonant wavelengths with varying periodicity for the on-support and embedded arrays are shown. Analytically obtained grating transition wavelengths for Si-(1,0), Si-(1,1), Si-(2,0) are also shown with dashed lines. Dotted blue/red lines correspond to the individual nanorod antenna resonance of on-support/embedded arrays. FIG. 14D shows embedded 800 nm long nano-rods with 1.5 µm periodicity displays perfect transmission in the vicinity of a grating transition wavelength.

FIGS. 15A-15B show 3D FDTD simulated extinction spectra. FIG. 15A shows the 3D FDTD simulated extinction spectra for embedded nanostructures (d=200 nm). FIG. 15B shows the 3D FDTD simulated extinction spectra for on-support nanostructures (e.g., nanorods) on nanoantenna arrays for varying array periodicities (L=800 nm for both).

FIG. 16A shows the spatial distribution at the edge of an isolated nanorod particle in homogenous silicon background, FIG. 16B shows the spatial distribution at the edge of an isolated nanorod particle in a periodic array fabricated on silicon support, and FIG. 16C shows the spatial distribution at the edge of an isolated nanorod particle in a periodic array embedded in 200 nm beneath the silicon support. FIG. 16D shows the spatial distribution in the center vertical plane of an isolated nanorod particle in homogenous silicon background, FIG. 16E shows the spatial distribution in the center vertical plane of an isolated nanorod particle in a periodic array fabricated on silicon support.

FIG. 17B(i) shows nano-antenna arrays fabricated according to an embodiment of the invention. FIG. 17B(ii) shows a process for fabricating plasmonic structures according to an embodiment of the invention. FIG. 17B(iii) shows a nanostencil mask according to an embodiment of the invention.

FIG. 23A shows a circular gold nano-antenna array; FIG. 23B shows gold nanowires, and FIG. 23C shows a gold nano-rod array.

FIGS. 24A-24B show embodiments where the nanostencil lithography fabrication can be used to deposit nanostructures on thin-films for a tunable plasmonic antenna array. For example, nanostencil lithography (NSL) enables tunable plasmonic antenna array fabrication on flexible, mechanically or thermally stretchable/ shrinkable, thin or thick visibly transparent/nontransparent supports, such as parylene C and LDPE thin films (~10 µm) or, thin and thick (up to 1-2 cm) PDMS substrate. FIG. 24A shows a electron microscopy (SEM) image of one example of a nanostencil used for nanostencil lithography, and FIG. 24B shows a SEM image of gold nanorod nanostructures in an array of a predefined pattern (as determined by the predefined pattern of nanoapertures of the nanostensil) on a thick PDMS substrate. It can be seen from FIG. 24B that there are no variations observed on nanostructure dimensions or periodicty. Electron microscope images and spectroscopic results demonstrate that the NSL technique on flexible supports, such as parylene C film or PDMS or LDPE thin films provides identical fabrication and resolution as compared to other planar supports like Si, SiN, glass, CaF, etc.

FIG. 25A shows a nanoantenna array fabricated by the nanostensil lithography (NSL), where the support is a thin film which comprises a predefined pattern of plasmonic nanostructures which can be fine tuned by altering the shape (e.g., by stretching, or wrapping the support around a curved surface) of the thin film support. FIG. 25A shows the nanoantenna array which comprises a pattern of plasmonic gold circular nanodisks on a 10 µm parylene C film, which is wrapped around a curved surface, e.g., a fiber optic surface. FIG. 25B shows a lower magnitude image of such a gold nanodisc array on a 10 µm parylene C film wrapped on the fiber optic cable with 300 µm diameter.

FIG. 26A shows the transmission spectra of a gold nanorod antenna array at a fixed periodicity of 1.6 µm on a 5 µm thick Parylene C support with the lengths of the nanorods changing from 1 µm to 1.2 µm in length. FIG. 26B shows the transmission spectra of a 1000 µm length gold nanorod antenna array on a 5 µm thick Parylene C support with the periodicity changing from 1.5 µm to 1.8 µm. The transmission of the 5 µm thick Parylene C support is also shown (dotted line). Spectra are obtained by using FTIR.

FIG. 27A shows the dimensions of nanostructures on a support, e.g., a thin-film support in a relaxed shape. FIG. 27B shows the dimensions of the nanostructures on the support, e.g., thin-film support following a stretching of the support. The dimensions of the nanostructures has increased in length and decreased in height and/or width. The stretching can occur by mechanical means (e.g., mechanical stretching) or by thermal means (e.g., thermal heating to enlarge or shrink the thin-film support). FIG. 27C shows a schematic graph demonstrating a shift in the plasmonic response which is tailored or tuned to a different wavelength due to the changing shape, e.g., stretching, of the support comprising the plasmonic nanostructures (where the changing shape of the support also changes the dimensions and/or the plurality of the nanostructures on the support).

FIG. 28A shows a shift in the resonance location of nanostructures on 13 µm LDPE film (commonly known as Glad Cling Wrap), before (unstretched) and after mechanical stretching (stretched). No deformation on the nanoparticles during stretching and after stretching was observed. SEM results revealed that stretching changed only the periodicity but not the dimensions of the nanostructures, and that the nanostructures are intact after stretching and releasing at least for two times. FIG. 28A shows a 160 nm red shift on resonance wavelength location when the film with array of nanorod gold particles with 1.5 µm periodicity, 1200 nm length is mechanically 5% stretched on the plane perpendicular to rod elongation. FIG. 28B shows the shift on resonance location when film with an array of gold nanorod nanostructures with 1.8 µm periodicity, 900 nm length is mechanically 16% stretched on the plane perpendicular to rod elongation. Theoretical calculations (stimulations) and optical microscopy images confirm that periodicity of the particles changed from 1.8 µm (unstretched) to 2.1 µm (stretched).

FIG. 29A shows a gold nanorod antenna array fabricated on PDMS support using the NSL fabrication with a nanostensil having a nanoaperture dimensions of 245 nm×940 nm. Nanorod nanostructures on PDMS have the dimensions of 240×935 nm, which is almost exactly complementary to the nanostencil used. No gold particle scattering is observed around any of the nanorods. FIG. 29B shows a gold nanorod antenna array fabricated on a silicon (Si) support using the same nanostencil with same dimensions. On the silicon support, due to a finite gap, the nanorods have a dimension of 327 nm×1053 nm, demonstrating there a clear enlargement of the size of the nanorod as compared to the size of the nanoaperture of the nanostencil. In addition, FIG. 29B shows gold particle scattering within a 20 nm vicinity of each of the nanorod nanostructures. Below you can see average dimension values for stencil used and nanorods on PDMS and Si. FIG. 29C shows the height dimensions of a gold nanorod nanostructures fabricated on PDMS support using the NSL fabrication. The height dimensions of all the nanorods measured in the array are consistent with each other and are approximately 150 nm, which is exactly the desired metal thickness deposited, and shows no gold scattering between the gold nanorod structures. FIG. 29D shows the height dimensions of gold nanorod antenna array fabricated on a silicon (Si) support using the same nanostencil. The height dimensions of all the nanorods are approximately 30% smaller, and are between about 110-115 nm and also shows significant gold scattering between each of the gold nanorod structures, for example within about a 20-30 nm vicinity of each gold nanorod.

DETAILED DESCRIPTION OF THE INVENTION

Figure 2A:
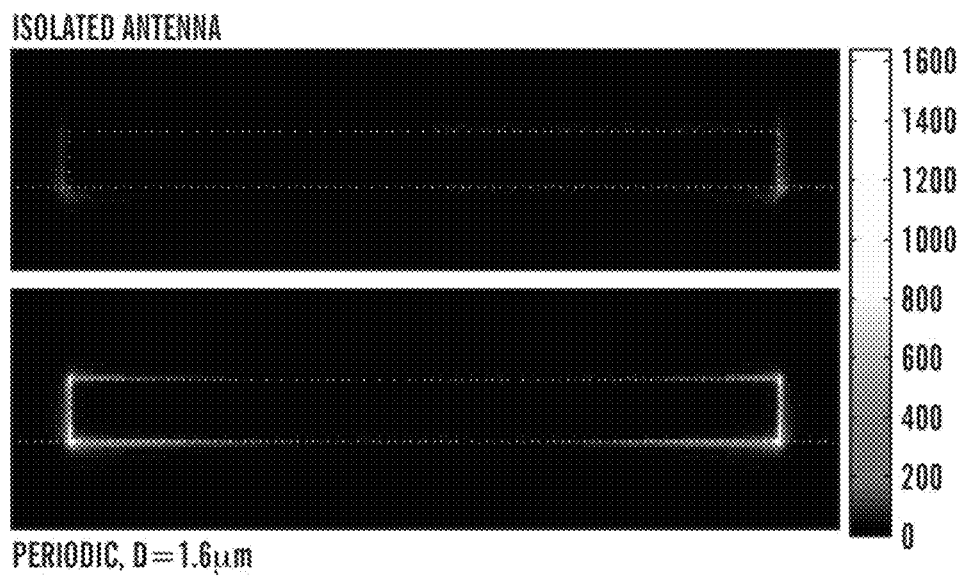
FIGS. 2A-2B show collective resonances in periodic arrangements of nanoantennas can give rise to nearly an order of magnitude larger near-field intensity enhancements in comparison to the isolated antenna.

One aspect of the present invention relates to, in part, a nanoantenna array comprising nanostructures which are arranged on, or depressed within a support, where the nanostructures have a predefined shape and predefined arrangement with respect to each other for collective resonance. In some embodiments, the nanostructures comprise plasmonic material. In some embodiments, the predefined arrangement of the nanostructures of the nanoantenna array is a periodic arrangement, or a non-periodic arrangement, or a uniform arrangement, or a lattice arrangement, or a non-random arrangement, or combinations thereof.

The present invention also includes methods for high-throughput nanofabrication of such nanoantenna arrays, such as plasmonic nanoantenna arrays as disclosed herein, as well as other nanoantenna arrays comprising nanostructures which do not comprise plasmonic material. Additionally, the present invention relates to devices, such as nanostensils and method of nanostencil lithography for fabricating nanoantenna arrays as disclosed herein. These techniques allow for the fabrication of nanoantenna arrays, such as plasmonic nanoantenna arrays with high uniformity, reproducibility, and repeatability, without using operationally slow and expensive electron/ion-beam lithograpy tools. Devices fabricated according to the invention are shown to have comparable optical characteristics with respect to the arrays fabricated by prior art EBL. In addition, the nanostencil described herein can be reused for high-throughput fabrication of any nanoplasmonic structures, such as antenna arrays, by simply removing the metal residue with a mild metal etchant. Methods according to the present invention offer flexibility and resolution to radiatively engineer nanostructures, such as nanoantenna arrays for excitation of collective plasmonic resonances. These excitations, by enabling spectrally narrow far-field resonances and enhanced near-field intensities, are highly suitable for ultrasensitive vibrational nanospectroscopy applications, such as bioanylate detections and measuremens. In addition to its high-throughput capability, the present invention enables fabrication of plasmonic devices on surfaces otherwise difficult to work with using prior art techniques. Successful fabrication of plasmonic devices on non-conducting surfaces, such as glass and $CaF_2$ has been performed, as described herein. In addition, the present invention can be used to fabricate various nanoscale plasmonic structures, such as nanowires, nanorods, and nanodisks. Accordingly, the fabrication methods according to the invention can be used for designing plasmonic nanodevices and nanostructures for various applications.

These and other capabilities of the invention, along with the invention itself, will be more fully understood after a review of the following figures, detailed description, and claims.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "nanoantenna array" as used herein refers to a collection of nanostructures (e.g., plasmonic nanostructures or nanoantennas) of a predefined shape arranged in a predefined pattern on a support. In some embodiments, the predefined pattern is a periodic pattern or a uniform pattern.

The terms "nanostructure," "nanomaterial," and "nanoparticle" are used interchangeably herein and refer a structure having a dimension of a material at the atomic, molecular or macromolecular levels, in the length scale of approximately 1-3000 nm range, for example, in the range of about 1-2500 nm, in the range of about 1-2000 nm, in the range of about 1-1500 nm, in the range of about 1-1000 nm, in the range of about 10 nm to about 1000 nm, in the range of about 10 nm to about 750 nm, in the range of about 10 nm to about 500 nm, in the range of about 10 nm to about 250 nm, in the range of about 10 nm to about 100 nm, in the range of about 2 nm to about 100 nm, or in the range of about 2 nm to about 100 nm. Such a nanostructure, whether comprising plasmonic material or non-plasmonic material, can be present on or embedded (e.g., depressed) within the surface of a substance or substrate. A nanostructure can have one dimension of about 300 nm or less, about 250 nm or less, about 240 nm or less, about 230 nm or less, about 220 nm or less, about 210 nm or less, about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, about 20 nm or less, or about 10 nm or less; and a second dimension of about 1500 nm or less, about 1400 nm or less, about 1300 nm or less, about 1200 nm or less, about 1100 nm or less, about 1000 nm or less, about 900 nm or less, about 800 nm or less, about 700 nm or less, about 600 nm or less, or about 500 nm or less. The nanostructures of the present invention have a preselected shape and can be a nanotube, a nanowires, nanosphere, or any shape comprising the above-described dimensions (e.g., triangular, square, rectangular, or polygonal shape in 2 dimensions, or cuboid, pyramidal, spherical, discoid, or hemispheric shapes in the 3 dimensions).

The terms "plasmonic nanostructure" or "nanoplasmonic structure" or "nanoantenna" are used interchangeably herein and refer to any independent structure exhibiting plasmon resonance characteristic of the structure, including (but not limited to) both nanostructures, nanoparticles and combinations or associations of nanoparticles, such as nanorod and nanoantenna arrays described herein. For example, plasmonic nanostructures can be organized or designed to be in any predefined pattern that gives rise to a desired optical property for the nanostructure, such as a periodic pattern or a non-periodic pattern, including pseudo-random, super-periodic and unit cell patterns.

The term "predefined" as used with respect to "predefined pattern" refers to a pattern that is designed and selected to be used for the pattern of nanostructures in the nanoantenna array, or pattern of the nanoapertures of a nanostencil. The pattern design is selected so the nanostructures function in the pattern for collective excitation of plasmons and localized plasmon resonance. For example, the pattern of the nanostructures is designed and specifically selected for a function where an acting electric field ($E_{acting,i}$) on a single nanostructure is the sum of the incident electric field ($E_{incident,i}$) and the sum of a retarded dipolar field due to the other nanostructures in the nanoantenna array, and is characterized by the formula:

$$\vec{E}_{acting,i} = \vec{E}_{incident,i} + \sum_{i \neq j} \vec{E}_{retarded,ij} = \vec{E}_0 e^{i\vec{k}\cdot\vec{r}_i} + \sum_{i \neq j} \left(\vec{c}_{ij} \cdot \vec{P}_j\right) e^{ikr_{ij}}$$

where, $E_0$ is the incident field, $P_j$ is the induced polarization of j-th nanostructures structures in the array, and $c_{ij}$ is the dipolar interaction matrix among the plurality of plasmonic nanostructures without the phase term.

The term "predefined" as used with respect to "predefined shape" refers to shape of a nanostructure that was determined and selected to be used for the shape of nanostructures in the nanoantenna array, or shape of the void of the nanoapertures of a nanostencil.

The term "nanorod," as described herein, refers to a nanoplasmonic structure having one dimension of about 300 nm or less, about 250 nm or less, about 240 nm or less, about 230 nm or less, about 220 nm or less, about 210 nm or less, about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, about 20 nm or less, or about 10 nm or less; and a second dimension of about 1500 nm or less, about 1400 nm or less, about 1300 nm or less, about 1200 nm or less, about 1100 nm or less, about 1000 nm or less, about 900 nm or less, about 800 nm or less, about 700 nm or less, about 600 nm or less, or about 500 nm or less.

The term "nanohole" or "nanoaperture" are used interchangeably herein, and refers to an opening or aperture in a support, e.g., a support waiver of the nanostencil. In some embodiments, a nanohole refers to a recess or depression within a support of a nanoantenna array, for example, for placement of an embedded (e.g., depressed) nanostructure, such as a plasmonic nanostructure. Nanoapertures or nanoholes are preferably a sub-wavelength opening, such as a hole, a gap or slit, that causes or enhances the surface plasmon resonance properties of the plasmonic material in which it is present. As used herein, nanoholes or nanoapertures include symmetric circular holes, spatially anistropic shapes, e.g., elliptical shapes, slits, and also include any aperture of a triangular, square, rectangular, or polygonal shape. In some embodiments, a combination of different shaped nanoholes may be used. In addition, nanoholes can be through nanoholes that penetrate through a plasmonic material, such as a metal film, or non-through nanoholes that penetrate a part of a plasmonic material without completely penetrating through the plasmonic material. Preferably, a nanohole has a dimension of about 1500 nm or less, about 1400 nm or less, about 1300 nm or less, about 1200 nm or less, about 1100 nm or less, about 1000 nm or less, about 900 nm or less, about 800 nm or less, about 700 nm or less, about 600 nm or less, about 500 nm or less, about 450 nm or less, about 400 nm or less, about 350 nm or less about 300 nm or less, about 250 nm or less, about 240 nm or less, about 230 nm or less, about 220 nm or less, about 210 nm or less, about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, about 20 nm or less, or about 10 nm or less.

The term "periodicity" as used herein refers to a recurrence or repetition of the nanostructure at regular intervals by their positioning on the support of the nanoantenna array. The term "periodic" as used herein therefore refers to the regular predefined pattern of nanostructures with respect to each other.

The term "non-periodic" as used herein refers to a pattern of nanostructures which are in a pattern, but it is not a periodic pattern, or is not a lattice or other repeating unit configuration.

The term "lattice" as used herein refers to a repeating or reoccurring pattern of a unit or unit cell, where the unit cell can comprise one or more nanostructures. Typically, a unit cell comprising one or more nanostructures has the nanostructures in an organized predefined pattern with respect to each other. In some embodiments, the term "lattice" as referred to herein refers to the order or the type of partially ordered set. In some embodiments the lattice can be a discrete subgroup, which refers to a discrete subgroup of a topological group of nanostructures with finite covolume. In some embodiments, the lattice is a group lattice, which refers to a repeating arrangement of nanostructures.

The term "unit cell" refers to a collection of nanostructures in a predefined pattern, where the organized arrangement of a number of unit cells forms a lattice. Each nanostructure of a unit cell which belongs to one or more other unit cells in the lattice is referred to as a unit mode.

The term "controlled" as used herein refers to a non-random shape and/or non-random arrangement of the nanostructures with respect to each other on, or depressed within the support of the nanoantenna array.

The term "geometric shape" refers to the 2D and/or 3D shape of the nanostructure.

The term "surface plasmon resonance" refers to the physical phenomenon in which incident light is converted strongly into electron currents at the metal surface for planar surfaces, and "localized surface plasmon resonance (LSPR)" can also be used for surface plasmon resonance of nanometer-sized metallic structures. The oscillating currents produce strong electric fields in the (non-conducting) ambient medium near the surface of the metal. The electric fields, in turn, induce electric polarization in the ambient medium. Electric polarization is well known to cause the emission of light at wavelengths characteristic of the medium, i.e., the "Raman wavelengths." Additional background information regarding this phenomenon may be found in Surface Enhanced Raman Scattering, ed. Chang & Furtak, Plenum Press, NY (1982), the entire disclosure of which is incorporated herein by reference. As used herein, the term "Raman scattering" is intended to encompass all related physical phenomena where an optical wave interacts with the polarizability of the material, such as Brillouin scattering or polariton scattering.

As used herein, "surface plasmons," "surface plasmon polaritons," or "plasmons" refer to the collective oscillations of free electrons at plasmonic surfaces, such as metals. These oscillations result in self-sustaining, surface electromagnetic waves, that propagate in a direction parallel to the metal/dielectric (or metal/vacuum) interface. Since the wave is on the boundary of the metal and the external medium (air or water for example), these oscillations are very sensitive to any change of this boundary, such as the adsorption of a biomolecular target to the metal surface. Subsequently, the oscillating electrons radiate electromagnetic radiation with the same frequency as the oscillating electrons. It is this re-radiation of light at the same incident wavelength that is referred to as "plasmon scatter." These oscillations can also give rise to the intense colors of solutions of plasmon resonance nanoparticles and/or intense scattering. In the case of metallic nanoparticles, excitation by light results in localized collective electron charge oscillations, i.e., localized surface plasmon polaritions (LSPRs). They exhibit enhanced near-field amplitude at the resonance wavelength. This field is highly localized at the nanoparticle and decays rapidly away from the nanoparticle/dieletric interface into the dielectric background, though far-field scattering by the particle can also enhanced by the resonance. LSPR has very high spatial resolution at a subwavelength level, and is determined by the size of nanoparticles. "Plasmon absorption," as used herein, refers to the extinction of light (by absorption and scattering) caused by metal surface plasmons.

As used herein, a "plasmonic material" refers to a material that exhibits surface plasmon resonance when excited with electromagnetic energy, such as light waves, even though the wavelength of the light is much larger than the particle. For example, nanoparticles can be produced by chemical reactions in solutions. They are quite different from the same materials in bulky size, which do not exhibit quantum effects. In some embodiments of the aspects described herein, plasmonic materials as used refer to metallic plasmonic materials. Such metallic plasmonic materials can be any metal, including noble metals, and alloys. Preferred plasmonic materials include Au, Ag, Pt, Cu, Li, Na, K, Al, Pd, and Ni. Plasmonic materials, as described herein, elicit plasmon resonance when excited with electromagnetic energy. A plasmon resonant particle of a plasmonic material can be "optically observable" when it exhibits significant scattering intensity in the optical region (ultraviolet-visible-infrared spectra), when it exhibits significant scattering intensity in the optical region (ultraviolet-visible-infrared spectra), which includes wavelengths from approximately 100 nanometers (nm) to 3000 nm or several microns. A plasmonic material can be "visually observable" when it exhibits significant scattering intensity in the wavelength band from approximately 380 nm to 750 nm, which is detectable by the human eye, i.e., the visible spectrum. Plasmon resonance is created via the interaction of incident light with basically free conduction electrons, e.g., diameters preferably about 25 to 150 nm, more preferably, about 40 to 100 nm.

In some embodiments of the aspects described herein, a plasmonic nanostructure can comprise a "photonic crystal." As used herein, a "photonic crystal" refers to a substance or material composed of periodic dielectric or metallo-dielectric nanoelements that affect the propagation of electromagnetic waves (EM). Essentially, photonic crystals contain regularly repeating internal regions of high and low dielectric constant. Photons (behaving as waves) propagate through this structure—or not—depending on their wavelength. Wavelengths of light that are allowed to travel are known as modes, and groups of allowed modes form bands. Disallowed bands of wavelengths are called photonic band gaps. This gives rise to distinct optical phenomena. The periodicity of the photonic crystal structure has to be of the same length-scale as half the wavelength of an incident EM wave, i.e., the repeating regions of high and low dielectric constants have to be of this dimension. Accordingly, in some embodiments, a photonic crystal can be used in a biosensor device.

The term "support" refers to a conventional platform or scaffold in which to position the nanostructures in pre-defined patterns. As disclosed herein supports can be conducting or non-conducting materials. Supports can also be planar supports, non-planar supports (e.g., curved supports), such as beads, particles, dipsticks, fibers, filters, membranes, cables, optical fibers and silane or silicate supports such as glass slides. Support can be flexible or non-flexible (e.g. solid supports). Supports can also be thin supports, elastic and/or strechable supports (e.g, for active tuning of resondance), and thick supports. Supports can be sticky and elastic, e.g, for use with the nanostencil fabrication methods as disclosed herein.

As used herein, the term "resist" refers to both a thin layer used to transfer an image or [circuit] pattern, such as a circuit pattern, to a support which it is deposited upon. A resist can be patterned via lithography to form a (sub)micrometer-scale, temporary mask that protects selected areas of the underlying support during subsequent processing steps, typically etching. The material used to prepare the thin layer (typically a viscous solution) is also encompassed by the term resist. Resists are generally mixtures of a polymer or its precursor and other small molecules (e.g., photoacid generators) that have been specially formulated for a given lithography technology. Resists used during photolithography, for example, are called photoresists.

As used herein, "resist deposition" refers to the process whereby a precursor solution is spin-coated on a clean (e.g., semiconductor) support, such as a silicon wafer, to form a very thin, uniform layer. The layer is baked at a low temperature to evaporate residual solvent, which is known as "soft bake." This is followed by the "exposure" step, whereby a latent image is formed in the resist, e.g., (a) via exposure to ultraviolet light through a photomask with opaque and transparent regions or (b) by direct writing using a laser beam or electron beam. Areas of the resist that have (or have not) been exposed are removed by rinsing with an appropriate solvent during the development step. This step is followed by the post-exposure bake step, which is followed by a step of processing through the resist pattern using, for example, wet or dry etching, lift-off, doping. The resist deposition process is then ended via resist stripping.

As used herein, the process known as "lift-off" refers to the removal of residue of functional material adsorbed on the mask or stencil along with the template itself during template removal by, for example, dissolving it in a solvent solution.

The term "nanospectroscopy" refers herein to spectroscopy and measurement of the vibrational spectra of a target molecule, e.g., zepto-mole levels proteins for the entire nanoantenna array The term "analyte," "bioanalyte," "biomolecule," "target," or "target molecule" refers to a molecule of interest that is to be analyzed, detected, and/or quantified in some manner. The analyte can be a biological species, including, but not limited to, nucleic acids (DNA, RNA, modified oligonucleotides), proteins, carbohydrates, lipids, toxins, pathogens, bacterium cells, virus cells, cancer cells, normal cells, organisms, tissues. The analyte can be a Raman active compound or a Raman inactive compound. Further, the analyte can be an organic or inorganic molecule. Some examples of analytes may include a small molecule, a biomolecule, or a nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The analyte molecule may be a fluorescently labeled molecule, such as for example, DNA, RNA or protein. Disease cells refer to cells that would be considered pathological by a person of ordinary skill in the art, such as a pathologist. Non-limiting examples of disease cells include tumor cells, gangrenous cells, virally or bacterially infected cells, and metabolically aberrant cells.

The term "bioanalyte", "drug" or "compound" as used herein refers to a chemical entity or biological product, or combination of chemical entities or biological products. The chemical entity, bioanalyte or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. The bioanalyte can also be an agent.

The term "agent" as used herein refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the terms "sample," "biological sample" or "analyte" means any sample comprising or being tested for the presence of one or more target molecules or biomolecular targets, including, but not limited to cells, organisms (bacteria, viruses), lysed cells or organisms, cellular extracts, nuclear extracts, components of cells or organisms, extracellular fluid, media in which cells or organisms are cultured, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears and prostatic fluid. In addition, a sample can be a viral or bacterial sample, a sample obtained from an environmental source, such as a body of polluted water, an air sample, or a soil sample, as well as a food industry sample.

In some embodiments, a "biological sample" also refers to a cell or population of cells or a quantity of tissue or fluid from a subject. Most often, a sample has been removed from a subject, but the term "biological sample" can also refer to cells or tissue analyzed in vivo, i.e. without removal from the subject. Often, a "biological sample" will contain cells from a subject, but the term can also refer to non-cellular biological material, such as non-cellular fractions of blood, saliva, or urine, that can be used to measure protein phosphorylation levels. As used herein, a "biological sample" or "tissue sample" refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, a biological sample is from a resection, bronchoscopic biopsy, or core needle biopsy of a primary, secondary or metastatic tumor, or a cellblock from pleural fluid. In addition, fine needle aspirate biological samples are also useful. In some embodiments, a biological sample is primary ascite cells. Samples can be fresh, frozen, fixed or optionally paraffin-embedded, frozen or subjected to other tissue preservation methods, including for example methods to preserve the phosphorylation status of polypeptides in the biological sample. A biological sample can also mean a sample of biological tissue or fluid that comprises protein or cells. Such samples include, but are not limited to, tissue isolated from subjects or animals. Biological samples may also include sections of tissues such as biopsy and autopsy samples, frozen sections taken for histological purposes, blood, plasma, serum, sputum, stool, tears, mucus, hair, and skin. Biological samples also include explants and primary and/or transformed cell cultures derived from patient tissues. A biological sample may be provided by removing a sample of cells from subject, but can also be accomplished by using previously isolated cells (e.g., isolated by another person, at another time, and/or for another purpose), or by performing the methods of the invention in vivo. Archival tissues, such as those having treatment or outcome history may also be used. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. The sample can be obtained by removing a sample of cells from a subject, but can also be accomplished by using previously isolated cells (e.g. isolated by another person), or by performing the methods of the invention in vivo, e.g., using a nanoantenna array as fabricated using the NSL methods as disclosed herein as a probe to measure a target molecule in the body of a subject, e.g., a human subject.

As used herein, the term "polymer" is used in the broad sense and is intended to include a wide range of biocompatible polymers, for example, but not limited to, homopolymers, co-polymers, block polymers, cross-linkable or crosslinked polymers, photoinitiated polymers, chemically initiated polymers, biodegradable polymers, nonbiodegradable polymers, and the like. In other embodiments, the prevascularized construct comprises a polymer matrix that is nonpolymerized, to allow it to be combined with a tissue, organ, or engineered tissue in a liquid or semi-liquid state, for example, by injection. In certain embodiments, the prevascularized construct comprising liquid matrix may polymerize or substantially polymerize "in situ." In certain embodiments, the prevascularized construct is polymerized or substantially polymerized prior to injection. Such injectable compositions are prepared using conventional materials and methods know in the art, including, but not limited to, Knapp et al., Plastic and Reconstr. Surg. 60:389 405, 1977; Fagien, Plastic and Reconstr. Surg. 105:362 73 and 2526 28, 2000; Klein et al., J. Dermatol. Surg. Oncol. 10:519 22, 1984; Klein, J. Amer. Acad. Dermatol. 9:224 28, 1983; Watson et al., Cutis 31:543 46, 1983; Klein, Dermatol. Clin. 19:491 508, 2001; Klein, Pedriat. Dent. 21:449 50, 1999; Skorman, J. Foot Surg. 26:5115, 1987; Burgess, Facial Plast. Surg. 8:176 82, 1992; Laude et al., J. Biomech. Eng. 122:231 35, 2000; Frey et al., J. Urol. 154:812 15, 1995; Rosenblatt et al., Biomaterials 15:985 95, 1994; Griffey et al., J. Biomed. Mater. Res. 58:10 15, 2001; Stenburg et al., Scfand. J. Urol. Nephrol. 33:355 61, 1999; Sclafani et al., Facial Plast. Surg. 16:29 34, 2000; Spira et al., Clin. Plast. Surg. 20:18188, 1993; Ellis et al., Facila Plast. Surg. Clin. North Amer. 9:405 11, 2001; Alster et al., Plastic Reconstr. Surg. 105:2515 28, 2000; and U.S. Pat. Nos. 3,949,073 and 5,709,854.

In certain embodiments, the polymerized or nonpolymerized matrix comprises collagen, including contracted and non-contracted collagen gels, hydrogels comprising, for example, but not limited to, fibrin, alginate, agarose, gelatin, hyaluronate, polyethylene glycol (PEG), dextrans, including dextrans that are suitable for chemical crosslinking, photocrosslinking, or both, albumin, polyacrylamide, polyglycolyic acid, polyvinyl chloride, polyvinyl alcohol, poly(n-vinyl-2-pyrollidone), poly(2-hydroxy ethyl methacrylate), hydrophilic polyurethanes, acrylic derivatives, pluronics, such as polypropylene oxide and polyethylene oxide copolymer, or the like. In certain embodiments, the fibrin or collagen is autologous or allogeneic with respect to the intended recipient. The skilled artisan will appreciate that the matrix may comprise non-degradable materials, for example, but not limited to, expanded polytetrafluoroethylene (ePTFE), polytetrafluoroethylene (PTFE), polyethyleneterephthalate (PET), polyurethane, polyethylene, polycabonate, polystyrene, silicone, and the like, or selectively degradable materials, such as poly (lactic-co-glycolic acid; PLGA), PLA, or PGA. (See also, Middleton et al., Biomaterials 21:2335 2346, 2000; Middleton et al., Medical Plastics and Biomaterials, March/April 1998, at pages 30 37; Handbook of Biodegradable Polymers, Domb, Kost, and Domb, eds., 1997, Harwood Academic Publishers, Australia; Rogalla, Minim. Invasive Surg. Nurs. 11:67 69, 1997; Klein, Facial Plast. Surg. Clin. North Amer. 9:205 18, 2001; Klein et al., J. Dermatol. Surg. Oncol. 11:337 39, 1985; Frey et al., J. Urol. 154:812 15, 1995; Peters et al., J. Biomed. Mater. Res. 43:422 27, 1998; and Kuijpers et al., J. Biomed. Mater. Res. 51:136 45, 2000).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70% or at least about 80%, or at least about 90%, at least about 95%, at least about 97% or at least about 99% or more, or any integer between 70% and 100%.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Nanoantenna Arrays

General

One aspect of the present invention relates to a nanoantenna array. In some embodiments, the nanoantenna array comprises a number of individual nanostructures in a predefined pattern on a substrate. In some embodiments, the nanostructures can exist as individual nanostructures in predefined patterns, or in alternative embodiments, the nanostructures can exist as collections or groups of nanostructures (e.g., an arrangement or coupled nanostructures), where the collections or coupled nanostructures can be in a predefined pattern. In some embodiments, nanoantenna arrays comprise a plurality of nanostructures in a pattern on the surface (e.g., raised) or embedded within (e.g., depressed or in a recess) a support. In some embodiments, the pattern is periodic, and in alternative embodiments, the pattern is non-periodic. In some embodiments, the nanostructures can comprise plasmonic material or a non-plasmonic material, or a combination thereof. In some embodiments, the nanostructures are arranged in a predefined pattern and are a predefined shape for a function of collective excitation and localized plasmon resonance. In particular, a nanoantenna array can comprise plasmonic nanostructures are configured with respect to the surface of the support in a predefined pattern such that the collective resonances modify the quality factor or near-field enhancement properties of the resonance. The nanoantenna array can comprise nanostructures which form a unit cell, where at least one unit cell is arranged in a pattern on the nanoantenna array to form a lattice, wherein light propagating from one unit cells to the next unit cell throughout the array results in a collective resonance on the nanoantenna array that differs from each unit cell's resonance in more than just an additive summing of each unit cell's resonance, wherein the unit cell's resonance results from light propagating from one unit cell to the next unit cell and wherein the light undergoes a fill integer multiple of $2\pi$ phase shift, and wherein the light forms a diffraction order that is evanescent, it does not propagate into the far-field, at wavelengths longer than the corresponding lattice mode and also radiative, it does not propagate into the far-field at wavelengths shorter than the corresponding lattice mode.

One aspect of the present invention relates to nanoantenna arrays comprising a support and nanostructures, e.g., plasmonic nanostructures which are configured to be located in a depression or recess in the support, e.g., embedded within the support. In some embodiments, the nanostructures are arranged in a periodic pattern or a non-periodic pattern or a uniform pattern, such as a lattice, for a function of collective excitation of plasmons and increased plasmon resonance. By definition, as the arrangements of the nanostructures are in a predefined pattern, they are not randomly arranged with respect to each other.

In some embodiments, a nanostructure, e.g., a plasmonic nanostructure is present on the surface of the support of the array, e.g., a raised nanostructure on or attached or affixed to the surface of the array.

In alternative embodiments, a plasmonic nanostructure is below or level (e.g. in the same plane) as the surface of the support of the array, such that the nanostructure is depressed or located in a recess of the support. Such an embodiment where the plasmonic nanostructure is below, or in the same plane as the surface of the support, is referred to herein as a "embedded plasmonic nanostructure". In some embodiments, where the plasmonic nanostructure is embedded below the surface of the surface of the support of the array, there is a void above the embedded plasmonic nanostructure. In alternative embodiments, this void can be optionally filled with a non-wavelength refracting or wavelength permeable material. Accordingly, in some embodiments, where the plasmonic nanostructure is embedded, the void above the plasmonic nanostructure can be filled with a material which is permeable to an incident wavelength.

In some embodiments, plasmonic nanostructures are configured in a periodic uniform pattern, for example, as an infrared plasmonic nanorod antenna array. In some embodiments, the plasmonic nanoantenna arrays are fabricated using novel nanostencil lithography according to the methods and devices described herein.

In some embodiments, a nanoantenna array can comprise any number of nanostructures, for example at least about 10, or at least about 20, or at least about 50, or at least about 100, or at least about 1000, or at least about 2000, or at least about 2000-3000, or at least about 3000-4000, or at least about 2000-5000, or at least about 5000-10,000 nanostructures, or more than 10,000 nanostructures, or any integer between about 10-100, or about 100-1000, or about 1000-5000, or about 5000-10,000 nanostructures on the nanoantenna array. In some embodiments, the nanoantenna array has consistent nanostructure geometry on the array (e.g., all nanostructures on the array are the same shape and dimensions), and in some embodiments, a nanoantenna array does not have consistent nanostructure geometry (e.g., nanostructures on the array can be mixed and variations in the shape and/or dimensions).

In some embodiments, where the surface of the support is about 100 µm×100 µm, there are about $63^2$ (e.g. 3969) nanostructures for a 1.6 µm periodicity, or about $51^2$ (e.g., 2916) for 2.0 µm periodicity.

Support

In some embodiments, the support of the nanoantenna arrays as disclosed herein can comprise any conducting material, a non-conducting material, or a magnetic material. In some embodiments, the support is a conducting material and can comprise silicon. In some embodiments, the support is a non-conducting material, for example, glass, quartz, or calcium fluoride ($CaF_2$). In some embodiments, the supports can be silicon, polymers, calcium fluoride ($CaF_2$), glass, ZnSe, SiN. In some embodiments, the support comprises any one or the combination of material selected from the group consisting of: silicon dioxide, silicon nitride, $MgF_2$, calcium fluoride ($CaF_2$), a polymer, glass, diamond, ZnSe, Germanium, GaAs, quartz or a quartz based microscope slide, or any combination thereof. In some embodiments, the support is the surface of a ATR crystal, e.g., germanium, silicon, or diamond.

In some embodiments, the support is an unconventional substrate, for example, an unconventional substrate is used in the methods of fabricating a nanoantenna array using the nanostencil lithography methods as disclosed herein. An unconventional substrate is one which is sensitive or readily destroyed, for example, readily degraded or destroyed when subject to post-processing methods, such as dry etching and the like. Such unconventional supports include thin films and elastic stretchy films as disclosed herein.

In some embodiments, the support can be selected by one of ordinary skill in the art based on the incident wavelength, e.g., the incident electromagnetic wavelength, as certain materials have strong absorption bands over different wavelengths. For example, if an absorption band of the material to be sensed is in this region, then the material is not suitable for a support material.

In some embodiments, the support is substantially planar. In some embodiments, the support is not planar. In some embodiments the support is a solid support.

Figure 29B:
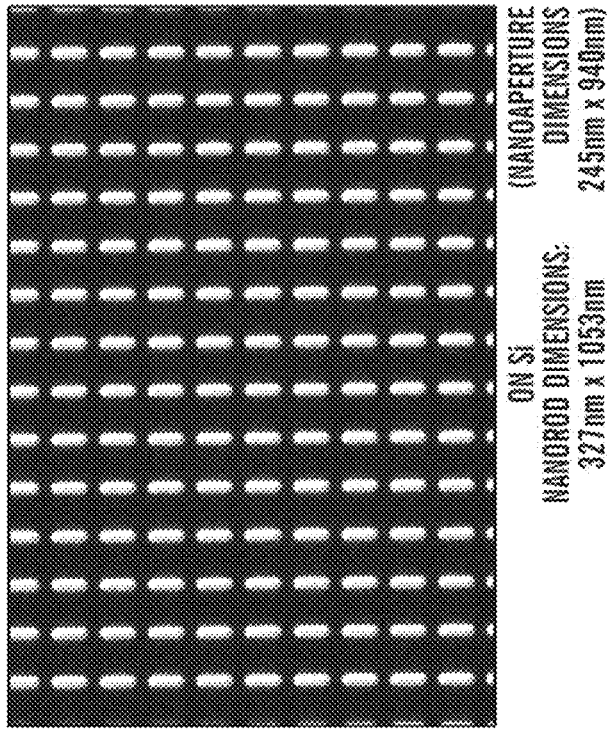
FIG. 29A-29D show embodiments of using the nanostensil lithography (NSL) fabrication to deposit gold nanorods on a PDMS support and a Si support. Using the nanostensil to deposit materials for the nanostructure on different support materials has a significant effect on the resulting particle dimensions. Importantly, the dimensions and shape of the nanostructure generated using the nanostencil lithography (NSL) method is significantly effected by any gap which exists between the stencil and surface of the support. Support made of a material which has a sticky and/or elastic surface helps to minimize the gap. When there is no gap between the nanostensil and the support, the resulting plasmonic nanostructures on support has the identical dimensions and shape as defined by the nanoapertures in the corresponding nanostencil. When a small gap exists between nanostensil and the support (e.g., when using a Si support or any other nonelastic surface such as glass, $CaF_2$) it results in a gap resulting in enlarged nanostructures so that the resulting nanostructure dimensions and size will be larger than the nanoaperture of the nanostencil, and the size of the nanostructure will increase proportional to the larger the gap, so as the gap gets larger, the nanostructures begin to enlarge consistently.
Figure 29A:
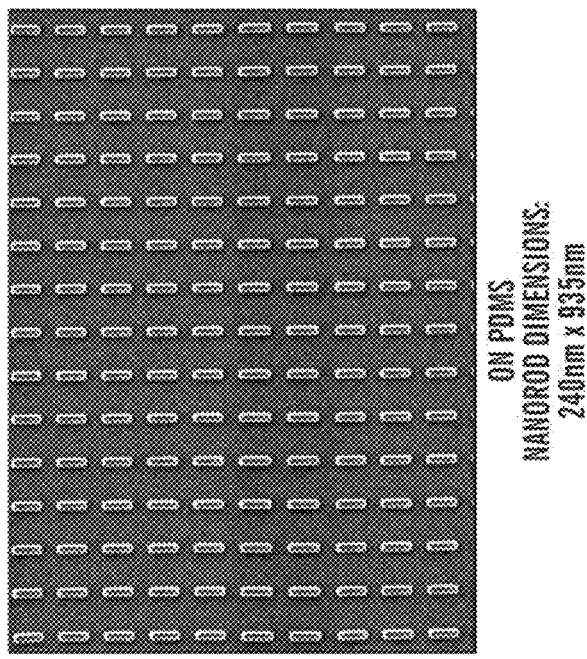
Figure 29D:
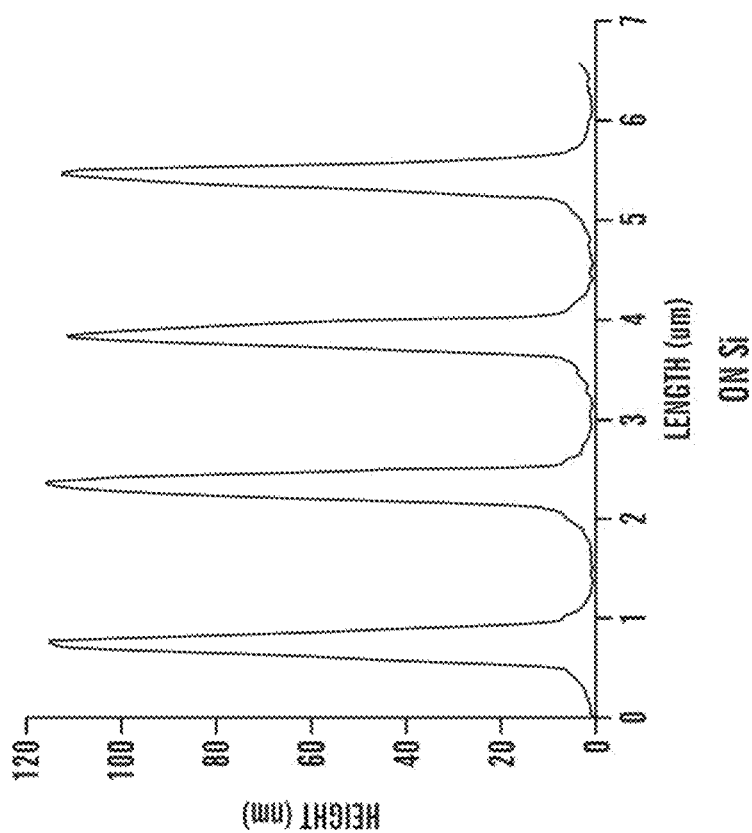
Figure 29C:
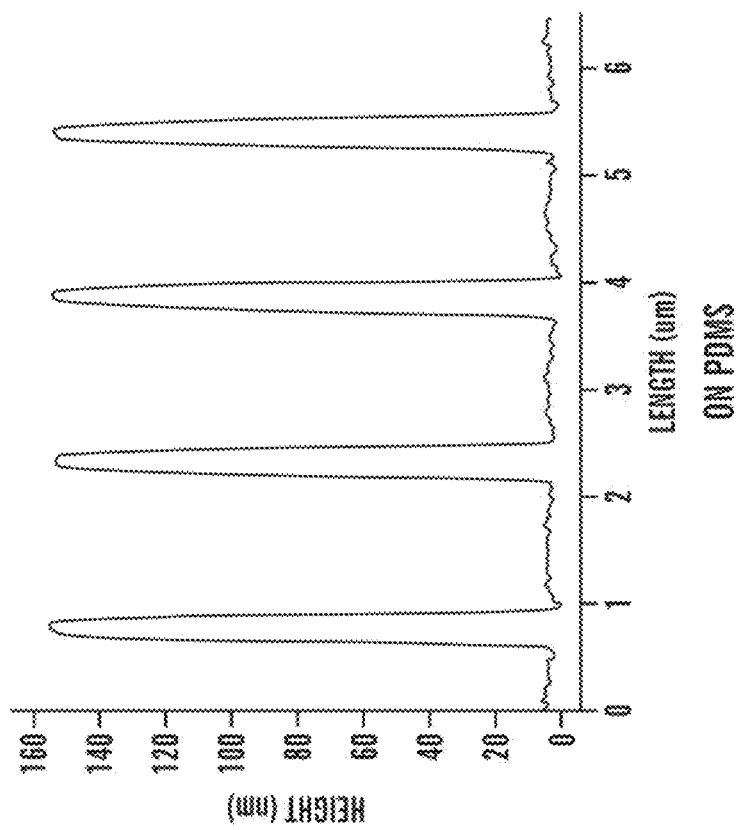

In some embodiments, the support is a non elastic surface, for example, silicon, silicon nitride, silicon dioxide, glass, $CaF_2$ and the like. In alternative embodiments, the support has a sticky and/or elastic surface, for example, PDMS. For example one advantage of using a sticky and/or elastic surface such as PDMS, as shown in FIGS. 29A and 29C, is that when the nanoantenna array is fabricated using the nanostencil lithography fabrication methods as disclosed herein, a support material which comprises a sticky and/or elastic surface such as PDMS prevents particle scattering due to no gap between the nanostencil and the surface of the PDMS support, and therefore results in nanostructures which are virtually identical in dimensions to the predefined nanoapertures of the nanostencil, and also results in consistent reproducible nanostructure shape and geometry across the support surface. In contrast, as shown in FIGS. 29B and 29D, when the support is non-elastic and/or non-sticky, e.g., silicon (Si), when the nanoantenna array is fabricated using the nanostencil lithography fabrication methods, significant particle scattering occurs around each nanostructure due to even a finite or minute gap between the non-elastic support and the nanostencil, resulting in nanostructures which are larger in size than the corresponding nanoaperture of the nanostencil through which the plasmonic material was deposited, and also results in inconstant heights and smaller height of the nanostructure as compared to if an elastic and/or sticky support material (e.g., PDMS) was used.

Figure 25A:
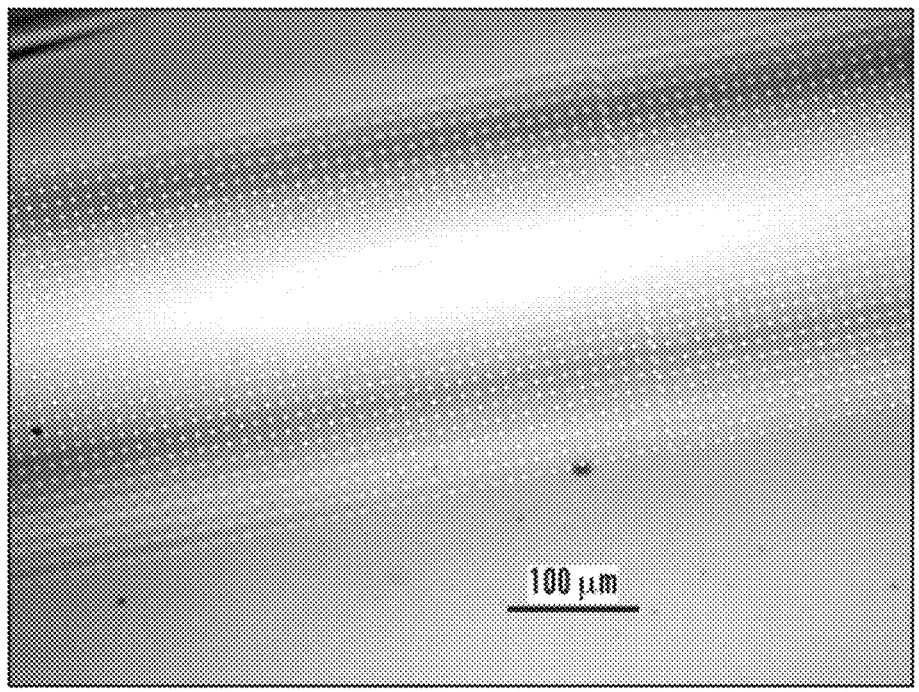
FIGS. 25A-25B show a nanoantenna array wrapped around a curved surface.
Figure 25B:
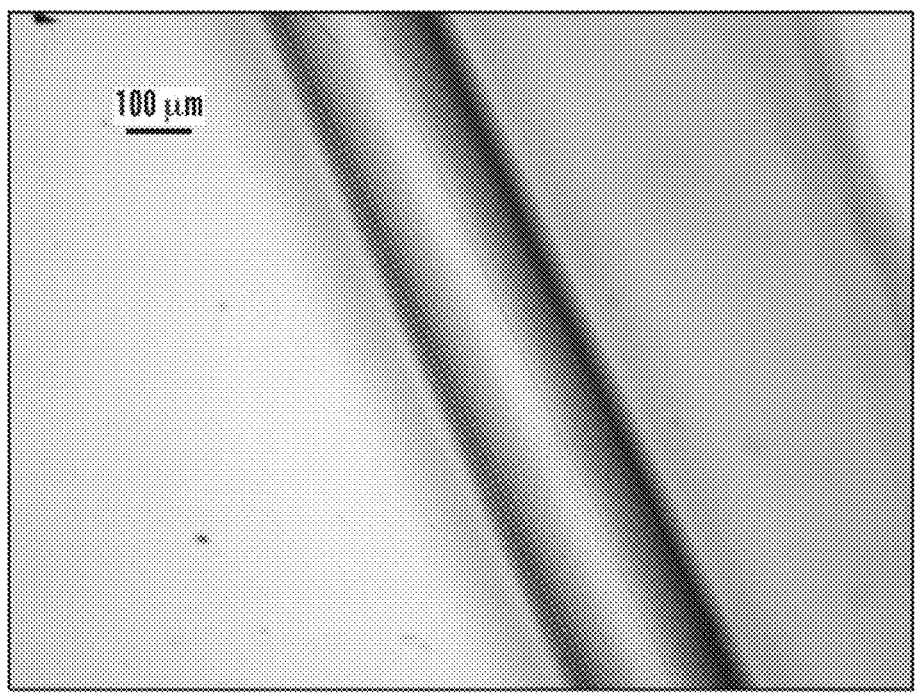

In some embodiments, the support is a flexible support. For example, the flexible support can be flexible enough to enable it to be wrapped around an element, e.g. a curved shape, or fitted into a particular shape or recess. As an example only, as shown in FIG. 25A-25B, the flexible support comprising the nanostructures can be wrapped around the curved surface of a cable, for example a fiber optic cable (e.g. an optical fiber). In some embodiments, the nanostructures are in contact with the element which they are wrapped around, e.g., a fiber optic cable, such that the flexible support is on the outside (e.g., the nanostructures are located between the flexible support and the cable element). In another embodiment, the reverse side of the flexible support (e.g., the side that does not have the nanostructures on) is in direct contact with the element, e.g., cable element, and the nanostructures are on the outside. In some embodiments, the flexible support with the nanostructures can be conformed to be fitted into a predefined shape, e.g., conformed to be fitted on the inside (e.g., lumen) of a tube, or inserted into a hole, or a box or other void or recess of a structural element. In some embodiments, a flexible film is between 0.1-10 µm in thickness, or about between 1-2 µm, or between about 1-5 µm, or between about 5-10 µm, or greater than about 10 µm in thickness, or less than about 1 µm in thickness.

Figure 26A:
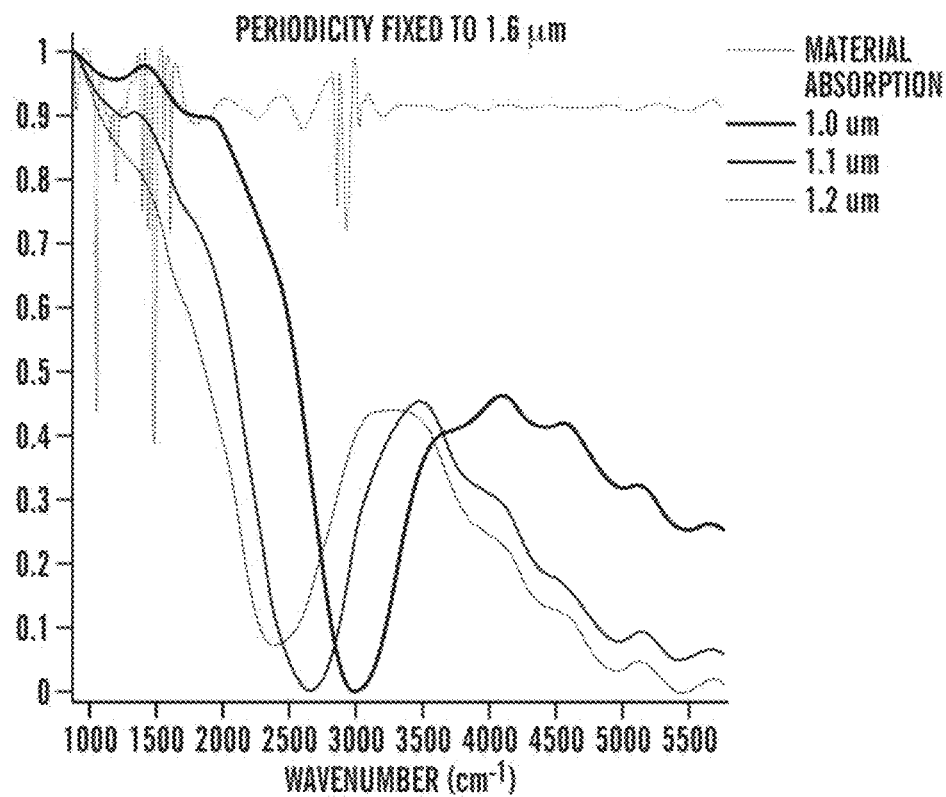
FIG. 26A-26B shows that resonance peak location can be tuned to any desired wavelength by simply changing the predefined pattern (e.g., the periodicity) or the dimensions (e.g., length, width, height etc.) of a plasmonic nanostructure within the array.
Figure 26B:
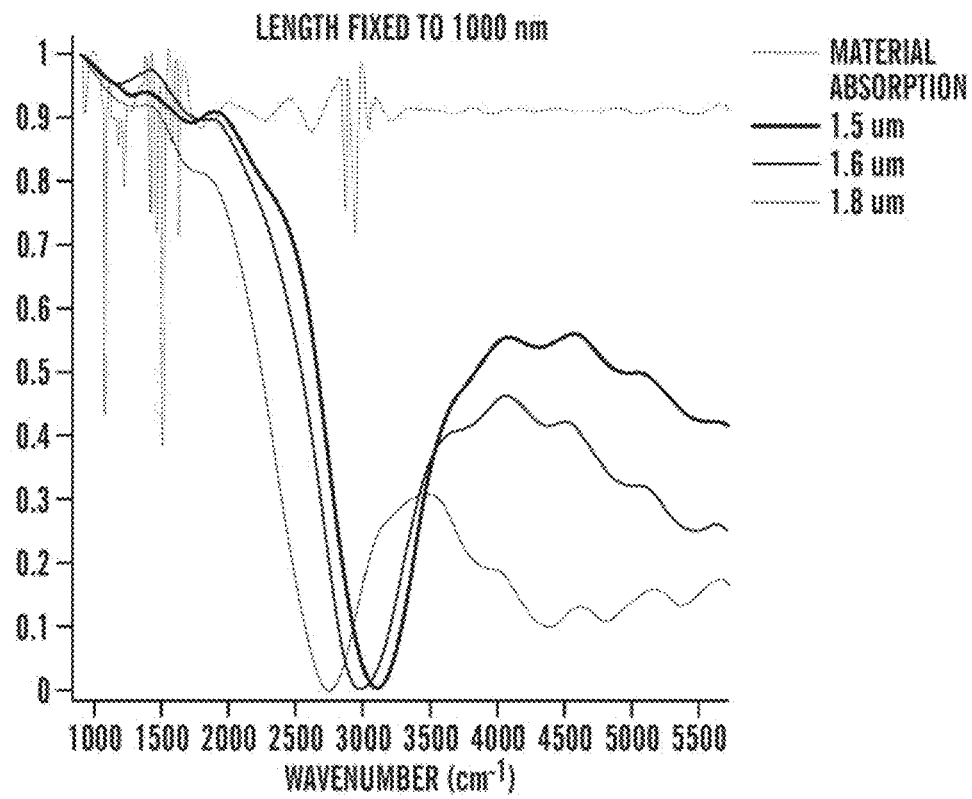
Figure 27A:
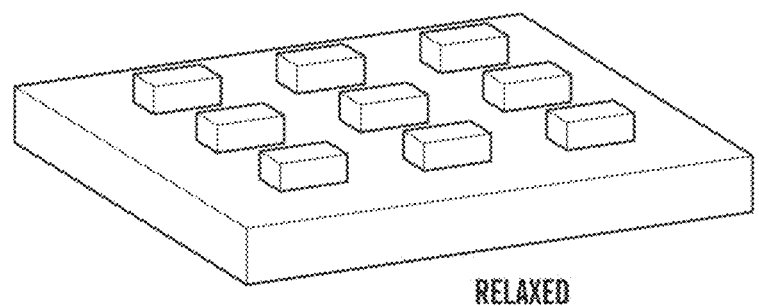
FIG. 27A-27C shows a schematic of active tuning of plasmonic responses.
Figure 27B:
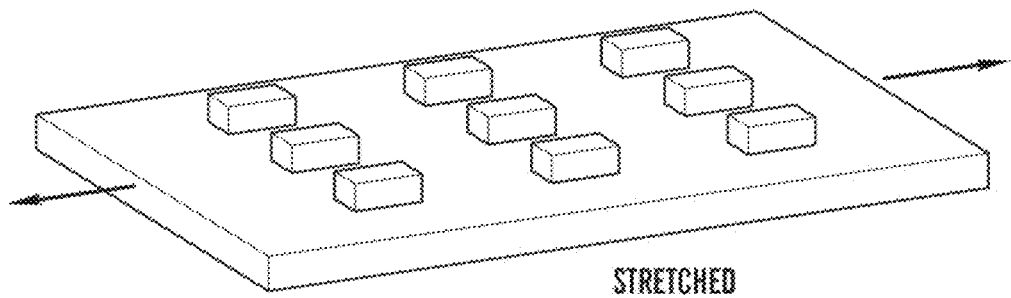
Figure 27C:
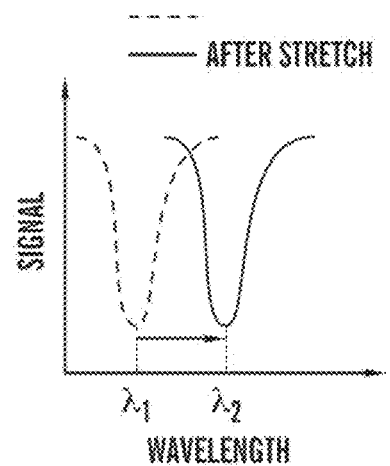
Figure 28A:
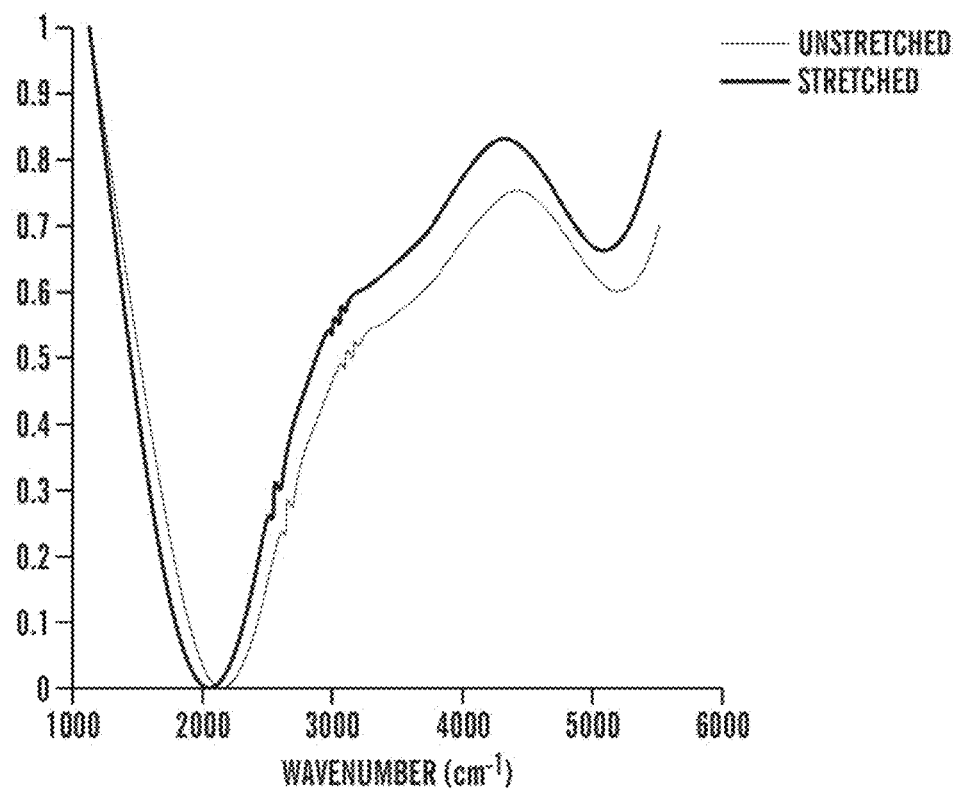
FIG. 28A-28B shows FTIR measurements which demonstrate that where the nanostructures are on a mechanically stretchable elastic thin films, the periodicity of plasmonic nanostructures within the array could be tuned both in x and y dimensions.
Figure 28B:
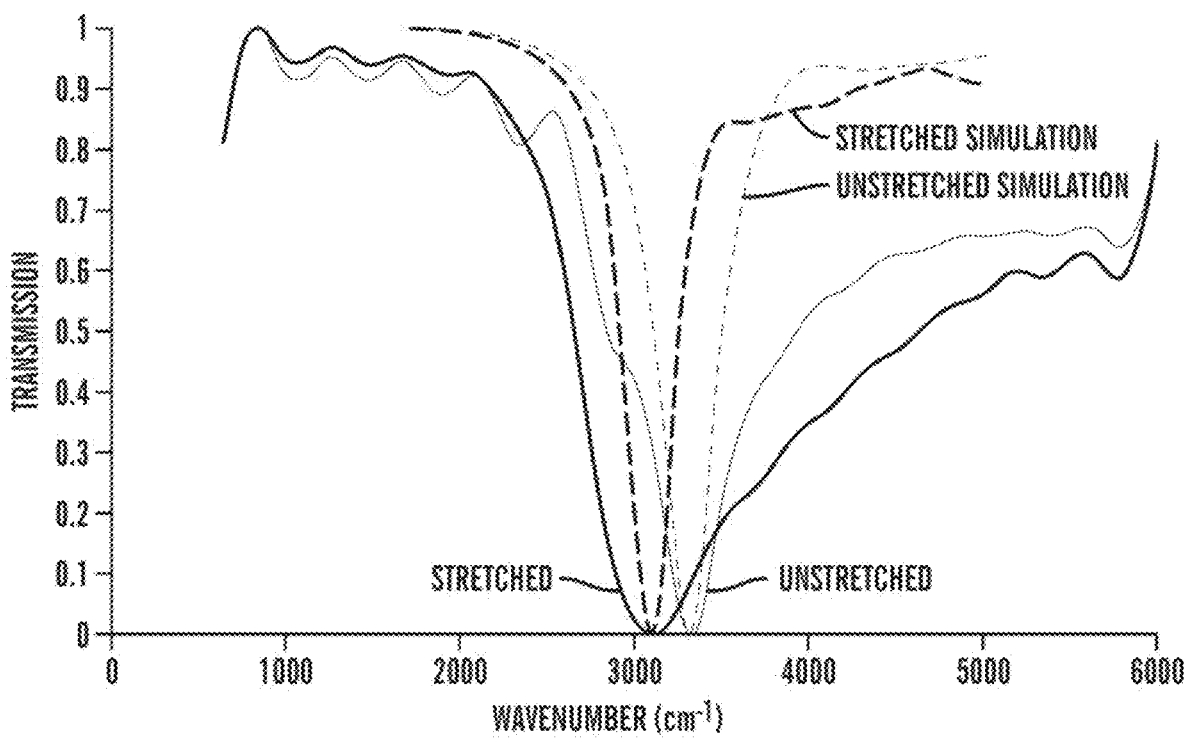

In some embodiments, the support is a thin film, for example, a stretchable elastic thin film. Any stretchable thin film may be used, for example, but not limited to, LDPE film (commonly known as Glad cling wrap), Teflon, partlene C and the like. As shown in FIG. 27A-27B, use of a thin film as the support in a nanoantenna array is advantageous as it allows active tuning of plasmonic responses to particular wavelengths. For example, as shown in FIG. 26A-26B, resonance peak can be tuned to any desired wavelength by simply changing the plasmonic nanostructures dimensions (see FIG. 26A) or by changing the predefined pattern (e.g. periodicity) of the nanostructures within the nanoantenna array (see FIG. 26B). Thus, stretching a nanoantenna array comprising a predefined pattern of nanostructures on a thin-film elastic, stretchable support allows the support to be stretched to alter the periodicity (or the predefined pattern) of the nanostructures in both the x-axis and/or the y-axis and/or nanostructure shape. In some embodiments, the stretchable elastic thin film can be stretched only in an x-axis dimension, or only in a y-axis dimension, or in both an x-axis and a y-axis dimension. In some embodiments, the stretching of the elastic thin film does not alter the dimensions (e.g., the shape or size) of the nanostructures, but only alters the periodicity of the nanostructures with respect to each other (as shown in FIG. 28A). In alternative embodiments however, the stretching of the elastic thin film alters both the dimensions (e.g., the shape and/or size) of the nanostructures as well as the periodicity of the nanostructures with respect to each other.

In some embodiments, the stretchable elastic thin film is about 10-100 nm thick, or about 50-100 nm thick, or about 100 nm-1 µm thick, or about 1-2 µm thick, or any integer between 10 nm and 2 µm thick, or greater than about 2 µm think, for example, about 5 µm thick or greater. In some embodiments, the stretchable elastic thin film is durable enough for stretching multiple times, for example, at least 2, at least 3, at least 4, at least 5, at least 6, at least about 7, or more than 7 times. For instance, in some embodiments, a stretchable elastic thin film support comprising nanostructures can be stretched multiple times to adjust and change the periodicity of the nanostructures on the array for active tuning of the plasmonic responses of the nanostructures to particular wavelengths, for example, to analyze a target molecule at different resonance wavelengths. In some embodiments, the stretchable elastic thin-film can be stretched between about 1%-20% of its original size, for example, about at least 1%, or about 2%, or about 3%, or about 4%, or about 5%, or about 6%, or about 7%, or about 8%, or about 9%, or about 10%, or about 12%, or about 15%, or about 16%, or about 18%, or about 20%, or greater than 20% of its original size, e.g., stretched in its x-axis and/or y-axis. In some embodiments, a stretchable elastic thin-film can be stretched along the plane perpendicular to a nanostructure dimension, for example, perpendicular to a nanorod elongation.

In some embodiments, a support which is a stretchable elastic thin film can be stretched by any means known to persons of ordinary skill in the art. For example, one can mechanically stretch the stretchable elastic thin-film, or alternatively, one can use thermal modifications, such as heating and cooling to expand and shrink the stretchable elastic thin-film respectively.

In some embodiments, the support is generally flat, and can be any geometric or arbitrary shape and can be configures to be any shape for a desired purpose, for example, rectangular, square, triangular, which can be selected in order to meet the desired need. In some embodiments, the support is shaped to be wrapped around an element, e.g., a fiber optic cable and the like, or configures to be fitted in a void or recess in an element, or fitted in inside of a tube etc. In some embodiments, the support has the surface dimensions of about 50 µm×50 µm, or about 100 µm×100 µm, or about 200 µm×200 µm, or about 500 µm×500 µm, or about 100 µm×200 µm, 100 µm×300 µm, 200 µm×300 µm, etc.

Plasmonic Nanostructures

The nanostructures as disclosed herein can comprise plasmonic or non-plasmonic material or a combination thereof. The nanostructures are of a predefined shape and a predefined arrangement with respect to each other to form a predefined pattern to result in optical nanostructures which focus the electromagnetic energy on nanometer scale areas with high spatial and spectral control of the energy concentration. The predefined pattern of the nanostructures are capable of strong enhancement of a number of optical phenomena, such as the extraordinary optical transmittance, Raman scattering, nonlinear photoluminescence, Kerr optical non-linearity, and other important optical effects. The present invention relates to the predefined arrangement of nanostructures in units, where the arrangement of units to form a lattice can be precisely controlled.

Shapes and Geometry of Nanostructures

In some embodiments, the plasmonic nanostructures can have a predefined geometric shape which is smaller than incident wavelength. For example, the shape of a nanostructure, e.g., a nanoantenna for use in the nanoantenna arrays as disclosed herein, determines the volume of molecules which can be detected by the nanoantenna and influences the enhancement of the absorption spectra.

As the predefined shape, predefined size and predefined pattern, (which is, in some instances, a periodic distribution) of the smaller nanostructures diminishes, the resonances shift towards the visible wavelength regime. Nanoantenna arrays comprising small nanostructures can be used to support resonances at visible spectrum, and can be used for non-linear photonic and photovoltaic applications.

In some embodiments, a nanostructure as disclosed herein can be any predefined geometric shape and any geometries commonly known to persons of ordinary skill in the art. In some embodiments, the nanostructures are selected from the group consisting of nanowires, nanorods, nanotriangles and nanodisks, nanosquares and the like. Other geometric conformations of nanostructures are also emcompassed for use in the nanoantenna arrays as disclosed herein, and include without limitation, nanorods, nanorectangles, nanosquares, nanodiscs, nanocircles, nano-ovals, nanotriangles, cross-shapes, nanowires, or irregular shaped nanostructures. In some embodiments, the nanostructure is a cylindrical rod with a cross sectional radius R and hemispherical ends.

In some embodiments, a nanotriangle nanostructure can be any triangular configuration, for example, an equilateral triangle, an isosceles triangle, a rectangular triangle, a special right triangle, an oblique triangle, an obtuse triangle, an acute triangle, a scalene triangle and the like.

In some embodiments, the nanostructures can exist as individual nanostructures in predefined patterns, or in alternative embodiments, the nanostructures can exist as collections or groups of nanostructures (e.g., an arrangement or coupled nanostructures), where the collections or coupled nanostructures can be in a predefined pattern. For example, in some embodiments, one or more nanostructures can be a collection of nanostructures, e.g., a collection in specific arrangement, such as a star, cross, dimer, trimer etc arrangement, and the collection of nanostructures can then be organized into a predefined pattern, e.g., periodic, non-periodic, super-periodic etc. In some embodiments, such arrangements include, but are not limited to at least 2 nanostructures which are closely spaced, for example, coupled together, for example as dimers, trimers etc. A collection of one or more nanostructures can be a symmetrical or asymmetrical configuration of nanostructures, and can also be any pre-defined pattern. In some embodiments, a collection of nanostructures can be a number of nanostructures coupled together, for example, as dimers, trimers or a collection of about 4, or about 5 or about 6, or about 7 or more individual nanostructures. In some embodiments, the nanostructures can be coupled together in parallel, for example, at least 2, or a least 3, or at least 4, or at least 5 or more nanostructures in parallel, for example, nanorods in parallel to one another. In some embodiments, the nanostructures can be coupled together in series, for example, at least 2, or a least 3, or at least 4, or at least 5 or more nanostructures in series, for example, nanorods in series to one another (e.g., one end in close proximity to the end of another nanorod). In some embodiments, the nanostructures are triangular in shape and are form a bow-tie like configuration. In some embodiments, the triangle nanostructures can be in close proximity to one-another at a point of a triangle or along one side of a triangular nanostructure. In some embodiments, nanostructures in a collection can be pointing in the same direction or in opposite directions, or perpendicular with respect to one another.

In some embodiments, nanostructures can be coupled together in a symmetrical configuration. For example, one can configure the nanostructures in any symmetrical configuration know to one of ordinary skill in the art. In some embodiments, a symmetrical configuration of a collection of nanostructures can comprise a number of the same, or different shaped nanostructures which are all in close proximity at a central point, for example, nanostructures which are nanorods can all have one end in close proximity to other nanorods in the collection to form a star shaped structure. Similarly, where all the nanostructures are in close proximity to all the other nanostructures in the parallel, for example, at least 2, or a least 3, or at least 4, or at least 5 or more nanostructures in parallel, for example, nanorods in parallel to one another.

In some embodiments, the upper surface of the nanostructure is substantially planar. In some embodiments the upper surface of the nanostructure is concave or convex. Accordingly, both planar, concave and convex upper surfaces of the nanostructres for both on-surface or embedded nanoparticles is encompassed in the present invention. In some embodiments, the upper surface of the nanostructure is substantially granular or rough. In some embodiments, the upper surface of a nanostructure is corrugated, for example, comprises a series of parallel ridges, furrows or indentations in the upper surface of the nanostructure.

Material of the Nanostructures.

In some embodiments, the plasmonic nanostructures comprise a plasmonic material. In some embodiments, the plasmonic material is a metallic plasmonic material. Such metallic plasmonic materials can be any metal, including but not limited to noble metals, and alloys. Preferred plasmonic materials include Au, Ag, Pt, Cu, Li, Na, K, Al, Pd, and Ni. Plasmonic materials, as described herein, elicit plasmon resonance when excited with electromagnetic energy. In some embodiments, the nanostructure is not a plasmonic material, or a nanostructure can comprise a combination of a plasmonic material and a non-plasmonic material. In some embodiments, the plasmonic materials can be photonic crystals (PhCs), which offer the unique opportunities to tailor the spatial extend of the electromagnetic field and control the strength of the light-matter interaction.

In some embodiments the nanostructures can comprise a combination of plasmonic materials, for example can comprise different layers of plasmonic materials, for example, but by no way a limitation, a nanostructure can be configured from silver, which is layered or encased in a gold layer. Other configurations are encompassed within the scope of the invention, such as alternating layers of at least 1, or at least 2, or at least 3, or at least 4, or at least 5 different plasmonic materials.

Sizes and Dimensions of the Nanostructures.

The dimensions of the nanostructures, e.g., nanoantennas for use in the nanoantenna arrays as disclosed herein are determined by the incident wavelength of interest (e.g., the wavelength of the absorption band of interest the support material.

In some embodiments, the size of the nanostructures, e.g., nanoantennas are about 100 nm in diameter. In embodiments where a nanostructure is a nanorod, the nanostructure is about 800 nm long with a 1.5 µm periodicity. In some embodiments, the nanostructure dimensions, e.g., size is dependent on the incident wavelength which it is to be used. As an illustrative example only, for a nanorod nanostructure to be used for collective resonance for visible/near-infrared a nanorod can be between about 100-1000 nm long, about 50-300 nm wide and about 20-100 nm thick. For example, a nanorod for use with visible/near-infrared wavelengths can be about at least about 70 nm, or about 100 nm, or about 200 nm, or about 300 nm, or about 400 nm, or about 500 nm, or about 600 nm, or about 700 nm, or about 800 nm, or about 900 nm, or about 1000 nm in length, or longer than 1000 nm in length, or any integer between 100-1000 nm in length.

In some embodiments, a nanorod for use with visible/near-infrared wavelengths can be about at least about 30 nm, or about 40 nm, or about 50 nm, or about 60 nm, or about 70 nm, or about 80 nm, or about 90 nm, or about 100 nm, or about 150 nm, or about 200 nm, or about 300 nm in width, or wider than 300 nm, or any integer between about 30-300 nm in width.

In some embodiments, a nanorod for use with visible/near-infrared wavelengths can be about at least about 10 nm, or about 20 nm, or about 30 nm, or about 40 nm, or about 50 nm, or about 60 nm, or about 70 nm, or about 80 nm, or about 90 nm, or about 100 nm, or about 120 nm in height, or taller than 100 nm in height, or any integer between about 10-120 nm in height.

As an illustrative example only, for a nanorod nanostructure to be used for collective resonance for mid-infrared wavelength, a nanorod can be between about 300-3000 nm long, about 50-300 nm wide and about 20-200 nm thick. For example, a nanorod for use with mid-infrared wavelengths can be about at least about 200 nm, or about 300 nm, or about 400 nm, or about 500 nm, or about 600 nm, or about 700 nm, or about 800 nm, or about 900 nm, or about 1000 nm, or about 1500 nm, or about 2000 nm, or about 2500 nm, or about 3000 nm, or about 3500 nm in length, or longer than 3000 nm in length, or any integer between 300-3000 nm in length.

In some embodiments, a nanorod for use with mid-infrared wavelengths can be about at least about 30 nm, or about 40 nm, or about 50 nm, or about 60 nm, or about 70 nm, or about 80 nm, or about 90 nm, or about 100 nm, or about 150 nm, or about 200 nm, or about 300 nm in width, or wider than 300 nm, or any integer between about 30-300 nm in width.

In some embodiments, a nanorod for use with mid-infrared wavelengths can be about at least about 10 nm, or at about 200 nm, or about 30 nm, or about 40 nm, or about 50 nm, or about 60 nm, or about 70 nm, or about 80 nm, or about 90 nm, or about 100 nm, or about 150 nm, or about 200 nm, or about 250 nm in height, or taller than 250 nm in height, or any integer between about 10-200 nm in height.

Figure 23C:
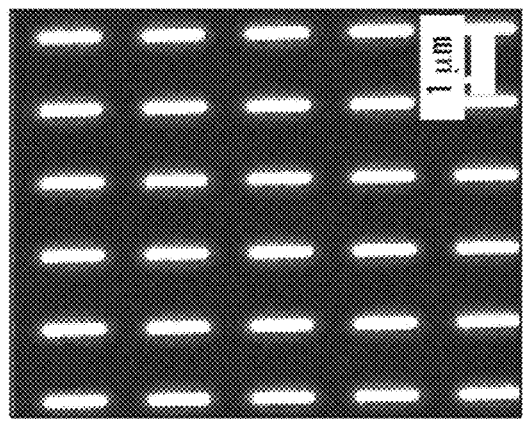
FIGS. 23A-23C show various structures fabricated according to one or more embodiments of the invention.
Figure 23B:
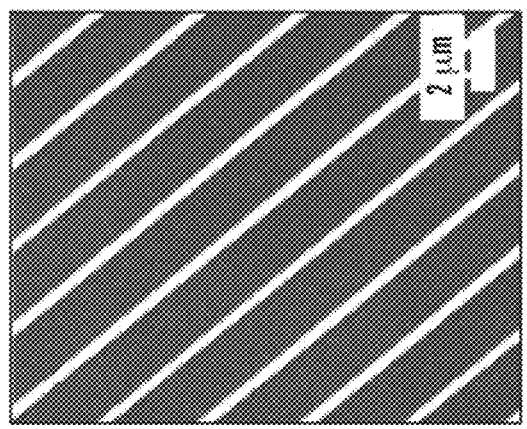
Figure 23A:
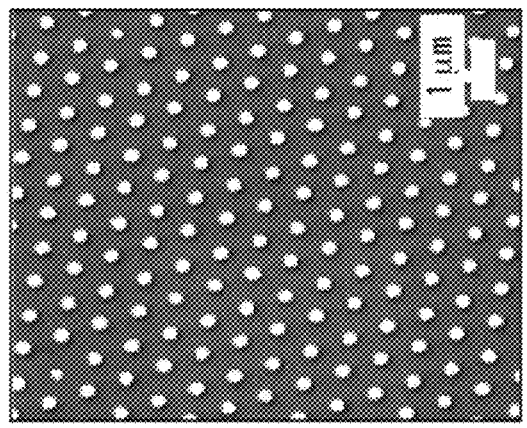
Figure 24A:
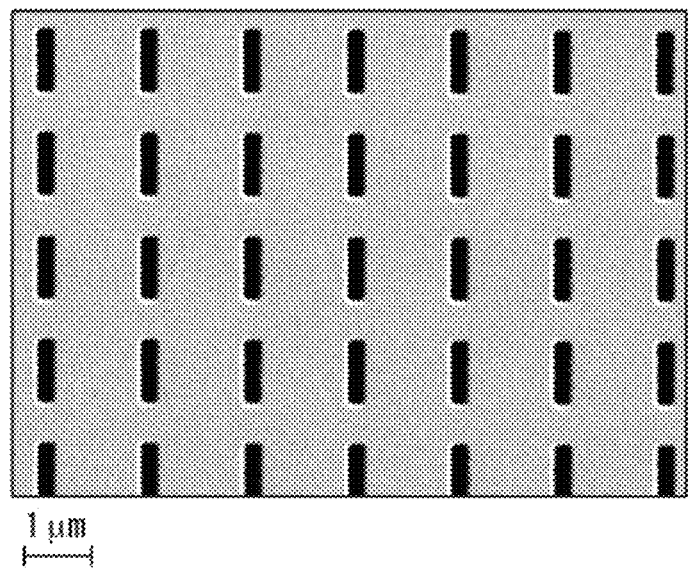
FIGS. 24A-24B show
Figure 24B:
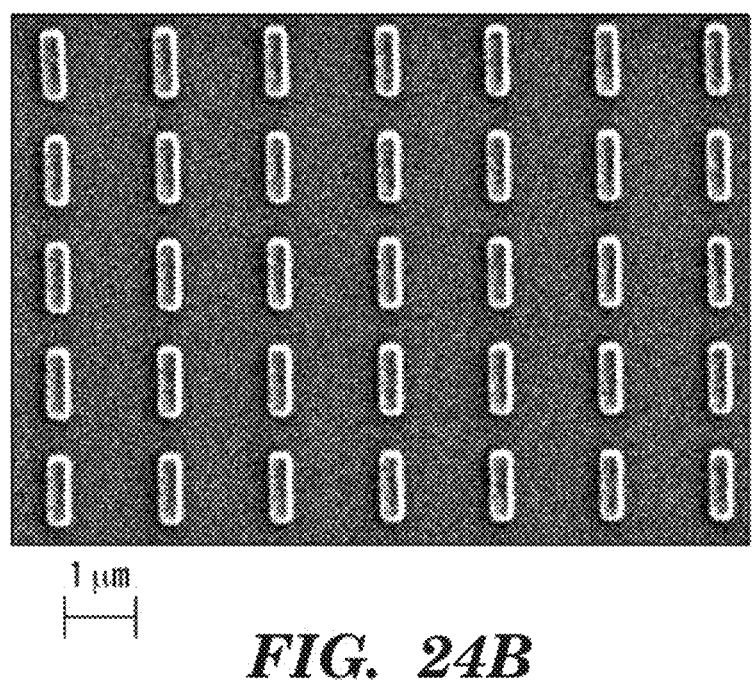

In some embodiments, where a nanostructure is a circle, the nanocircle can be about 200 nm in diameter with a 600 nm periodicity, e.g., 200 nm diameter circular nanostructures present in a lattice, e.g., a triangular lattice (as shown in FIG. 23A). In some embodiments, where the nanostructure is a nanowire, the nanowire can be about 350 nm in width and 50 µm in length.

In some embodiments, the height of a nanostructure, e.g., a nanoantenna either on, or embedded in a support of the nanoantenna array is about between 20 nm and 100 nm in diameter. For example, in some embodiments, where the nanostructure is an on-support nanostructure, the nanostructure height is about 20 nm, or about 40 nm, or about 60 nm, or about 80 nm, or about 100 nm, or greater than about 100 nm. For example, the upper surface of an on-support nanostructure is about 20 nm, or about 40 nm, or about 60 nm, or about 80 nm, or about 100 nm, or greater than about 100 nm above the surface of the support.

In embodiments where the nanostructure is embedded in the support, the nanostructure height is about 20 nm, or about 40 nm, or about 60 nm, or about 80 nm, or about 100 nm, or greater than about 100 nm in height. For embedded nanostructures, the upper surface of the embedded nanostructure can be about 20-1000 nm below the surface of the support, for example, at least about 20 nm, or about 50 nm, or about 100 nm, or about 200 nm, or about 300 nm, or about 400 nm, or about 500 nm, or about 600 nm, or about 700 nm, or about 800 nm, or about 900 nm, or about 1000 nm or greater than about 1000 nm below the surface of the support.

For example, in embodiments where the nanostructure is embedded in the support, the nanostructure is embedded (e.g., depressed) below the surface of the support by about 200 nm, or between about 20-1000 nm, for example, the height of the top of the nanostructure is at least about 20 nm, or about 50 nm, or about 100 nm, or about 200 nm, or about 300 nm, or about 400 nm, or about 500 nm, or about 600 nm, or about 700 nm, or about 800 nm, or about 900 nm, or about 1000 nm or greater than about 1000 nm below the surface of the support.

In some embodiments, the nanostructures are arranged in the same orientation (e.g., for example, if a nanostructure is a nanorod, the nanorod are all parallel with respect to each other). In some embodiments, where the nanostructures are in a collection, e.g., a dipole or bow-tie arrangement of nanotriangles, such a bow-tie arrangement are parallel with respect to other bow-tie arrangements.

Periodicity and Predefined Patterns of the Nanostructures on the Support

A number of nanostructures can be organized or arranged in a predetermined pattern, such as a periodic pattern, or non-random, non-periodic pattern, a semi-periodic pattern or a uniform pattern which is a function which allows for collective excitement of surface plasmons. In some embodiments, the nanostructures are in a predefined pattern which is arranged as a lattice, for example as shown in FIG. 23A, nanodiscs are organized in a triangular lattice. Other lattices are also encompassed, for example, square lattices (first order), triangular, rectangular, hexagonal, octagonal, etc and other lattices known to persons of ordinary skill in the art are also encompassed. In some embodiments, the nanostructures can exist as individual nanostructures in predefined patterns on the substrate of the nanoantenna array, or in alternative embodiments, the nanostructures can exist as collections or groups of nanostructures (e.g., an arrangement or coupling of one or more nanostructures), where the collections or coupled nanostructures can be in a predefined pattern.

Optimal nanostructure geometry (e.g., a predefined shape of the nanostructure) and organization (e.g., a predefined pattern) on the surface of the array determines the high quality factor resonances at the wavelength of the absorption band of interest.

In general, the nanostructures can be arranged in a predefined pattern and are a predefined shape for a function of collective excitation and localized plasmon resonance. In particular, a nanoantenna array can comprise plasmonic nanostructures are configured with respect to the surface of the support in a predefined pattern such that the collective resonances modify the quality factor or near-field enhancement properties of the resonance.

In general, but by no way as a limitation, the size and pattern of the nanostructure on the array are determined such that the nanostructure interacts with electromagnetic radiation in a certain way are determined by the wavelength at which it is intended to be used. If a nanostructure is constructed to work at a wavelength of 600 nm, then the exact same structure will work exactly the same at 1200 nm if the structure is scaled uniformly by a factor of 2. All materials respond to electromagnetic radiation slightly differently depending on the wavelength of the radiation (dispersion). However, for materials where this variation is not particularly large, the trend holds quite well and is commonly used in the design of photonic crystal (or photonic bandgap) structures. Thus due to fact, the periodicity for the nanostructures is better described as a function of wavelength of electromagnetic radiation ($\lambda$), rather than in absolute units, especially when we envision applications to Raman scattering which may use wavelengths in the near-infrared or visible (around 1000 nm) and Infrared absorption spectroscopy which general focuses on wavelengths around 6000 nm.

Accordingly, in some embodiments, periodicity can be between $\lambda/4$-$5\lambda$ for a large periodicity range, and $\lambda/2$-$2\lambda$ for a smaller periodicity range. The symbol 2 here refers to the wavelength of electromagnetic radiation in the support material or the material above (e.g. air or water if the structures are immersed in solution) or material coating the nanostructures structures (e.g., if a polymer film was spun on top of the nanoantenna array. Alternatively, in some embodiments, the periodicity is between 500-1500 nm, for example, which is useful for Raman scattering, and between 1000-10,000 nm, which is useful for surface enhanced infrared absorption spectroscopy, as disclosed herein in the Examples, where optimal periodicity for surface enhanced infrared absorption spectroscopy was 1600 nm.

Additionally, in some embodiments, the nanostructures can be arranged in a pattern which is a periodic pattern. In some embodiments, the periodic pattern has a 1.6 µm periodicity, for example as shown in FIG. 14. In some embodiments, nanostructures are arranged with a periodicity of about between 1.2 µm and about 2.2 µm. In some embodiments, nanostructures are organized at a periodicity of about 1.2 µm, or about 1.3 µm, or about 1.4 µm, or about 1.5 µm, or about 1.6 µm, or about 1.7 µm, or about 1.8 µm, or about 1.9 µm and about 2.0 µm. In some embodiments, where the nanostructure is an on-surface or embedded nanostructure on a silicon support, the plurality of nanostructures has a periodicity of about of about 1.5 µm, or about 1.6 µm.

In some embodiments, the pattern of the nanostructures are in a super-periodic pattern, for example, two levels of periodicity.

In some embodiments, the nanoantenna array can comprise nanostructures which form a unit cell, where at least one unit cell is arranged in a pattern on the nanoantenna array to form a lattice, wherein light propagating from one unit cells to the next unit cell throughout the array results in a collective resonance on the nanoantenna array that differs from each unit cell's resonance in more than just an additive summing of each unit cell's resonance, wherein the unit cell's resonance results from light propagating from one unit cell to the next unit cell and wherein the light undergoes a fill integer multiple of $2\pi$ phase shift, and wherein the light forms a diffraction order that is evanescent, it does not propagate into the far-field, at wavelengths longer than the corresponding lattice mode and also radiative, it does not propagate into the far-field at wavelengths shorter than the corresponding lattice mode.

One method for determining the predefined arrangement or pattern on the nanoantenna array support follows a two step process.

Firstly, the predefined shape or geometry of individual nanostructure is determined or designed such that the nanostructure by itself supports a resonance at the absorption band of interest. In general, in the infrared, for the nanostructure shapes mentioned, the nanostructure size can be varied such that $\lambda = 2n_{eff} L + C$ where $\lambda$ is the wavelength of the absorption band of interest and $n_{eff}$ is an effective refractive index that is strongly dependent on the refractive index of the support material used.

L in the equation can be taken as the length of a rod shaped particle, the diameter for a disc, or the long dimension (i.e. height) of a triangle. Typically, preliminary measurements are used to determine $n_{eff}$ for a specific particle/support combination.

Secondly, the arrangement of individual nanostructures are organized with respect to each other into a predefined pattern on the array. In some embodiments, the predefined pattern is a periodic pattern which is used as a function to enhance the quality factor of the particle resonance. This increases the degree to which the signal from the absorption band of interest is increased.

To arrange the nanostructures into a predefined periodic pattern, the predefined array periodicity can be selected such that d=kin where n is the refractive index of the support material used and 2 is the wavelength of the absorption band of interest (and resonance of the individual nanostructure or nanoparticle). In this embodiment, this is described for a square lattice ($1^{st}$ order), other lattices will follow slightly different equations.

Calculations to Determine the Positioning of the Plasmonic Nanostructures on the Support In some embodiments, the nanoantenna array as disclosed herein comprises plasmonic nanostructures are configured or arranged on-, or embedded within, the surface of the support in a predefined pattern such that diffractive coupling or collective resonances can be used to modify the quality factor or near-field enhancement properties of the resonance.

For example, diffractive coupling or collective resonances description is as follows:

An arrangement of nanoparticles in a predefined pattern can be thought of as a nanostructure in a unit cell, where one unit cell comprises at least two nanostructures and two or more unit cells join to form a lattice. The nanostructures which belong to more than one unit cell, e.g., are a connecting point of a lattice are called lattice points or unit modes, and govern the repetition of the unit cell. The unit cell may consist of a single nanoparticle or an aggregate of 2 or more nanoparticles. The unit cell will support a set of resonances or plasmonic modes occurring at specific wavelengths.

The lattice itself will also support modes (lattice modes). These modes occur when light propagating from one unit cell to the next along an integer combination of the lattice vectors undergoes a full (integer multiple of $2\pi$) phase shift. These modes are commonly associated with diffraction orders of a periodic lattice, that is, they are the wavelengths at which a new diffraction order appears. More specifically, this diffraction order is evanescent (it does not propagate into the far-field) at wavelengths larger than the corresponding lattice mode and radiative (it does propagate into the far-field) at wavelengths that are shorter.

For an array of unit cells arranged in a particular lattice, the resonances of the particle array (plurality of nanoparticles) resulting from the interactions of the unit cell resonances and lattice modes constitute the collective resonances of the particle array. Controlling the position of the lattice mode in relation to the unit cell resonance allows one to obtain collective array resonances that differ significantly from the unit cell resonances (i.e. the collective resonance is not just a sum of unit cell resonances). For example, if the unit cell resonance lies in close proximity to, but slightly to the long wavelength side of the lattice mode, radiation damping can be significantly reduced and higher quality factor resonances (with larger electromagnetic near-field enhancements) can be obtained. If the unit cell resonance lies in close proximity to, but slightly to the short wavelength side of the lattice mode, then the radiation damping will be increased.

The control and engineering of the interaction between the diffractive lattice modes and the unit cell resonances to obtain desired properties of a nanoparticle array (plurality of nanoparticles) constitutes the diffractive coupling/collective resonance engineering.

Dipole Interaction Matrix.

As discussed in the Examples section herein, in an array, each plasmonic nanostructure, e.g., a nanoantenna such as a nanorod responds not only to the incident electromagnetic field, but also to the scattered fields from the other nanorods. Within the discrete dipole approximation, the local field experienced by the $i^{th}$ nanorod is then $$E_{inc,i} + \sum_{i \neq j} \vec{A}_{ij} \cdot \vec{P}_j, \quad (1)$$

with the full dipole interaction matrix, $\vec{A}_{ij}$, given as:

$$\vec{A}_{ij} \cdot \vec{P}_j = k^2 e^{ikr_{ij}} \frac{(\vec{r}_{ij} \times \vec{P}_j) \times \vec{r}_{ij}}{r_{ij}^3} + e^{ikr_{ij}}(1 - ikr_{ij}) \frac{3\vec{r}_{ij}(\vec{r}_{ij} \cdot \vec{P}_j) - r_{ij}^2 \vec{P}_j}{r_{ij}^5}. \quad (2)$$

Here, $\vec{r}_{ij}$ is the position vector from the $j^{th}$ to $i^{th}$ nanorod in the array, and $P_j$ is the induced polarization at the $j^{th}$ rod. For separations more than few tens of nanometers, the first term corresponding to long-range interactions becomes dominant. Accordingly, Eq. (1) can be recast in a form:

$$\sum_{i \neq j} \vec{A}_{ij} \cdot \vec{P}_j = \sum_{i \neq j} \vec{c}_{ij} \cdot \vec{P}_j e^{i\vec{k}\vec{r}_{ij}}, \quad (3)$$

where the long range interaction matrix, $c_{ij}$, is defined as:

$$\vec{c}_{ij} = k^2 e^{ikr_{ij}} \frac{(\vec{r}_{ij} \times \vec{P}_j) \times \vec{r}_{ij}}{r_{ij}^3}. \quad (4)$$

The phase term $e^{i\vec{k}\vec{r}_{ij}}$ is explicitly emphasized in Eq. (3) to highlight the importance of the phase terms of the scattered fields in Eq. (1). (Zou et al., (2004). J. Chem. Phys. 120: 10871-10875.)

Individual Antenna Response Through Randomization.

Figure 9A:
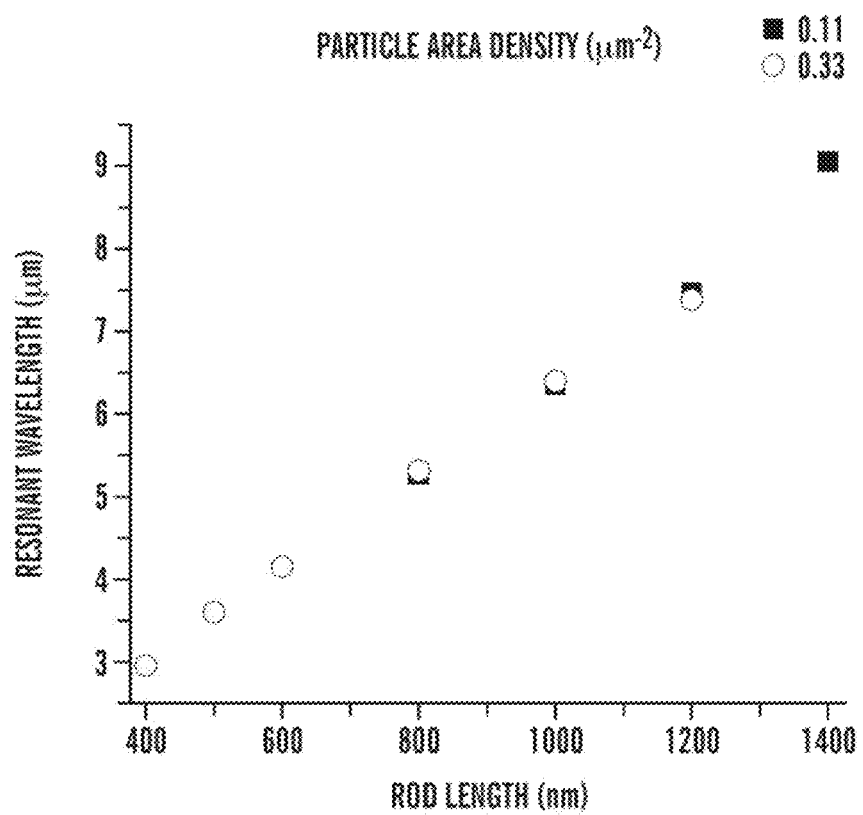
FIGS. 9A-9C shows examples of nanostructure dimensions.
Figure 9B:
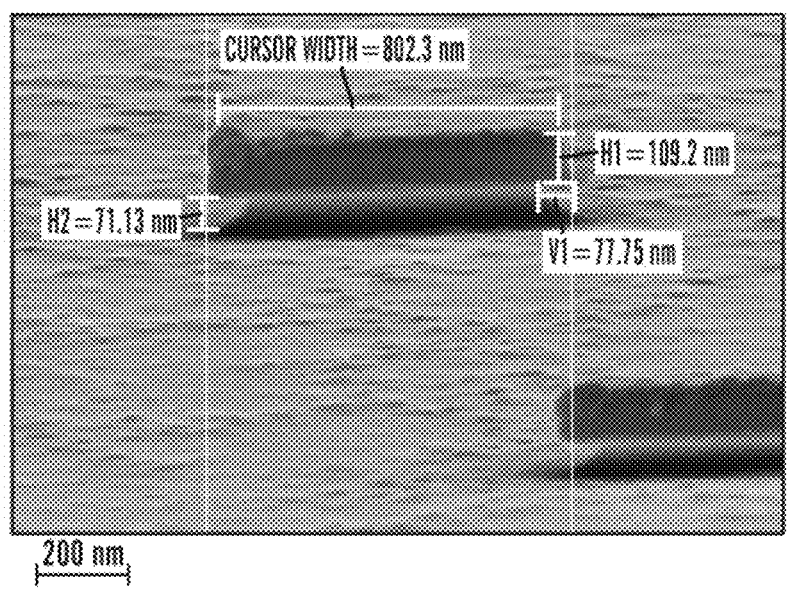
Figure 9C:
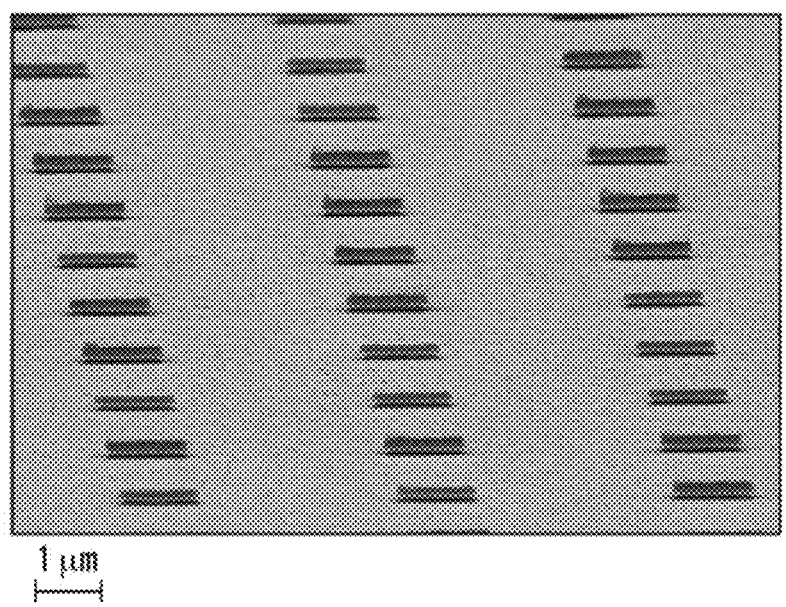

The response of an isolated nano-antenna, in the absence of coupling due to others, is obtained by measuring the signal from an array where the rods are arranged randomly over an 100×100 µm² area. Arrays are designed for a specific antenna density (1 antenna per 4 µm²) and the coordinates of each antenna are chosen randomly from a uniform distribution. An additional constraint is imposed such that the edges of the antennas are never closer than 200 nm. The purpose and the effect of this constraint is two-fold. First, it simply ensures that fabrication can be carried out properly, and all the antennas are well formed and separated. Secondly, this separation prevents any strong near-field coupling which decays rapidly with distance as given in Eq. (1) and Eq. (2). The lack of any long-range order in the array removes any collective resonances due to the inconsistent phase delays for radiation propagating among the nanoantennas. The signal measured from such a random array should therefore be an accurate representation of an individual antenna response. This was confirmed herein by experimentally examining the response of different random arrangements and densities of the antennas. FIG. 9 demonstrates the dependence of the resonant wavelength on rod length for a number of randomized arrays. The random arrangements for each sample were generated independently; therefore both the positions and the lengths of the rods in each array vary. In addition, the variation in the resonant wavelength with the rod length was also measured for two different antenna densities: 1 rod per 1.75×1.75 µm² region (0.33 µm⁻², red circles) and 1 rod per 3×3 µm² (0.11 µm⁻², black squares). The resonance positions (circles and squares) exhibits a clear linear dependence on rod length as predicted by the theory of an individual antenna. For different nanorod density with the same length, negligible variation in resonance wavelength is observed. It is therefore evident that the resonance properties of the random arrays are solely dependent on those of the individual nanorods and accurately represent the isolated antenna behavior.

Enhancement factor calculations are performed by comparing the expected difference signal ($\Delta R/R_0$) obtained from a 2 nm thick silk film on bare silicon to the experimentally measured one (6.8%) from the 2 nm silk coated nanoantenna arrays. In addition, we take into account that the observed enhanced signal is due to the molecules present within the detection volume at the close vicinity of the nanorod tips. The 1.6 µm array contains 63² rods. For each rod, the active area with intense near-fields is approximately 2(h)(w), where h and w are the height (70 nm) and the width (230 nm) of the nanorods, respectively. Herein, since the proteins are coated on the antenna surfaces by physisorbtion (as oppose to chemsorption), the inventors have to take into account the profile of the protein coverage on the sidewalls. For 2 nm thick films, if we assume there is minimal coverage on the sidewalls, the fraction of the active area for an array (with 63² antennas) to the total incident beam with a 100×100 µm² spot size is around $3.7×10^{-4}$. Accordingly, scaling the ratio of our measured signal to the expected reflectance signal (calculated as discussed in the text) with the area factor yields an enhancement factor of 396,700. At the lower limit, if we assume that the entire sidewalls are covered with the protein film (which is not very likely to occur), the enhancement factor is 11,350. Therefore, the enhancement factor is expected to be within the range of $10^4$-$10^5$. In contrast, the random array (containing 51² antennas) gives only 0.9% absoprtion signal (as shown in FIG. 4) and has nearly an order of magnitude weaker enhancement factor compared to the optimized structure.

Molecular sensitivity of our plasmonic platform is calculated by assuming a constant density for the protein molecules within the detection volume—2(t)(h)(w)N², where t is the film thickness (2 nm) and N² is the number of the rods in the array. Because the physisorbed molecules are randomly oriented with respect to the surface of the nanorods, not all the molecules will contribute to the enhanced absorption signal equally. Within a first order approximation (Fermi's Golden rule), the average absoption rate of the electromagnetic energy by the molecular dipoles can be calculated as:

$$\langle S_{fi}(r,\omega) \rangle = \langle (2\pi/\hbar)|\langle f|H(r,\omega)|i\rangle|^2 \delta(\hbar\omega - \varepsilon_f + \varepsilon_i)\rangle, \quad (5)$$

where $\varepsilon_i$ and $\varepsilon_f$ are the energies of the molecular vibrations of the initial $|i\rangle$ and the final $|f\rangle$ states, respectively. The Hamiltonian H, describing the interaction of the electromagnetic field and the molecular dipoles, can be approximated as:

$$|\langle f|H(r,\omega)|i\rangle|^2 = |\langle f|\vec{d}(r,\omega)\cdot\vec{E}(r,\omega)|i\rangle|^2 \approx C|\langle f|d(\omega)E(\omega)|i\rangle|^2 \cos^2(\theta,\phi), \quad (6)$$

where d is the molecular transition dipole moment and C is an averaged constant due to the finite decay length of the enhanced near-fields. Accordingly, the average absorption rate (defined in Eq. (3)) is proportional to the mean squared cosine average of the solid angle between the electric field polarization and the transition dipole moment. For a randomly oriented protein film:

$$\langle \cos(\theta,\phi)^2 \rangle = (1/4\pi) \int_0^{2\pi} \int_0^{\pi} \cos^2\theta \sin\theta\, d\theta\, d\phi = 1/3 \quad (7)$$

Hence, the observed signal is only the one third of the total signal of the molecules within the detection volume. Considering these effects, for silk protein with a molecular mass of M=375 kDa (Sashina et al., (2006) Russion J. Applied Chem. 79:869-876.), and a density D=1.4 g/cm³ (Warwicker J O (1954), Acta Crystal 7:565-571), the difference signal of 6.8% is obtained form $2(t)(h)(w)(N^2)(g)/(3M)=0.3×10^{-18}$ moles. This corresponds to the detection of 300 zepto-moles of proteins for the entire array and only 145 molecules per antenna. Considering the large signal to noise ratios, the molecular sensitivities are down to about a few tens of zeptomoles.

Near Field Mapping.

The large signal enhancement resulting from the enhanced near-fields due to the nanorod resonances are expected to taper off with increasing silk film thickness due to the decaying of the electric fields away from the nanorod tips. This effect is observed in our measurements by varying silk film thicknesses as in FIG. 6B where the difference signal versus film thickness is plotted. For a film of thickness t<<λ, reflectance signal is approximated to be $R_{Film}=R_{Si}\exp(-2\alpha t) \approx R_{Si}(1-2\alpha t)$ after neglecting the surface reflections. Therefore, reflectance difference ($\Delta R = R_{Si} - R_{Film} \approx 2R_{Si}\alpha t$) is expected to follow a linear dependence in the absence of near-field enhancement. The rapid initial increase in the signal with thin film thickness and subsequent saturation of the signal for the thicker films is in contrast to this linear dependence. This observation demonstrates the surface nature of the CEIRA effect.

Stated another way, the plasmonic behavior of nanostructures arranged in a predefined pattern which is a periodic pattern strongly differs from that of the individual constituent nanoparticles. This phenomenon can be understood from fundamental principles by using a coupled dipole (CD) method. For an individual nanoparticle, the acting field is simply the incident field exciting the LSPRs ($E_{act}=E_{inc}$). A nanoparticle responds to this electric field with an induced dipole moment, $p=\alpha_p E_{act}$. In an ensemble, on the other hand, the acting field on the individual particle includes both (i) the incident field and (ii) the sum of the retarded dipolar fields due to the other nanoparticles [0, 0-21]:

$$E_{act,i} = E_{inc,i} + \sum_{\substack{j \neq i \\ j=1}}^{N} e^{ikr_{ij}} C_{ij} p_j \qquad (8)$$

where, $C_{ij}$ is the dipolar interaction matrix without the phase term [0]. The indices i and j label the $i_{th}$ and $j_{th}$ particles, $r_{ij}$ is the distance between them, and N is the total number of particles. The sum in Eq. (8) strongly depends on the phase delay experienced by the retarded dipolar interactions among particles. For a periodically arranged nanoparticle array, the scattered fields add in phase at a specific wavelength when $kr_{ij}=2\pi m$, where m is an integer. This corresponds to the appearance of a new grating order. For wavelengths shorter/longer than this transition wavelength, the grating order is radiative/evanescent. Interesting physical phenomena leading to the narrowing of the plasmonic resonances and the enhanced near-fields are observed around the transition wavelength. A quantitative understanding of the phenomena can be developed for an infinite chain of identical nanoparticles excited by normally incident light. In this case, dipolar moments of the constituent particles are the same $p_j=p_i=\alpha_p E_{act,i}$ and Eq. (8) can be simplified to:

$$E_{act,i} = E_{inc,i} + \underbrace{\left( \sum_{\substack{j \neq i \\ j=1}}^{N} e^{ikr_{ij}} C_{ij} \right)}_{S} \alpha_p E_{act,i} \qquad (9)$$

Following this relation, local electric field can be expressed as $E_{act,i}=(1-\alpha_p S)^{-1} E_{inc,i}$, where S is the retarded dipole sum defined in the parentheses in Eq. (9). Accordingly, an effective polarizability for nanoparticles can be defined as:

$$\alpha_{eff} = \frac{1}{1/\alpha_p - S}. \qquad (10)$$

such that $p_i=\alpha_p E_{act,i}=\alpha_{eff} E_{inc,i}$. This equation shows that the polarizabilities of the nanoparticles in an ensemble are controlled by the retarded dipole sum S, which is only a function of geometrical parameters. A maximum both in the imaginary part and modulus of the particle's complex polarizability, thus a peak in extinction spectrum corresponding to the array resonance, is expected when the real part of the denominator ($1/\alpha_p-S$) vanishes. Creation of collective resonances can be explained using Eq. (10) for an infinite chain of nanorod particles with dimensions chosen to reflect the conditions of our experiments to be discussed below.

Active Optimization of Degree of Spectral Enhancement by the Nanoantenna Array

The spatial arrangement of nanostructures can be optimized for different incident wavelengths and to optimize signal:noise ratio. For example, signal to noise ratio is optimized by altering the spatial configuration and the geometries of the nanostructures, and will in turn determine the degree of enhancement of the absorption band of interest, and the size of the array.

In some embodiments, degree of enhancement depends on particle resonance and therefore could be tuned actively (i.e. during the course of a measurement) by tuning the support refractive index. For example, one could tune support refractive index using any, or a combination of the following, electrically, optically, mechanically and thermally. Additionally, in some embodiments one could also actively tune the degree of enhancement by altering the angle of incident wavelength. For example, one could adjust the angle of the incident wavelength during the course of the measurement to slightly shift the resonance position.

The processes and techniques as described herein have been validated optically with the infrared nanorod antenna arrays, which support collective plasmon resonances. These plasmonic excitations, leading to spectrally narrow far-field extinction resonances and strong near-field enhancements, are extremely important for surface enhanced spectroscopy methods. The fabrication techniques described herein are general and can be adapted to fabricate a wide range of engineered nanoplasmonic devices. The presented methods can be revolutionary for the advancement of nanoplasmonics by enormously increasing throughput and reducing cost and complexity.

Method of Fabrication of Plasmonic Nanostructures and Nanoantenna Arrays

In some embodiments, the nanoantenna arrays as disclosed herein can be fabricated by any means know to one of ordinary skill in the art, for example, but not limited to, electron beam lithography, nanostencil lithography, nanoimprint lithography, interference lithography and UV/DUV lithography (e.g., standard semiconductor industry tool).

In some embodiments, the present invention relates to a method for high-throughput and high resolution nanofabrication to fabricate a nanoantenna array as disclosed herein. In some embodiments, the method involves the use of a nanostencil. In some embodiments, the nanostencil lithography method (NSL) and nanostencil device as disclosed herein can be used to fabricate any nanostructure array, for example, where the nanostructures can be a plasmonic nanostructure, or a non-plasmonic nanostructure.

For example, where the nanostencil lithography (NSL) method and nanostencil device as disclosed herein are used to fabricate a nanoantenna array comprising non-plasmonic nanostructures, the nanostencil can be used to deposit non-plasmonic nanostructures which comprise a biomaterial, regrowth agents for other materials and the like. Other non-plasmonic materials can also be deposited, including but not limited to, dielectric matter such as silicon, silicon dioxide, silicon nitride (SiN), amorphous dielectric matter, magnetic material, e.g., iron, ferrimagnetic materials such as ferrites, magnetite and lodestone, or other material that produces a magnetic field. Other magnetic materials include iron ore (magnetite or lodestone), cobalt and nickel, as well the rare earth metals gadolinium and dysprosium, iron oxide, barium/strontium carbonate ceramic, and Neodymium-iron-boron (NIB) magnetic materials.

In some embodiments, the nanostencil lithography (NSL) fabrication methods as disclosed herein can be used for fabricating nanoantenna arrays comprising non-plasmonic materials, such as, but not limited to, viruses, pathogens, prions, bioanalytes, cells, proteins, nucleic acids, (e.g., DNA, RNA, RNAi, miRNA, and natural antisense nucleic acids (NATs), modified mRNA and RNAi transcripts), nucleic acid analogues (e.g., locked nucleic acids (LNA), protein nucleic acid (PNA), and pseudo-complementary-PNA (pc-PNA) etc), and regrowth agents and the like. Where cells are deposited, larger nanoapertures of the nanostencils are recommended.

In particular, in some embodiments, the nanostencil lithography (NSL) fabrication methods as disclosed herein can be used to deposit nanostructures comprising regrowth agents, for example, a regrowth agent such as a carbon nanotube, which serves as a "seed" which serves as a catalyst for the regrowth of additional carbon nanotubes at the specific location in the predetermined patterns.

The high-throughput and high resolution nanofabrication methods as disclosed herein provide for a low operational cost and low complexity fabrication process that is important for the advancement of nanoplasmonic and nanophotonic fields.

The high-throughput fabrication approach according to the present invention is based on nanostencil lithography and provides for high-throughput fabrication of, e.g., engineered infrared plasmonic nanorod antenna arrays, and other complex plasmonic nanostructures. The present invention enables the fabrication plasmonic supports supporting spectrally sharp collective resonances and the resulting plasmonic nanostructures are comparable to plasmonic nanostructures fabricated by electron beam lithography. In addition, in accordance with the invention, the nanostencils can be reused multiple times to fabricate many identical plasmonic nanostructures (for example, infrared nanoantenna arrays) having identical optical responses. Finally, the inventors demonstrate fabrication of plasmonic nanostructures in various shapes with a single metal deposition step on different supports, including non-conducting supports, such as glass or quartz. Further, in accordance with one or more embodiments of the invention, the reusability of stencil and the broad flexibility of the support choice, and predefined nano-pattern design provide for the development of complex plasmonic nanostructures for real-world applications.

One aspect of the present invention described herein is referred to herein as "nanostencil lithography" (NSL). NSL comprises a shadow-mask patterning technique that can be used to fabricate structures with sub-100 nanometer resolution. The methods according to embodiments of the invention comprise direct deposition of materials through a pre-patterned stencil or mask. The deposited material can be metallic, dielectric and/or organic. The mask, which acts as a stencil, is fabricated from any appropriate mask material, depending on the deposition material and the deposition environment. In accordance with one embodiment of the invention, the mask can be formed from a suspended silicon nitride membrane using EBL (or FIB) and dry etching methods. The mask can include a large number of nanoapertures and/or nano-slits having a wide variety of shapes, sizes, and arrangements. In some embodiments, the mask can be fabricated on wafer scale for high-throughput nanofabrication applications.

In accordance with an embodiment of the invention, the mask can be placed in direct or indirect contact on a desired support, in order to facilitate direct pattern deposition of a plamonic material (such as a noble metal), and enable lift-off free production of nanoparticles and nanowires with high reliability and uniformity. Since NSL as described herein does not require any resists, it has the advantage of reducing the fabrication steps and allowing the patterning on a wider range of supports. Another advantage of NSL is that the masks can be reused to pattern the same plasmonic nanostructures multiple times with minimal effort and high fidelity. As demonstrated herein (see FIGS. 29A and 29C), the NSL method can be used to fabricate nanostructures where no particle scattering occurs and where the nanostructure is essentially the same size dimensions of the nanoaperture of the corresponding nanostencil, for example, by depositing the nanostructure material on a sticky and elastic support, such as PDMS. Such a support prevents a gap forming between the nanostencil and the support, and reduces particle scattering and results in consistent sized nanostructures which have a flat top or upper surface, e.g., for example, a nanorod would have a rectangular cross-sectional dimension. Where non-elastic substrates are used, e.g., silicon and the like, a finite gap will result in particle scattering surrounding the nanoparticle, and will result in a more triangular cross-section of the nanorod, as well as a lower height and more increase in height variation between nanostructures in the array (See FIGS. 29B and 29D).

In accordance with one embodiment of the invention, high-throughput fabrication of infrared plasmonic nanoantenna arrays using nanostencil lithography is described. Nanorods present a half-wave dipole antenna behavior and support plasmonic resonances linearly scaling with the rod length, which permits tunability of plasmonic resonances over a wide spectral range—from visible wavelengths to the infrared range. Furthermore, periodic arrangement of nanostructures, e.g., nanorods on the support enables radiative engineering of plasmonic excitations. The nanoantenna arrays described herein can support collective excitations leading to spectrally narrower far-field extinction resonances and far stronger near-field enhancements than what is achievable with individual constituent nanoparticles. The nanostencil lithography methods according to the present invention offer the flexibility and the resolution to engineer nanoantenna arrays and can be used to fabricate plasmonic supports in a high-throughput fashion and provide for spectrally sharp collective excitations at mid-infrared wavelengths. The extinction spectra of these nanoantenna arrays fabricated using the nanostencil marks and methods as disclosed herein are comparable to that of the arrays fabricated by other prior art methods. In addition, the nanostencil masks described herein can be reused multiple times to create a plurality of nanoantenna arrays having the same optical responses. Further, embodiments of the invention provide for fabrication of nanostructures in various shapes with a single metal deposition step on different supports, including non-conducting surfaces (i.e., $CaF_2$ and glass). In some embodiments, the support is a flexible support, as disclosed herein. In some embodiments, the flexible support can be wrapped around a curved surface, for example, an optical fiber and the like. In some embodiments, the flexible support is a thin-film support, for tailoring and active tuning of the resonance of the nanostructures on the support to a desired wavelength. As discussed herein, in particular embodiments, the support is a sticky and elastic support, such as PDMS and other polymers known to persons of ordinary skill in the art so that no gap exists between the nanostencil and the surface of the support.

In some embodiments, the NSL method can be used to fabricate nanostructures on sensitive supports, for example, supports which may be unable to withstand harsh post-processing methods such as dry etching and the like. Such supports include thin-film supports and stretchable and/or elastic supports as disclosed herein, for example, parylene C thin film, LDPE (known as cling wrap). In some embodiments, the nanostencil can be used multiple times in the NSL method to deposit nanostructure material (plasmonic or non-plasmonic) on the same substrate so that the nanostructure is built up in a number of layers. For example, with each subsequent NSL method, a new layer the nanostructure material is deposited on the previous later of nanostructure material which is on the support, to build the height of the nanostructure to a specific predetermined desired height.

Embodiments of the nanostencil and the method of nanostencil lithography fabrication as disclosed herein has several useful applications. For example, because of the flexibility of the nanostencil lithography to deposit nanostructures on a wide variety of different supports, e.g., flexible supports, stretchable supports, solid supports, and the like, as well as used to deposit nanostructures of different materials (e.g., plasmonic and non-plasmonic materials) one can use the NSL to fabricate a variety of different nanoantenna arrays.

In some embodiments, nanostencil and the method of nanostencil lithography fabrication as disclosed herein can be used for fabricating a plasmonic nanoantenna arrays, for example, for the ultra-sensitive detection of bioanalytes including, but not limited to, nucleic acid, proteins, such as antibodies, antigens, biomarkers, allergens, ligands, metabolites, virus, bacteria, tumor cells, etc. The ability to detect, locate, measure and/or quantify small concentrations of bioanalytes, such as zeptomolar levels of bioanalytes, allows for diagnostic use, treatment, and/or monitoring of specific diseases, physiological conditions (normal or abnormal), conditions, and therapies. For example, abnormal proteins in human disease could be detected. As another example, the normal signal transduction inside, or outside cells could be detected and monitored. It is envisioned that the plasmonic nanostructures described herein can be used in vivo or in vitro for screening purposes, i.e., high throughput methods of evaluating pathological conditions. High-throughput drug discovery screening is another example where embodiments of the invention described herein are useful.

Figure 17A:
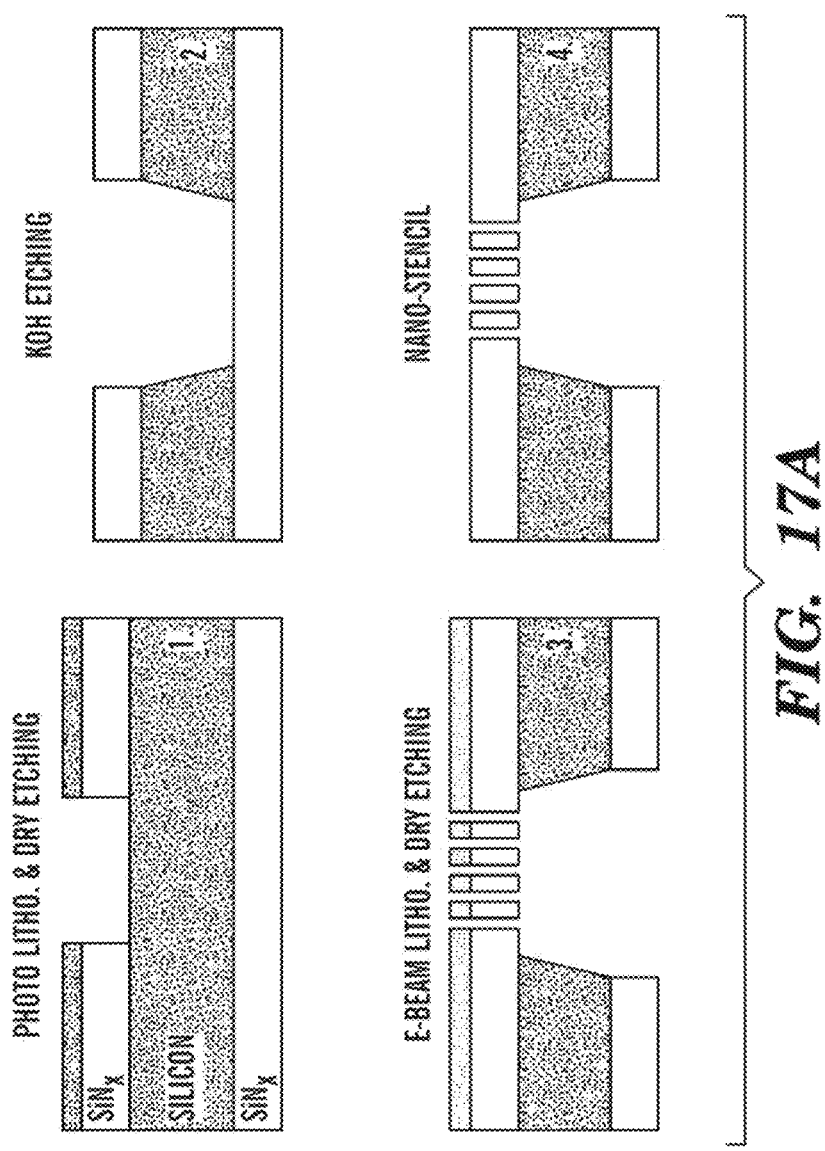
FIG. 17A is a diagram of a process for fabricating a nanostencil mask according to an embodiment of the invention.
Figure 17B:
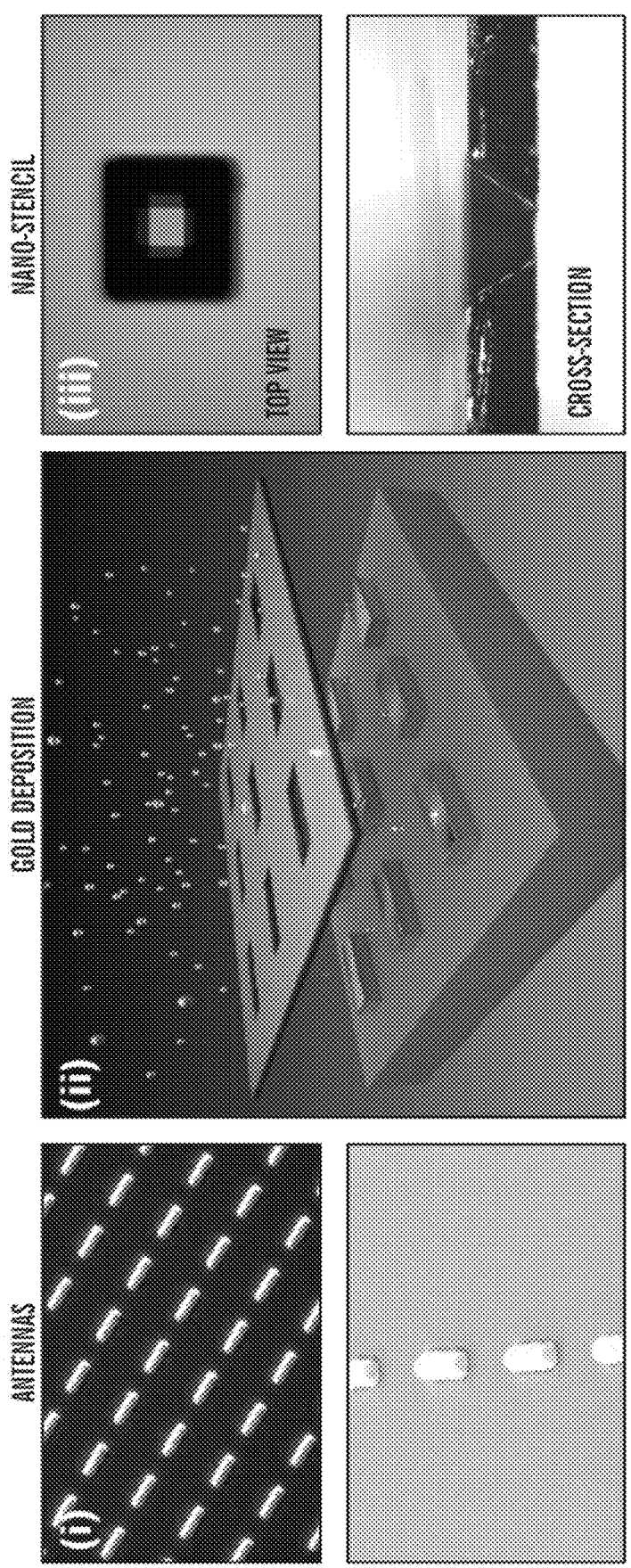
FIG. 17B is a modified version of FIG. 3B. The individual particle spectra obtained from random arrays are shown for comparison purposes (dashed lines).

FIGS. 17A-17B show the Nanostencil Lithography process according to one embodiment of the invention. This shadow-mask patterning technique can be used for high-throughput fabrication of plasmonic structures, such as antenna arrays. FIG. 17A shows fabrication of free standing membrane and nanostencil is illustrated in frames 1 to 4. Material removal processes, such as dry and wet etching processes and EBL can be used for achieving precisely defined pattern of nanoapertures/slits on the membrane.

FIG. 17B shows in part (i) top and angled SEM images of the gold nano-rod antenna arrays having 1100 nm length, 230 nm width and 100 nm height; at part (ii) a gold deposition scheme with reusable mask in accordance with one embodiment of the invention is illustrated; and at part (iii) top view and cross sectional images of a nanostencil according to one embodiment of the invention are shown.

Nanostencil fabrication process according to one embodiment of the invention is shown in FIGS. 17A-17B. In accordance with the invention, the process can include two stages. The first stage includes the fabrication of a free standing membrane as shown in frames 1 and 2. One important consideration in this embodiment is the mechanical strength of the membrane. In this example, the process was started with a 550 µm thick silicon wafer coated with 400 nm thick LPCVD SiNx on double sides. After cleaning with organic solvents, 2 µm thick MICROPOSIT™ S1 818™ positive photoresist was spin coated. One or more 800 µm×800 µm apertures in the SiNx layer were defined by photolithography with SUSS MicroTec MA/BA6 Mask Aligner and created by reactive ion etching (RIE) with Plasma Therm 790 RIE/PECVD System. Then, the chips were immersed in a KOH solution to selectively etch Si layer. This produced an approximately 200 µm×200 µm and 400 nm thick free standing SiNx membrane as the etching stops at the opposite SiNx layer. The Silicon wafer is etched with 54.7° angle side-wall profile, as shown at FIG. 17A.

The second stage includes patterning on the membrane, as shown in frame 3, to produce the nanoaperture pattern in the membrane. In one embodiment of the invention, the process includes spin coating positive e-beam resist poly (methylmethacrylate) (PMMA) followed by e-beam exposure using Zeiss Supra 40VP with GEMINI electron-optics column. Here, the EBL process is needed only once for the creation of the mask, since the mask can be used multiple times. After development of PMMA resist, nanoaperture patterns are transferred to the SiNx membrane by RIE using SF6 and Ar gases. The resulting structure is used as a nanostencil according to an embodiment of the invention. The top and the cross sectional views of a fabricated stencil masks are shown in FIG. 17B.

Figure 7A:
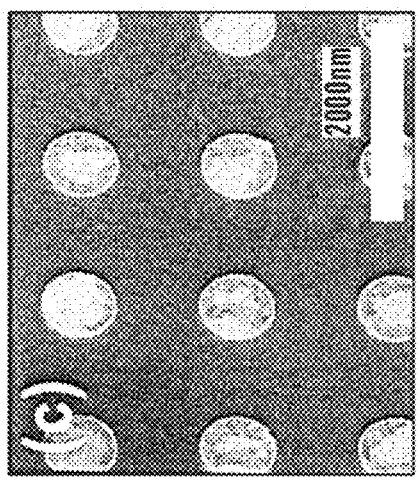
FIGS. 7A-7F show embodiments of different predefined geometric shapes and predefined spatial arrangements of nanostructures with respect to each other on (e.g., raised upon) or embedded (e.g., depressed or recessed) within the array support. Tailored nanoparticles or nanostructures in various predefined arrangements are collectively resonant. Specific predefined nanostructure geometries include nanorods (FIG. 7A), nanotriangles (FIG. 7B) and nanodiscs (FIG. 7C). Predefined non-periodic arrangement (FIG. 7D), predefined periodic arrangement (FIG. 7E) and dimmer arrangements (FIG. 7F) are also shown.
Figure 7B:
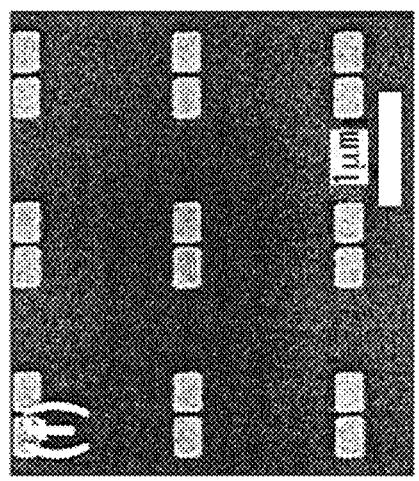
Figure 7C:
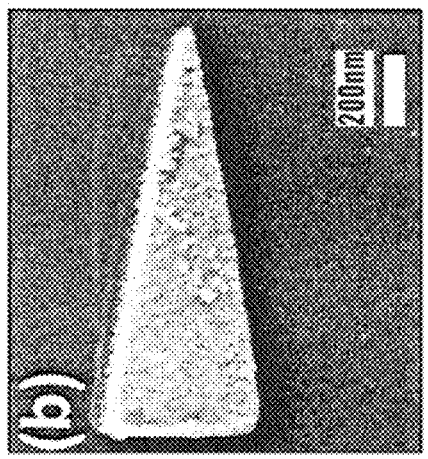
Figure 7D:
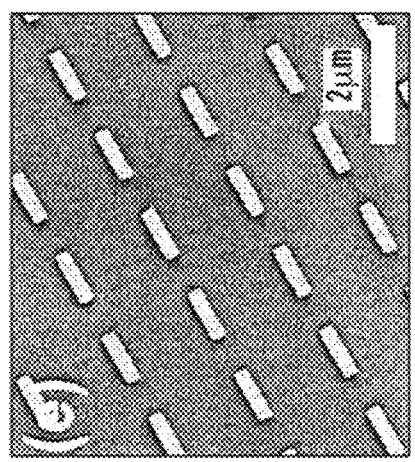
Figure 7E:
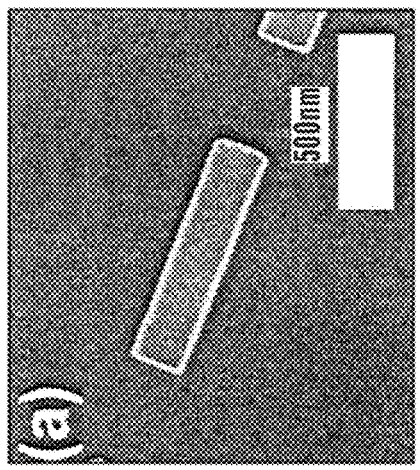
Figure 7F:
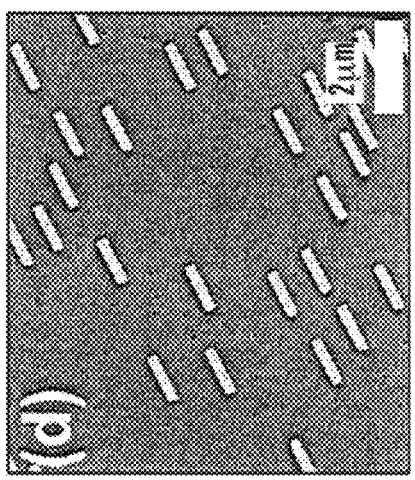

The nanostencil fabricated in accordance with one embodiment of the invention above can, in accordance with another embodiment of the invention, be used to facilitate direct deposition of metallic plasmonic materials on a broad range of supports to create complex nanoplasmonic devices, such as the nanoantenna arrays as disclosed herein. In such embodiments, in order to fabricate high quality plasmonic structures on the nanoantenna arrays, the gap between support and the nanostencil mask should be minimized. For example, in some embodiments, the stencil can be directly placed on or in direct contact with the support and secured tightly with one or more clamping devices, such as a clip or a clamp, so that the silicon side is facing up, while the patterned SiNx layer is kept in contact with the support. In such embodiments, it is believed, without wishing to be bound or limited by theory, that the sturdiness of the LPCVD SiNx layer plays important role for the durability of the mask. Directional gold deposition at $3\times10^{-6}$ Torr can be performed using, for example, a CHA-600S e-beam evaporator to apply a 100 nm gold film without depositing any prior adhesion layer (such as Ti or Cr) (FIG. 17B). Unlike EBL and other prior art methods, an adhesion layer is not necessary since NSL does not require metal lift-off processes. When the mask is removed, as shown in FIG. 7B, from the support, it leaves plasmonic nanostructures on the support with the shapes complimentary to the nanoapertures of the mask.

Figure 18A:
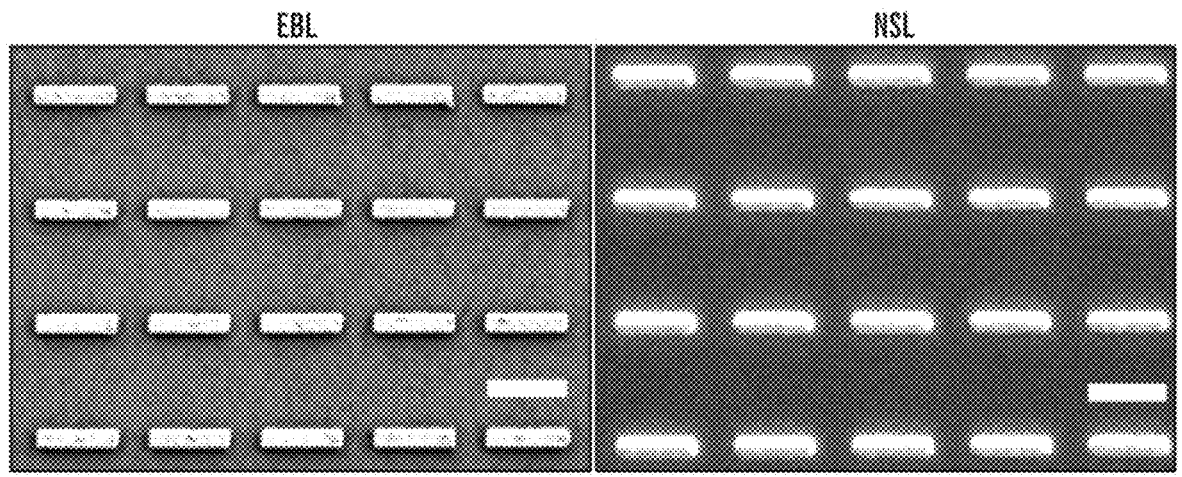
FIG. 18A shows (left) a nano-antenna array fabricated using electron beam lithography (EBL) and (right) an equivalent nano-antenna array fabricated according to an embodiment of the invention.
Figure 18B:
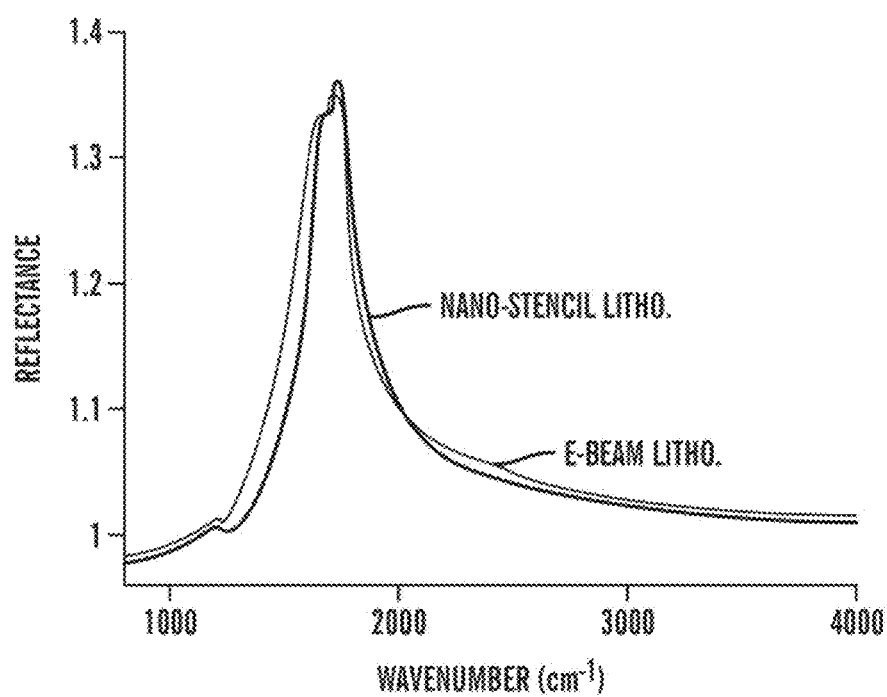
FIG. 18B shows similarity of reflection spectrum performance between the EBL fabrication method and the methods described herein.

FIGS. 18A and 18B show a comparison of nano-rod antenna arrays (left) fabricated using prior art EBL methods and nano-rod antenna arrays (right) fabricated using nanostencil lithograph, an embodiment of the present invention. FIG. 18A shows SEM images of nanorods with 1100 nm length, 230 nm width and 100 nm height fabricated using EBL (left) and NSL (right) are shown for comparison. White scale bars represent 1 µm. The NSL techniques described herein for large area patterning of nanorod arrays provide comparable quality with arrays fabricated using EBL. FIG. 18B shows that nanorods fabricated using two different techniques give identical reflection spectrum with resonances at approximately 1700 $cm^{-1}$. The spectral linewidth of the reflection resonances obtained from the antenna arrays fabricated according to an embodiment of the invention, NSL, is narrower.

In some aspects, the present invention can be used to fabricate various plasmonic nanostructures, including nanowires and nanoparticles, in different arrangements and on different types of supports. Described herein are fabrication details and optical characterization of gold nanorod arrays that act as very efficient infrared plasmonic antennas.

Nanorod arrays, fabricated according to an embodiment of the invention, using NSL, were investigated using SEM and compared against the nanorods with the same dimensions fabricated using the prior art EBL. FIG. 18A shows nanorod arrays fabricated on silicon with periods 1.5 µm, width 230 nm and height 100 nm using EBL and NSL. No irregularities on the periodicity or the physical dimensions are detected for the nanorod arrays fabricated according to the invention. In this embodiment of the invention, a 15% enlargement was observed in the nanorod lengths and the widths compared to the dimensions of the corresponding nanoapertures. To obtain nanorods with desired sizes, this enlargement can be considered and in accordance with the invention, compensated for, by scaling the apertures on the stencils accordingly in some embodiments. Round-edged nanoapertures on the mask caused particles to have rounded tips. Further, due to unavoidable gap between the mask and the support in this embodiment of the invention, scattering of gold particles at 20 nm vicinity of the nano-rods has also been observed. As described herein, this scattering had negligible effect on the optical quality of the structures.

The optical responses of the nanoantennas provide a better means for evaluating the quality of the fabricated nanostructures. The reflection spectra were obtained from the NSL fabricated arrays in the mid-IR frequency range and the results were compared with the spectra of the structures fabricated using EBL. In one example, the experimental set-up included an IR microscope coupled to a Bruker™ Fourier Transform Infrared (FTIR) spectrometer with a KBr beam splitter. Light is normally incident on the nanopatterned surface. Reflected infrared signal was collected using Cassagrian reflection optics (NA=0.4) coupled into a mercury cadmium telluride (MCT) detector. The reflectance spectrum shown in FIG. 18B shows a strong resonance at the designed wavelength of 5.77 µm. Absorption losses due to the naturally grown oxide layer on silicon supports were corrected with baseline fitting. Intensities of the reflected light obtained from the same size arrays were comparable for both fabrication schemes. The spectral linewidth of the resonances of the antenna arrays fabricated by the nanostencil process according to one embodiment of the invention was narrower than that of the arrays fabricated using prior art EBL. This observation indicates higher optical quality of the plasmonic structure fabricated according to the invention. These spectral and SEM measurements confirm the feasibility of using NSL fabrication process according to the invention for large area patterning of nanorod antenna arrays with high optical quality.

Figure 19A:
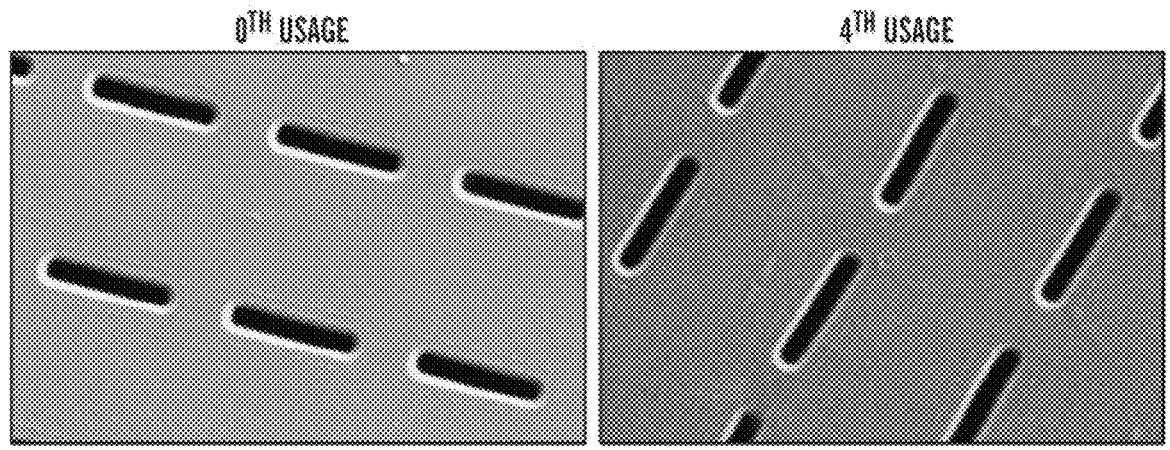
FIG. 19A shows SEM images of the nanostencil mask before the first use (left) and after the fourth use (right)
Figure 19B:
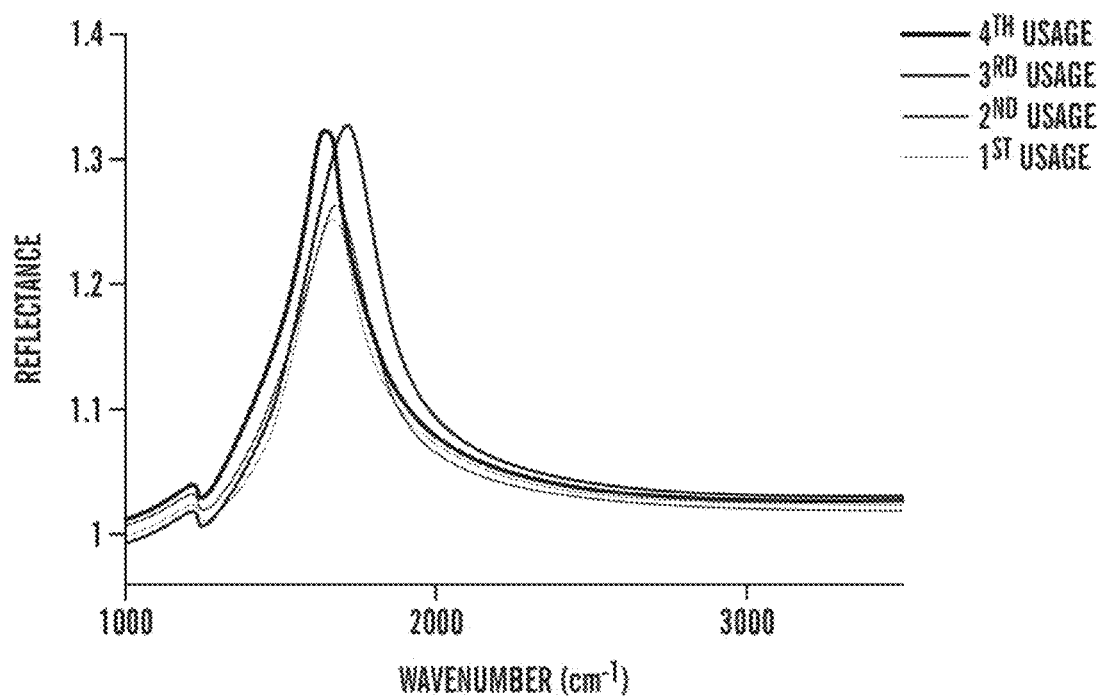
FIG. 19B depicts reflection spectrum performance of four nano-arrays fabricated using the nanostencil mask shown in FIG. 3A.

One unique advantage of the nanostencil lithography methods according to the invention is that nanostencils can be reused to fabricate multiple plasmonic devices having nearly the same properties. This capability provides for high-throughput fabrication of optimized nano-particle arrays. FIGS. 19A and 19B show that a mask can be reused multiple times. FIG. 19A shows SEM images of the same mask before it is used for the first time and after the fourth usage. Apertures have dimensions of 1050 nm length, 200 nm width and 100 nm height. No sign of degradation and deformation is observed on the mask after fourth usage. FIG. 19B shows the reflectance spectra for different nanorod arrays obtained from four consecutive depositions using the same mask. The resulting spectra show negligible deviations on resonances (3.5%) around 1700 cm$^{-1}$.

In accordance with one embodiment of the invention, reuse or recycling can be achieved by first dipping the used nanostencil in wet metal etchant and then rinsing in deionized (DI) water. In accordance with one embodiment, gold etchant can be used to clean the nanostencil including the remnants inside the nanoapertures after deposition. Once the deposited metal is removed, the stencil is ready to be used again. SEM images in FIG. 19A show the condition of stencil mask right before it is used for the first time, and also after the fourth usage (and subsequently cleaned). The sizes of the apertures, 1050 nm and 200 nm in width and height, are almost same for both cases. There is no sign of degradation and deformation after the fourth usage, indicating that the stencil can be further reused many times. FIG. 19B shows the reflection spectrum of the four nanorod arrays fabricated on different silicon chips by using the same nanostencil. The resulting spectra for all the structures have very similar spectral profiles. They show strong resonances around 1700 cm$^{-1}$ with deviations in the spectral peak position less than 3.5%, which could be due to the uncontrollable variations of the thicknesses of the deposited metals in the evaporation chamber. In accordance with embodiments of the invention, using a single stencil, optimized designs can be replicated many times with high degree of plasmonic antenna uniformity and similar optical response. As used herein, a "similar optical response" indicates that the deviation between two optical responses is less than 15%, less than 10%, less than 9%, less than 8%, less than 7%, less than 6%, less than 5%, less than 4.5%, less than 4%, less than 3.5%, less than 3%, less than 2.5%, less than 2%, less than 1.5%, less than 1%, or less than 0.5%. The high-throughput fabrication methods according to the present invention provide high through-put, high quality, and high fidelity of reproduction, in stark contrast to the serial nature of the prior art e-beam lithography methods.

The nanostencil fabrication methods according to the invention preserve the inherent flexibility of EBL to allow the creation of a wide variety of nanoparticle shapes and compositions at high resolution. This ability is especially useful, for example, for arrayed structures, as interesting physics have been shown in repetitive patterns of dielectric (photonic crystal) 50-52 and metallic (nanoplasmonic) nanostructures. As demonstrated herein, periodic arrays of plasmonic nanorods can be radiatively engineered to excite collective plasmons leading to spectrally sharp resonances with extremely strong local fields. Such collective behavior of nanostructures (e.g., nanoantennas) in nanoantenna arrays boosts the capabilities of each of the individual plasmonic nanostructure (e.g. nanorod). As discussed herein, the collective excitations can be explained from the fundamental principles using coupled dipole approximation. Plasmonic nanorods respond to an acting electric field on them with an induced dipole moment, which is maximum in strength at the localized plasmon resonance. For an individual antenna, this acting field is simply the electric field of the incident light. Once arrayed, the acting field on an individual antenna includes both (i) the incident field, and (ii) the sum of the retarded dipolar fields due to the other nanorods in the array:

$$\vec{E}_{acting,i} = \vec{E}_{incident,i} + \sum_{i \neq j} \vec{E}_{retarded,ij} = \vec{E}_0 e^{i\vec{k}\cdot\vec{r}_i} + \sum_{i \neq j} \left(\vec{c}_{ij} \cdot \vec{P}_j\right) e^{ikr_{ij}}$$

where, $E_0$ is the incident field, $P_j$ is the induced polarization of j-th antenna in the array, and $c_{ij}$ is the dipolar interaction matrix among nano-rods without the phase term. Accordingly, the strength of total field acting on an individual nano-rod strongly depends on the phase-delay experienced among the dipolar interactions. This acting field could be extremely large when the scattered fields are almost in-phase for a particular grating order ($\lambda_{incident} \approx n_{support} d_c/(i^2+j^2)^{1/2}$). This happens when the diffractive grating order is still evanescent such that the radiative damping of the plasmonic excitations is suppressed. Tuning of the individual antenna resonances (LSPs) to this incident wavelength (where the scattered fields are almost in-phase) strongly enhances the collective behavior and leads to extremely strong near-field excitations that are suitable for applications related to SEIRA, SERS and second harmonic generation.

Figures 20A, 20B:
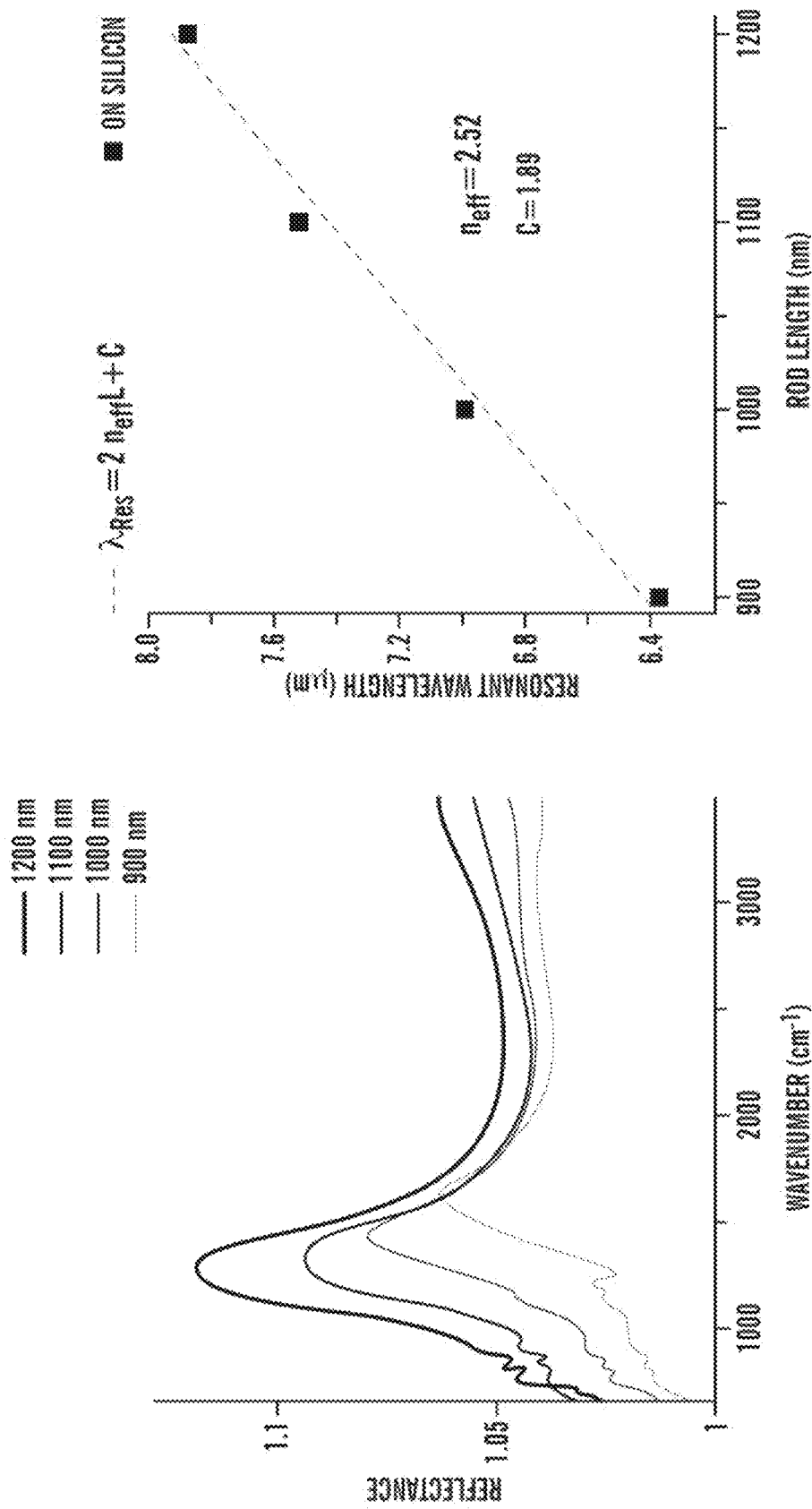
FIG. 20A shows a graph of the reflectance spectra of randomly arranged nanorods with lengths as indicated in the legend, 230 nm widths and 100 nm heights.
FIG. 20B shows a graph of rod length versus Resonant wavelength demonstrating that nanorod resonances closely follow the linear scaling relation.

FIGS. 20A and 20B show the performance of plasmonic gold nano-rod arrays fabricated according to one embodiment of the invention. The graphs in FIGS. 20A and 20B demonstrate these plasmonic gold nano-rod arrays display antenna like behavior in Mid-IR frequencies. FIG. 20A shows reflectance spectra of randomly arranged nanorods with lengths indicated in the legend, 230 nm widths and 100 nm heights. FIG. 20B shows that fundamental (m=1) resonance wavelengths (squares) are linearly dependent on the rod length (dashed red line is linear fit). The effective refractive index (neff) and constant fitting parameter (C) were calculated as 2.52 and 1.89 μm, respectively.

For optimal performance, tailoring of the nanoantenna arrays, e.g., nano-rod arrays can require optimization of the individual nanoantenna (or the individual nanoplasmonic structures on the array) characteristics through the rod dimension, as well as the phases of the retarded dipolar interactions through the periodicity. To obtain the individual antenna response, for example, one can fabricate randomized (but consistently oriented) arrays of nano-rods. The random arrangement of nano-rods cancels out any long-range dipolar interactions among the nano-rods, while allowing for the measurement of individual antenna behavior at high signal to noise ratios with, for example, an interferometer. FIG. 20A shows the resonance spectrum of the randomized nano-rod arrays with varying lengths for a fixed width (230 nm) fabricated on silicon over an area of 100×100 μm2.

In analogy with half-wave dipole antenna from the microwave theory, nano-rod resonances scale linearly with the rod length as $\lambda_{res} = 2n_{eff} L + C$. Where, $n_{eff}$ is the effective refractive index of the medium (silicon and air) surrounding the antenna and C accounts for the finite width and height. For a cylindrical nanoantenna with hemispherical ends and its first order mode, constant C is given by $4Rn_{eff}$. As shown in FIG. 20B, nanorod resonances closely follow the linear scaling relation. Increasing the rod length results in red-shifting of the resonance wavelength. Fitting of the experimentally observed resonance wavelengths to the dipolar antenna formula yields $n_{eff}=2.52$ for the effective refractive index of the medium (silicon and air) surrounding the antenna. The constant fitting parameter C resulted in an effective cross-sectional radius of 188 nm, which is in close agreement with the average value of the width and the height of the antennas, 170 nm.

Figures 21A, 21B:
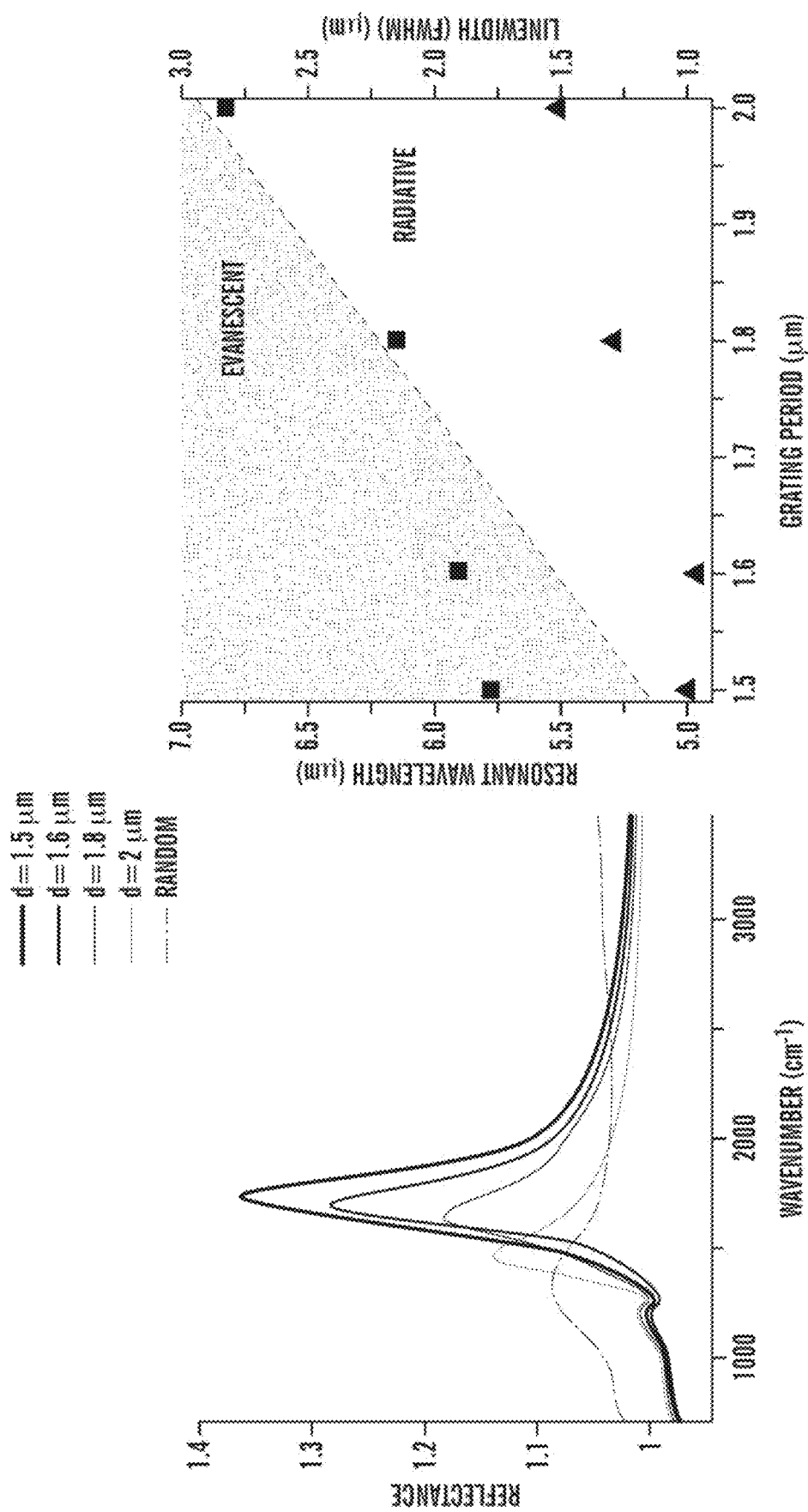
FIG. 21A shows a graph of spectral characteristics of periodic nanorod arrays fabricated using an embodiment of the invention.
FIG. 21B shows a graph of grating period versus resonant wavelength showing evanescent and radiative spectral regions.

FIGS. 21A and 21B show the spectral characteristics of periodic nano-rod arrays fabricated according to one embodiment of the invention. FIG. 21A shows reflectance spectra of the periodic nano-rod antenna arrays with 1100 nm length, 230 nm width, 100 nm height and periodicities changing from 1.5 to 2 μm (indicated in the legend). Spectrum of 1100 nm long individual nano-rod antenna (black curve) is also presented for reference. FIG. 21B shows resonance wavelengths (square, left y-axis) and the line widths (triangles, right y-axis) for varying periodicities. The dashed line separates the evanescent (shaded) and the radiative spectral regions for the first grating order on the silicon/air interface.

FIG. 21A shows spectral narrowing of the far-field responses as a result of collective excitation of the plasmons. The data are shown for nanorod arrays (L=1100 nm) with changing periodicities (d=1.5, 1.6, 1.8 and 2 μm). Spectrum of an 1100 nm long individual nanorod antenna indicating LSPR, (obtained from randomized arrays) is also presented for reference (black curve). Slight shifting of the LSP resonance is observed with respect to the ones in the prior art (reference 17) due to the absence of the titanium layer and the variation of the metal thickness. It is noted that periodicity is dominant in controlling the resonance frequencies of the antenna arrays. The effect of the periodicity on the resonance wavelengths and line-widths of the far-field reflectance spectra is summarized in FIG. 21B. Where the dashed line separates the evanescent and the radiative spectral regions for the (1, 0) grating order at the silicon interface for a given periodicity. For periodicities smaller than d=1.8 μm, the diffractive grating order is evanescent and leads to the suppression of the radiative damping. Therefore, significantly narrower far-field spectral response (approx. 1 μm with respect to approx. 3 μm of an individual nanorod) is observed as a result of electromagnetic field confinement within the array. For grating periods d=1.8 and 2.0 μm, the grating order changes from evanescent to radiative in nature. Hence, broadening of the resonances is observed with increased radiative damping.

The spectra shown in FIGS. 21A-21B, including the line widths and the intensities, closely match with the spectra of the nanorod arrays fabricated using the prior art EBL. In this embodiment, the collective resonances of the plasmonic arrays were tuned to the amide-I and amide-II vibrational bands of the protein backbone, which are 1660 cm$^{-1}$ and 1537 cm$^{-1}$ respectively. These collective plasmonic excitations accompanied with enhanced near field intensities are highly suitable, for example, for spectroscopic applications, such as for ultrasensitive vibrational nanospectroscopy, and measurements of vibrational signatures of bioanylates, such as single protein monolayers.

As described herein, nanostencil lithography is a resist free process that allows the transfer of the nano-patterns of nanostructures to any planar support. Such flexibility in support choice is in sharp contrast to EBL and FIB lithography, which require conductive supports or addition of a conducting film. Furthermore, resist based lithography techniques limit the shape and the size of the support due to the edge-bead formation in spin coating step. Certain applications may require use of non-conductive supports with irregular shapes. For example, for optical bio-sensing applications at visible frequencies, using either glass or quartz based microscope slides can be highly advantageous due to their optical transparency and low-cost. Similarly, at mid-IR frequencies, $CaF_2$ windows can be very suitable. The use of prior art EBL method on these insulating supports requires addition of a conductive film, either as a thin ITO layer before the application of EBL resist, or as a thin sacrificial metal layer on the e-beam resist. As is known to one of skill in the art, the ITO layer used in the former approach can interfere with the plasmonic responses of metallic nanoparticles, while the latter one involves additional fabrication steps. However, using the novel NSL methods according to the invention provide for direct patterning of plasmonic nano-antennas on non-conducting slides with a single metal deposition step.

Figure 22B:
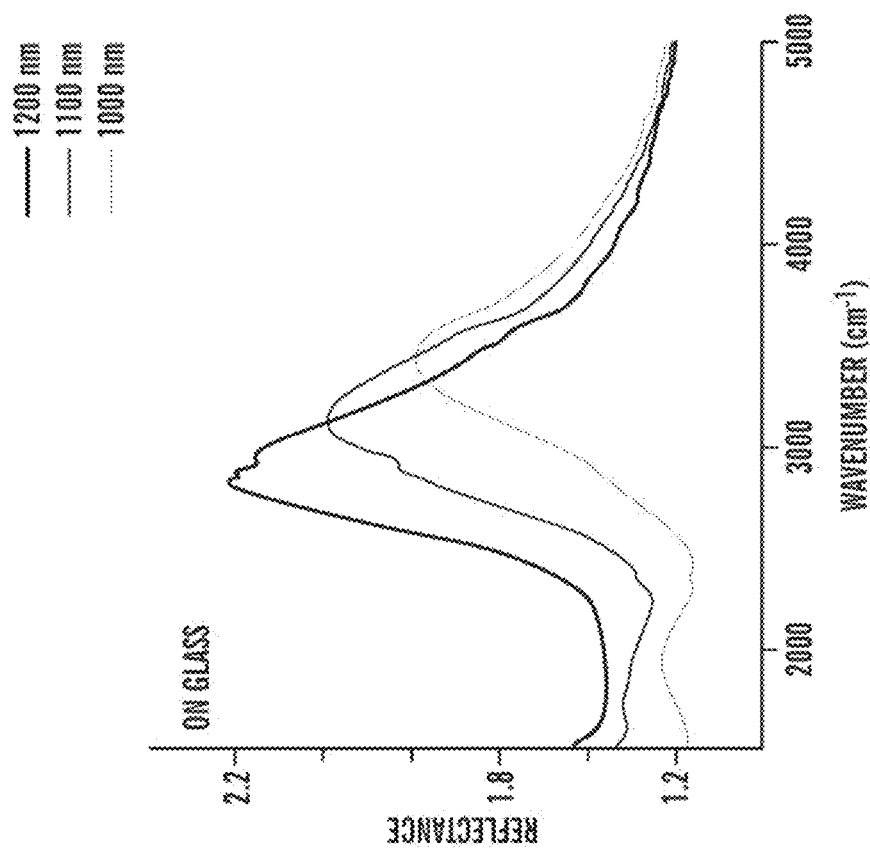
FIG. 22B shows a graph of reflectance spectra of randomly distributed nanorods on glass.
Figure 22A:
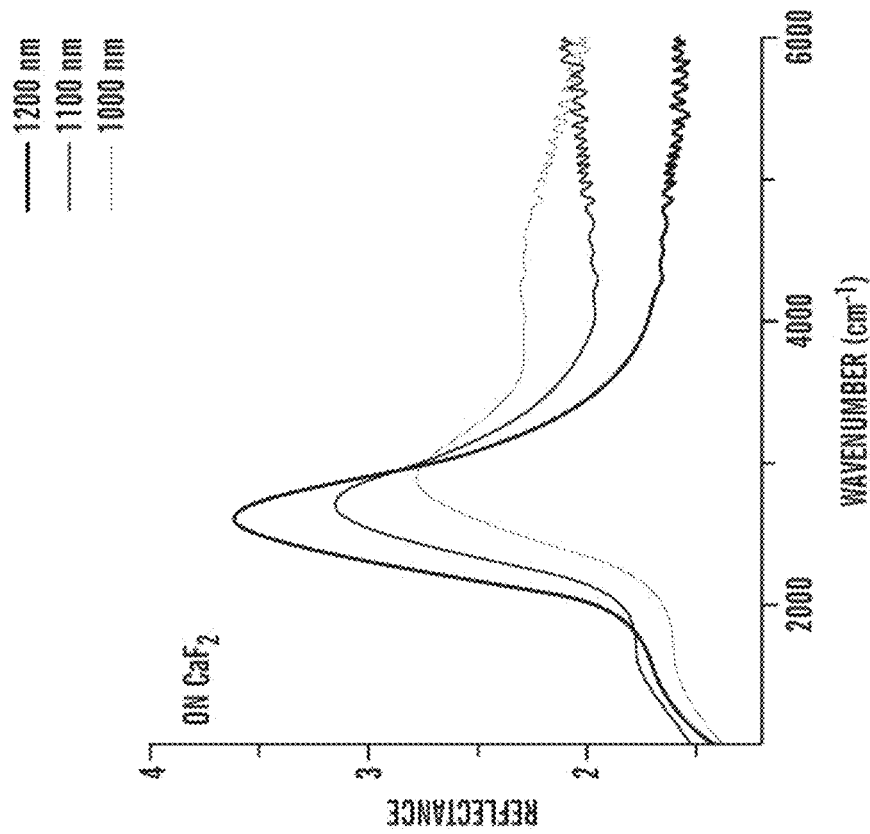
FIG. 22A shows a graph of reflectance spectra of randomly distributed nanorods on calcium fluoride.
Figure 22C:
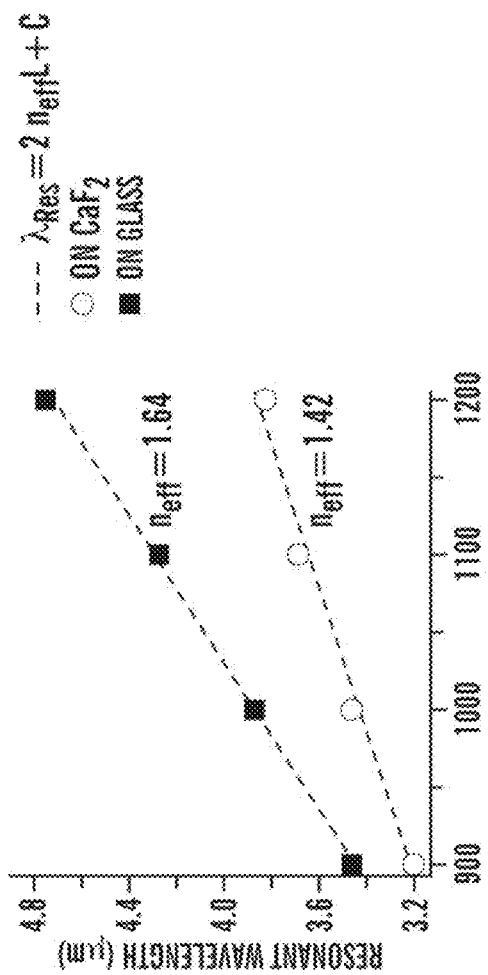
FIG. 22C shows a graph of rod length versus resonant wavelength, demonstrating that the fundamental resonance wavelength on $CaF_2$ and glass are linearly dependent on rod length.

FIGS. 22A and 22B show reflectance spectra of randomly distributed nano-rods on calcium fluoride (FIG. 22A) and on glass support (FIG. 22B). Legends indicate the rod lengths. $CaF_2$ support supports plasmonic resonances at shorter wavelengths and shows stronger resonances with narrower line widths compared to the glass. FIG. 22C demonstrates that fundamental (m=1) resonance wavelength on glass (squares) and on $CaF_2$ (circles) supports are linearly dependent on the rod length (dashed lines are linear fit). Effective refractive index calculated to be 1.64 for glass and 1.42 for $CaF_2$ are close to the actual values.

The optical responses of gold nano-rod arrays fabricated on glass and $CaF_2$ are shown in FIGS. 22A-22C. The nanoantennas, intentionally distributed randomly, show distinct LSP resonances. The width and the height of the antennas had been set to 230 nm and 100 nm respectively and the nano-rod lengths had been varied from 1000 nm to 1200 nm. In agreement with the dipole antenna theory, wavelengths of the plasmonic resonances scale linearly with the nano-rod length. For a given nanorod length, the antennas deposited on a $CaF_2$ support for plasmonic resonances at shorter wavelengths (longer wavenumbers) with respect to the antennas fabricated on glass surface, since $CaF_2$ has a lower refractive index ($n_{CaF2}$=1.40) than glass ($n_{glass}$=1.51). Experimentally measured resonances were least square fitted to the dipole antenna scaling relation. The estimated refractive index values (1.64 and 1.42 for glass and $CaF_2$ respectively) closely match to the actual values. The antennas fabricated on $CaF_2$ supports, compared to the ones on glass, show stronger resonances with narrower line width, due to the lower optical absorption of $CaF_2$ with respect to glass at mid-IR frequencies.

The Nanostencil lithography processes according to various embodiments of the invention can be used to create plasmonic nanostructures in various shapes, dimensions, materials, and arrangements. This can be achieved by simply changing the aperture pattern on the silicon nitride membrane, as shown in FIGS. 23A, 23B and 23C. The SEM images show a) circular gold nano-antenna arrays with 200 nm diameter and 600 nm period in triangular lattice (FIG. 23A), gold nano-wires with uniform 350 nm width and 50 μm length (FIG. 23B), gold nano-rod arrays (FIG. 23C) are shown. All structures are fabricated on silicon using an embodiment of the invention.

FIG. 23A shows SEM images of circular gold nano-antenna arrays fabricated in triangular lattice on silicon support. The particles have 200 nm diameter with 600 nm periodicity. The diameters of the nano-particles are 30 nm larger than the corresponding circular nano-apetures. The shape, size and periodicity distribution of these smaller nanoparticles have been observed to be very uniform over the area of the stencil (100 μm×100 μm). As the dimensions of the particle diminish, the resonances shift towards the visible wavelength regime. High-throughput fabrication of plasmonic nanoantenna arrays supporting resonances at visible spectrum can be used for non-linear photonic and photovoltaic applications. FIG. 23B shows SEM images of gold (Au) nano-wires with 350 nm width and 50 μm length fabricated on silicon over 50 by 50 μm area. The corresponding nano-slits were 300 nm and 50 μm in width and length. No discontinuity or width fluctuation is observed on the wires. The wires fabricated by the nanostencil technique can carry electrical signals. In addition, these wires can also be used optically as on-chip plasmonic waveguides for ultra-dense optical interconnects.

Uses of the Nanoantenna Arrays and Methods of Fabricating Such Nanoantenna Arrays The nanoantenna arrays as disclosed herein are useful in any application for where enhanced near-fields are attractive, such as disclosed in Ozbay, Science 311, 189-193 (2006); Lal, et al., Nature Photon. 1, 641-648 (2007)) including Raman (Stockman, et al., Phys. Rev. B 46 2821 (1992); Kneipp, et al., Phys. Rev. Lett. 78, 1667-1670 (1997)), and infrared absorption spectroscopies [Adato et al. Proc. Nat. Acad. Sci. USA 106 19227-19232 (2009); Neubrech, et al., Phys. Rev. Lett. 101, 157403 (2008), as well as for nonlinear optical phenomena (Sanchez et al., Phys. Rev. Lett. 82, 4014-4017 (1999)) and photovoltaics (Ferry, et al., Nano Lett. 8, 4391-4397 (2008)).

For other applications, narrower resonance line-widths, in addition to enhanced near-fields, could be desirable. For example, in biosensing applications based on refractive index change, the detection limit depends on both the LSPR sensitivity to the local dielectric environment and the resonance line-width (Artar, et al., Appl. Phys. Lett. 95 051105 (2009); Yanik, et al., Opt. Express 17 20900 (2009); Homola, et al., Sens. Actuators B 54, 3-15 (1999)). Narrower line-widths allow smaller shifts to be detected (White and Fan, Opt. Express 16, 1020-1028 (2008)). So far, most of the effort has been concentrated on optimizing the nanoparticle geometries to improve the near-field enhancements and to control the resonance frequencies/line-widths (Lee & El-Sayed, J. Phys. Chem. B 110 19220 (2006); Wang & Shen, Phys. Rev. Lett. 97 (2006); Sönnichsen, et al., Phys. Rev. Lett. 88 077402 (2002)). Further improvements in plasmon lifetimes and near-field enhancements require innovative approaches. Collective excitations of nanoparticle ensembles in well engineered periodic arrays offer a means to suppress radiation damping allowing improvements well beyond what is achievable by simply tuning the particle geometry (Adato et al.; Proc. Nat. Acad. Sci. USA 106 19227-19232 (2009).; Zou & Schatz, Nanotech. 17, 2813-2820 (2006); Della Valle et al., Phys. Rev. B 79 113410 (2009); Markel, J. Phys. B: At. Mol. Opt. Phys. 38, L115-L121 (2005); Lamprecht et al., Phys. Rev. Lett., 84 (2000). Auguié &. Barnes, Phys. Rev. Lett. 101, 143902 (2008); Kravets et al., Phys. Rev. Lett. 101 087403 (2008); Urzhumov and Shvets, Proc. SPIE, 5927 59271D (2005)). Herein, the inventors previously demonstrated narrow far-field extinction resonances and enhanced near-fields in rod-shaped nanoparticle (nanorod) arrays as a result of suppression of the radiation damping by electromagnetic field confinement in the ensemble plane (Adato et al., Proc. Nat. Acad. Sci. USA 106 19227-19232 (2009)).

In some embodiments, the nanoantenna arrays as disclosed herein are useful to improve signal (e.g., signal enhancement) in spectroscopy measurements, such as but not limited to infrared spectroscopy, as well as reduce sample volume and/or concentration of the sample to be measured.

In some embodiments, the plasmonic nanoantenna arrays can be used for the ultra-sensitive detection of bioanalytes including, but not limited to, nucleic acid, proteins, such as antibodies, antigens, biomarkers, allergens, ligands, metabolites, virus, bacteria, tumor cells, etc. The ability to detect, locate, measure and/or quantify small concentrations of bioanalytes, such as zeptomolar levels of bioanalytes, allows for diagnostic use, treatment, and/or monitoring of specific diseases, physiological conditions (normal or abnormal), conditions, and therapies. For example, abnormal proteins in human disease could be detected. As another example, the normal signal transduction inside, or outside cells could be detected and monitored. It is envisioned that the plasmonic nanoantenna arrays as described herein can be used in vivo or in vitro for screening purposes, i.e., high throughput methods of evaluating pathological conditions. High-throughput drug discovery screening is another example where embodiments of use of the plasmonic nanoantenna arrays are useful.

In particular, where a nanoantenna array is fabricated on a flexible support, it can be wrapped around a probe for being used for detection or spectroscopy in vivo, e.g., in a human. For example, where one can use the nanoantenna arrays, for example wrapped around a circular probe which can be inserted into a subject for detection of target molecules in a subject, such as a human to detect target biomolecules in tissues and cell. Such a method could be used to detect diseases similar as to an endoscope is currently used. In some embodiments, one can use the nanoantenna arrays, for example wrapped around a circular probe which can be directly inserted into biological sample, without having to take the an aliquot of the biological sample and place it on a planar nanoantenna array. This, this allows for quick sample methods, and if the nanoantenna array serves as a disposable attachment to a measuring device, such a disposable nanoantenna array would reduces the risk of sample contamination.

The nanoantenna arrays as disclosed herein are useful in spectroscopy methods to measuring any biomolecule known to persons of ordinary skill in the art, for example, biomolecules: Lipids, carbohydrates, collagens, DNA, amino-acids, peptides, thiols all support infrared absorption bands.

Additionally, the nanoantenna arrays as disclosed herein are also useful in any number of biomedical applications, including, but not limited to (i) drug discovery and development, where one can use the nanoantenna arrays as disclosed herein to assist in the measurement of conformation changes on membrane proteins in response to drug binding; (ii) fundamental biophysics, where the nanoantenna arrays as disclosed herein can be useful in the measuring of protein conformation in response to stimuli such as potential change, pH, photoexcitation. The nanoantenna arrays as disclosed herein are also useful in spectroscopy method for measuring other compounds and biomolecules, including but not limited to chemicals, toxins (e.g., liquid/gas), explosives, cells, pathogens, viruses, prions and any other organic or organic material or compounds, or the like.

Described herein are rapid, sensitive, simple to use, and portable nanoantenna arrays which can be used as biosensors that are useful for a variety of applications involving the detection of target molecules, biomolecular targets in samples and analytes, ranging from research and medical diagnostics, to detection of agents and toxins used in bioterrorism. Such targets molecules include, but are not limited to, polynucleotides, peptides, small proteins, antibodies, viral particles, and cells. Furthermore, the biosensors described herein have the ability to simultaneously quantify many different biomolecular interactions and formation of biomolecular complexes with high sensitivity for use in pharmaceutical drug discovery, proteomics, and diagnostics. Such biomolecular complexes include, for example, oligonucleotide interactions, antibody-antigen interactions, hormone-receptor interactions, and enzyme-substrate interactions.

The ability to detect biological target molecules, such as DNA, RNA, and proteins, as well as nanomolecular particles, such as virions, is fundamental to understanding both cell physiology and disease progression, as well as for use in various applications such as the early and rapid detection of disease outbreaks and bioterrorism attacks. Such detection, however, is limited by the need to use labels, such as fluorescent molecules or radiolabels, which can alter the properties of the biological target, e.g., conformation, and which can add additional, often time-consuming, steps to a detection process.

The direct detection of biochemical and cellular binding without the use of a fluorophore, a radioligand or a secondary reporter, using the nanoantenna arrays can be used to removes any experimental uncertainty induced by the effect a change in the molecular conformation, the blocking of active binding epitopes, steric hindrance, inaccessibility of the labeling site of a target molecule in a sample. The nanoantenna arrays as disclosed herein, and NSL methods for their fabrication greatly simplify the time and effort required for assay development, while removing experimental artifacts that occur when labels are used, such as quenching, shelf life, and background fluorescence.

The nanoantenna arrays and methods of use thereof provided herein are suitable for the detection of a wide variety of biomolecular targets present in a sample or analyte. Such biomolecular targets include, but are not limited to, sub-cellular molecules and structures, such as polynucleotides and polypeptides present in a sample. As the inventors have demonstrated a signal enhancement factors of $10^4$-$10^5$ using the nanoantenna arrays, which enable the collection of individual plasmonic responses of nanostructures arranged in a predefined pattern on the array, the nanoantenna arrays as disclosed herein can be used in nanospectroscopy, e.g., the measurement of the vibrational spectra of target molecules, e.g., proteins at zepto-mole levels. Herein the inventors have measured the vibrational spectra of a biological sample at zeptomole levels, corresponding to only 145 molecules per antenna, demonstrating the nanoantenna arrays as disclosed herein are useful for nanospectroscopy (e.g., spectroscopy using a small number or molecules). Absorption signals for the nanostructures on the nanoantenna arrays as disclosed herein are demonstrated herein with high reliability and reproducibility and far surpass those of the individual nanostructures by themselves.

In some embodiments of the present invention may be defined in any of the following numbered paragraphs:

1. A nanoantenna array device comprising; (a.) a support; (b) a plurality of plasmonic nanostructures where the plasmonic nanostructures has a controlled shape, wherein the plurality of plasmonic nanostructures have a predefined shape in a predefined pattern with respect to the support, and wherein the predefined pattern is a function of the collective excitation of plasmons and localized plasmon resonance.

2. The nanoantenna array of paragraph 1, wherein the plurality of plasmonic nanostructures are raised on the surface of the support.

3. The nanoantenna array of paragraphs 1 or 2, wherein the plurality of plasmonic nanostructures are embedded at or below the surface of the support.

4. The nanoantenna array of any of paragraphs 1 to 3, wherein the plurality of plasmonic nanostructures is a combination of a plurality of plasmonic nanostructures above the surface of the support and a plurality of plasmonic nanostructures embedded at or below the surface of the support.

5. The nanoantenna array of any of paragraphs 1 to 4, wherein the predefined pattern is a periodic pattern.

6. The nanoantenna array of any of paragraphs 1 to 4, wherein the predefined pattern is a non-periodic pattern.

7. The nanoantenna array of any of paragraphs 1 to 6, wherein the predefined pattern is a uniform pattern.

8. The nanoantenna array of any of paragraphs 1 to 7, wherein the predefined pattern is a lattice.

9. The nanoantenna array of any of paragraphs 1 to 8, wherein the predefined pattern is not a random pattern.

10. The nanoantenna array of any of paragraphs 1 to 8, wherein the predefined pattern is a super-periodic pattern.

11. The nanoantenna array of any of paragraphs 1 to 10, wherein the support is a non-conductive layer.

12. The nanoantenna array of any of paragraphs 1 to 11, wherein the support comprises silicon.

13. The nanoantenna array of any of paragraphs 1 to 12, wherein the support is selected from the group consisting of: silicon, silicon dioxide, silicon nitride, MgF2, calcium fluoride (CaF2), a polymer, glass, diamond, ZnSe, Germanium, GaAs, quartz or a quartz based microscope slide.

14. The nanoantenna array of any of paragraphs 1 to 3, wherein the plurality of plasmonic nanostructures embedded below the surface of the support is layered with a material that can be penetrated by an incident wavelength of electromagnetic radiation.

15. The nanoantenna array of any of paragraphs 1 to 14, wherein the predefined shapes of the plasmonic nanostructures are shapes selected from the group consisting of: nanorod, nanorectangle, nanosquare, nanodisc, nanocircle, nano-oval, nanotriangle, cross-shaped, nanowires, or irregular shaped.

16. The nanoantenna array of any of paragraphs 1 to 15, wherein the plasmonic nanostructures are separated by a periodicity of between 100-10,000 nm.

17. The nanoantenna array of any of paragraphs 1 to 16, wherein the plasmonic nanostructures are separated by a periodicity of between 100-1000 nm.

18. The nanoantenna array of any of paragraphs 1 to 17, further comprising an adhesive layer, wherein the adhesive layer is between the support and the plurality of plasmonic nanostructures.

19. The nanoantenna array of paragraph 18, wherein the adhesive layer comprises titanium or chromium or a combination thereof.

20. The nanoantenna array of any of paragraphs 18 or 19, wherein the adhesive layer is at least 50 nm in thickness.

21. The nanoantenna array of any of paragraphs 18 or 19, wherein the adhesive layer is less than 50 nm thick.

22. The nanoantenna array of any of paragraphs 18 or 21, wherein the adhesive layer is less than 25 nm thick.

23. The nanoantenna array of any of paragraphs 18 or 21, wherein the adhesive layer is less than 15 nm thick.

24. The nanoantenna array of any of paragraphs 1 to 23, wherein the plasmonic nanostructures comprise at least one plasmonic material.

25. The nanoantenna array of any of paragraphs 1 to 24, wherein the plasmonic nanostructures comprise at least two or more different plasmonic materials.

26. The nanoantenna array of any of paragraphs 1 to 25, wherein the plasmonic material is a metallic material.

27. The nanoantenna array of any of paragraphs 1 to 26, wherein the metallic material is a selected from a Noble Metal, a transition metal or an alkali metal.

28. The nanoantenna array of any of paragraphs 1 to 25, wherein the plasmonic nanostructures comprise a non-plasmonic material.

29. The nanoantenna array of any of paragraphs 1 to 26, wherein the metallic material is selected from the group consisting of: gold (Au), Silver (Ag), rhodium, palladium, osmium, iridium, platinum (Pt), titanium (Ti) and Aluminum (Al), Palladium (Pd), or any combination thereof.

30. The nanoantenna array of any of paragraphs 1 to 29, wherein the metallic material is a Noble metal, which is selected from the group consisting of: gold (Au), Silver (Ag), rhodium, palladium, osmium, iridium and platinum (Pt).

31. The nanoantenna array of any of paragraphs 1 to 29, wherein the plasmonic material is selected from the group consisting of: gold (Au), Silver (Ag), platinum (Pt), Copper (Cu), Aluminum (Al), Palladium (Pd), iron, vanadium, molybdenum or alloys thereof, or any combination thereof.

32. The nanoantenna array of any of paragraphs 1 to 31, wherein the plasmonic nanostructures are coupled to one or more other plasmonic nanostructures.

33. The nanoantenna array of paragraph 32, wherein the coupled plasmonic nanostructures comprises two or more nanorods in a parallel configuration.

34. The nanoantenna array of any of paragraphs 1 to 33, wherein the coupled plasmonic nanostructures comprises two or more nanorods in a series configuration or in a dimer configuration.

35. The nanoantenna array of any of paragraphs 1 to 34, wherein the coupled plasmonic nanostructures comprises two or more nanotriangles.

36. The nanoantenna array of any of paragraphs 1 to 35, wherein the coupled plasmonic nanostructures comprises two or more nanotriangles in a bow-tie or dimer configuration.

37. The nanoantenna array of any of paragraphs 1 to 36, wherein the coupled plasmonic nanostructures comprises two or more plasmonic nanostructures in a symmetrical configuration.

38. The nanoantenna array of any of paragraphs 1 to 37, wherein the coupled plasmonic nanostructures comprises a plurality of nanotriangles in a star or cross configuration.

39. The nanoantenna array of any of paragraphs 1 to 38, wherein the plasmonic nanostructures comprise a plurality of layers of two or more different plasmonic materials.

40. The nanoantenna array of any of paragraphs 1 to 39, wherein the plasmonic nanostructures are arranged in a predefined pattern as a function of their localized plasmon resonance.

41. The nanoantenna array of any of paragraphs 1 to 40, wherein the plasmonic nanostructures are configured with respect to the surface of the support in a predefined pattern such that the collective resonances modify the quality factor or near-field enhancement properties of the resonance.

42. The nanoantenna array of any of paragraphs 1 to 41, wherein at least one of the nanoparticles forms a unit cell, and at least one unit cell is arranged in a pattern on the nanoantenna array to form a lattice, wherein light propagating from one unit cells to the next unit cell throughout the array results in a collective resonance on the nanoantenna array that differs from each unit cell's resonance in more than just an additive summing of each unit cell's resonance, wherein the unit cell's resonance results from light propagating from one unit cell to the next unit cell and wherein the light undergoes a fill integer multiple of $2\pi$ phase shift, and wherein the light forms a diffraction order that is evanescent, it does not propagate into the far-field, at wavelengths longer than the corresponding lattice mode and also radiative, it does not propagate into the far-field at wavelengths shorter than the corresponding lattice mode.

43. The nanoantenna array of any of paragraphs 1 to 42, wherein the plasmonic nanostructures are configured with respect to the surface of the support in a predefined pattern such that an acting electric field ($E_{acting,i}$) on a single neonplasmonic structure is the sum of the incident electric field ($E_{incident,i}$) and the sum of a retarded dipolar field due to the other neoplasmonic structures in the nanoantenna array, and is characterized by the formula:

$$\vec{E}_{acting,i} = \vec{E}_{incident,i} + \sum_{i \neq j} \vec{E}_{retarded,ij} = \vec{E}_0 e^{i\vec{k} \cdot \vec{r}_i} + \sum_{i \neq j} \left( \vec{c}_{ij} \cdot \vec{P}_j \right) e^{ikr_{ij}}$$

$E_0$ is the incident field, Pj is the induced polarization of j-th neoplasmonic structures in the array, and $c_{ij}$ is the dipolar interaction matrix among the plurality of neoplasmonic without the phase term.

44. The nanoantenna array of any of paragraphs 1 to 43, wherein the predefined pattern of the plurality of plasmonic nanostructures is in a lattice, and wherein the lattice is selected from the group of; a triangular lattice, a square lattice, a rectangular lattice, an octagonal lattice, a hexagonal lattice, and other lattices or combination of lattices.

45. The nanoantenna array of any of paragraphs 1 to 44, wherein the predefined pattern of the plurality of plasmonic nanostructures is not in a lattice or in a non-periodic pattern with respect to each other.

46. The nanoantenna array of any of paragraphs 1 to 45, wherein the support has a substantially planar surface.

47. The nanoantenna array of any of paragraphs 1 to 46, wherein the support is thin membrane carrier support.

48. The nanoantenna array of any of paragraphs 1 to 47, wherein the support does not comprise a thin conductive film on the surface of the support.

49. The nanoantenna array of paragraph 48, wherein the thin conductive film is selected from the group of: a thin ITO layer, a thin sacrificial metal layer, a flexible substrate, a grapheme layer, a conducting polymer layer, or combinations thereof.

50. The use of the nanoantenna array of any of paragraphs 1 to 49 with visible wavelength.

51. The use of the nanoantenna array of any of paragraphs 1 to 49 with mid-IR wavelength.

52. A nanoantenna array for use in spectrometry.

53. The nanoantenna array of paragraph 52, wherein the spectrometry is nanospectroscopy.

54. The nanoantenna array of paragraph 52 or 53, wherein the nanospectroscopy is used for bioanalyte detection, chemical detection, toxin detection, gas detection.

55. The nanoantenna array of any of paragraphs 52 to 54, wherein the bioanalyte is selected from the group consisting of: a protein, a small molecule compound, a metabolite, a peptide, a lipid, a polysaccharide, a nucleic acid, and a nucleic acid analogue.

56. The nanoantenna array of any of paragraphs 52 to 55, wherein the spectrometry uses spectrally narrow far-field extinction resonances.

57. The nanoantenna array of any of paragraphs 52 to 56, wherein the spectrometry uses enhanced near-field intensities at the extinction resonances.

58. The nanoantenna array of any of paragraphs 52 to 57, wherein the spectrometry uses infra red wavelengths.

59. The nanoantenna array of any of paragraphs 52 to 58, wherein the spectrometry is vibrational spectroscopy.

60. The nanoantenna array of any of paragraphs 52 to 58, wherein the nanoantenna array is defined according to any of paragraphs 1 to 49.

61. A nanoantenna array for use in enhancing near-field electromagnetic fields in spectrometry.

62. A nanoantenna array for use in enhancing near-field infra-red electromagnetic fields in spectrometry.

63. A nanoantenna array for use in collective excitations of plasmons in spectrometry.

64. The nanoantenna array of paragraph 61, wherein the infra-red wavelength is mid-infrared frequency.

65. The nanoantenna array of paragraphs 61 and 62, wherein the mid-infrared frequency is in the amide-I (1660 cm-1) and amide-II (1537 cm-1) frequencies.

66. The nanoantenna arrays of paragraphs 61 to 65, wherein the nanoantenna array is defined according to any of paragraphs 1 to 49.

67. A method for chemical imaging a target molecule using the nanoantenna array of any of paragraphs 1 to 49.

68. The method of paragraph 67, wherein the target molecule is a target bioanalyte.

69. The method of paragraph 67, wherein the target molecule is a selected from the group of: bioanalyte, chemical, metabolite, toxin, agent, pathogen, cell, gas, virus, prion.

70. A method of making a nanostencil comprising: (a) coating a carrier wafer with a ceramic material to provide a first ceramic layer and a second ceramic layer; (b) cleaning the ceramic layers with an organic solvent; (c) applying a photoresist coating to the first ceramic layer; (d) defining a first aperture using photolithography; (e) etching the first ceramic layer to produce a first aperture in the first ceramic layer; (f) etching the carrier to extend the first aperture through the carrier wafer to the second ceramic layer; (g) applying an e-beam resist to the second ceramic layer; (h) applying an electron beam to the e-beam resist on the second ceramic layer to create a predefined pattern of nanoapertures in the e-beam resist; (i) developing the e-beam resist; and (j) etching the predefined pattern of nanoapertures through the second ceramic layer.

71. The method according to paragraph 70, wherein the carrier wafer is a silicon wafer and the ceramic layers are SiyNx materials.

72. The method according to paragraph 70 or 71, wherein the second ceramic layer is a low pressure chemical vapor deposition silicon nitride film.

73. The method according to any of paragraphs 70 to 72, wherein the carrier wafer is approximately 500 microns thick and the ceramic layers are approximately 400 nm thick.

74. The method according to any of paragraphs 70 to 73, wherein the predefined pattern of nanoapertures includes at least one aperture measuring approximately 1200 nm or less by 250 nm or less.

75. The method according to any of paragraphs 70 to 74, wherein the predefined pattern of nanoapertures include a nanorod, a nanodisc, a nanoantenna, a nanowire, or a nanoparticle.

76. A method of depositing a nanostructure on a support comprising: (a) preparing a nanostencil having a predefined pattern of one or more nanoapertures corresponding to a desired pattern; (b) placing the nanostencil membrane in contact with the support; (c) depositing the material on the support through the nanostencil membrane; and (d) removing the nanostencil from contact with the support to leave the nanostructure.

77. The method of paragraph 76, wherein the nanostructure is a plasmonic nanostructure.

78. The method of paragraph 77, wherein the plasmonic nanostructure comprises a plasmonic material.

79. The method of any of paragraphs 70 to 78, wherein the nanostensil has one or more nanoapertures corresponding to a desired shape and pattern of the nanostructures, wherein the desired shape and pattern of nanostructures is a controlled geometric shape and controlled periodic pattern of the nanostructure with respect to other nanostructures designed for collective excitation of plasmons and localized plasmon resonance.

80. The method of paragraph 76, wherein the nanostructure is not a plasmonic nanostructure.

81. The method of paragraph 80, wherein the nanostructure does not contain a plasmonic material.

82. The method of any of paragraphs 76, 80 or 81, wherein the nanostructure comprises at least one or a combination of agents, nucleic acid, proteins, biomaterials, regrowth agents for other materials.

83. The method according to paragraph 76, further comprising:
a. cleaning the nanostencil membrane;
b. placing the nanostencil membrane in contact with a second support;
c. depositing the material on the second support through the nanostencil membrane; and
d. removing the mask from contact with the second support to leave the nanostructure.

84. The method of paragraph 83, wherein the material is a plasmonic material.

85. The method of any of paragraphs 78 or 84, wherein the plasmonic material is a metallic material.

86. The method of paragraph 85, wherein the metallic material is selected from the group consisting of: gold (Au), Silver (Ag), Rhodium (Rh), Palladium (Pd), Osmium (Os), Iridium (Ir), Platinum (Pt), Titanium (Ti) and Aluminum (Al), or any combination thereof.

87. The method of paragraph 78 or 84, wherein the plasmonic material is selected from the group consisting of: Gold (Au), Silver (Ag), Platinum (Pt), Copper (Cu), Aluminum (Al), Palladium (Pd), Iron (Fe), Vanadium (V), Molybdenum (Mb) or alloys thereof, or any combination thereof.

88. The method of paragraph 83, wherein the material is not a plasmonic material.

89. The method of paragraph 88, wherein the non-plasmonic material is selected from at least one or a combination of biomaterials, agent, proteins, nucleic acids, nucleic acid analogues, regrowth agents for other materials.

90. The method of paragraph 70 to 89, wherein the predefined pattern is a periodic pattern.

91. The method of paragraph 70 to 89, wherein the predefined pattern is not a periodic pattern.

92. A nanoantenna array fabricated according to the method of any of paragraphs 70 to 75.

93. A nanoantenna array fabricated according to the method of any of paragraphs 76 to 89.

94. A method of depositing a nanostructure on a support comprising: (a) providing a nanostencil membrane having a predefined pattern of one or more nanoapertures corresponding to a desired pattern; (b) placing the nanostencil membrane in contact with the support; (c) depositing the material on the support through the nanostencil membrane; and (d) removing the nanostencil from contact with the support to leave the nanostructure.

95. The method according to paragraph 92, further comprising: (a) cleaning the nanostencil membrane; (b) placing the nanostencil membrane in contact with a second support; (c) depositing the material on the second support through the nanostencil membrane; and (d) removing the mask from contact with the second support to leave the nanostructure.

96. The method according to paragraphs 92 or 93, wherein the nanostructure is a plasmonic nanostructure.

97. The method according to paragraphs 92 or 93, wherein the material is a plasmonic material.

98. The method according to paragraph 95, wherein the plasmonic material is a noble metal.

99. The method according to paragraph 95, wherein the plasmonic material is a directional gold material.

100. The method of any of paragraphs 92 to 97, wherein the plasmonic material is a metallic material.

101. The method of paragraph 98, wherein the metallic material is selected from the group consisting of: gold (Au), Silver (Ag), rhodium, palladium, osmium, iridium, platinum (Pt), titanium (Ti) and Aluminum (Al), Palladium (Pd), or any combination thereof.

102. The method of paragraph 98, wherein the plasmonic material is selected from the group consisting of: gold (Au), Silver (Ag), platinum (Pt), Copper (Cu), Aluminum (Al), Palladium (Pd), iron, vanadium, molybdenum or alloys thereof, or any combination thereof.

103. The method of paragraph 93, wherein the nanostructure is not a plasmonic nanostructure.

104. The method of paragraph 93, wherein material is not a plasmonic material.

105. The method of paragraph 102, wherein the non-plasmonic material is selected from at least one or a combination of biomaterials, proteins, nucleic acids, nucleic acid analogues, regrowth agents for other materials.

106. The method according to any of paragraphs 92 to 103, wherein the plasmonic material is deposited at 3×10-6 Torr in an e-beam evaporator to produce a layer of plasmonic material at a predefined thickness on the support.

107. The method according to any of paragraphs 92 to 104, wherein the nanostencil membrane is a flexible nanostensil membrane.

108. The method of any of paragraphs 76 to 107, wherein the support includes a sticky or elastic surface.

109. The method of any of paragraphs 76 to 107, wherein the support is a flexible support.

110. The method of any of paragraphs 76 to 109, wherein the flexible support can be wrapped around a curved element, or a fiber optic cable.

111. The method of any of paragraphs 76 to 107, wherein the support is a thin-film support.

112. The method of any of paragraphs 76 to 111, wherein the thin-film support is a stretchable support on elastic stretchable support.

113. The method of paragraph 112, wherein the thin-film support includes LDPE film, parylene C, and PDMF thin film.

114. A nanoantenna array device fabricated according to the method of any of paragraphs 76 to 113.

115. A nanoantenna array fabricated according to the method of any of paragraphs 76 to 113, wherein the support includes a conducting material, a thin-film support, a stretchable support, an elastic support, a flexible support.

116. A nanoantenna array fabricated according to the method of paragraph 115, wherein the conducting material includes silicon.

117. A nanoantenna array fabricated according to the method of any of paragraphs 76 to 113, wherein the support comprises a non-conducting material.

118. A method of fabricating a nanostencil comprising; (a) fabricating a free-standing membrane having a substantially uniform thickness, and (b) producing a predefined pattern of one or more nanoapertures through the free standing membrane.

119. The nanoantenna array of any of paragraphs 1-49, fabricated according to the methods of any of paragraphs 76 to 113.

120. A method for detecting one or more molecular targets comprising; (a) providing a nanoantenna array of any of paragraphs 1 to 49; (b) contacting one or more samples comprising one or more target molecules to the surface of the nanoantenna array; (c) illuminating one or more surfaces of the nanoantenna array with an incident light source to produce surface plasmons, before and after the contacting with one or more samples, (d) collecting and measuring light displaced from the illuminated film with an optical detection system, before and after contacting with one or more samples, and (e) detecting one or more target molecules based on the change or difference in the measurement of light displaced from the illuminated film before and after contacting with the one or more samples.

121. The method of paragraph 120, wherein target molecule is a target bioanalyte.

122. The method of paragraph 120, wherein the target molecule is a selected from the group of: bioanalyte, chemical, toxin, agent, pathogen, cell, gas, virus, prion.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

EXAMPLES

Materials and Methods

Antenna Support Fabrication.

Plasmonic nanostructrue antenna arrays were fabricated on silicon wafers by a single layer liftoff process, or via the high-throughput fabrication method as disclosed herein. For fabrication of the nanoantenna arrays using the single layer liftoff process, the arrays are fabricated as 100×100 µm² squares, thus the number of nanoantennas per array varied slightly depending on the periodicity ($63^2$ for 1.6 µm period, to $51^2$ for 2.0 µm period as well as the random arrangements) For the electron-beam lithography (EBL), chips were spin coated with PMMA 950 A5 (Microchem) and baked on a hotplate at 180° C. for 4.5 minutes. EBL was performed using a Zeiss SUPRA 40VP electron microscope with an accelerating voltage of 30 kV. The patterned chips were developed in a methyl isobutyl ketone (MIBK)-isopropanol (IPA) solution (MIBK:IPA=1:3) for 50 s, then rinsed in IPA for 20 s and blown dry with nitrogen. Approximately 70 nm of Au (Kurt J. Lesker, 99.999% purity) was evaporated onto the developed supports with a 5 nm layer of Ti (Kurt J. Lesker, 99.995% purity) for adhesion. The resist was lifted off with acetone and IPA leaving the patterned nanorod structures. As a final step, oxygen plasma clean (300 sccm, 150 watts, 5 min) in a plasma asher (PVA Te Pella America model M4L) was used to remove any remaining organic material.

FTIR Spectroscopy Measurements.

All spectral data were taken on a Bruker™ IFS 66/s Fourier Transform Infrared Spectrometer with a Hyperion 1000 IR microscope (NA=0.4) in reflectance mode. Knife edge apertures set to form a 100×100 µm² square opening is used to collect signal from a single antenna array. Background spectra were collected for each measurement from an aluminum reference mirror (with the aperture size kept constant throughout). The noise level in the spectra corresponds to 256 scans with a mirror velocity of 20 kHz. In difference spectra ($\Delta R/R_0$, as shown in FIGS. 4 and 6 in the text), the spectral contribution of the antennas themselves was removed by subtracting the signal obtained from the bare antenna arrays from that of the silk coated ones. The protein coating of the antenna arrays causes shifting of the plasmonic resonances, which is corrected using a fourth order polynomial baseline fitting. The data were processed by removing water vapor and $CO_2$ absorption bands and by 20-point boxcar smoothing. The $CO_2$ bands were removed by linearizing the spectral region between 2222-2440 $cm^{-1}$.

Silk Film Preparation.

Silk films were prepared by a spin coating procedure. The thickness of the silk fibroin film is controlled by varying its concentration in a water solution. Following spin coating at 4000 rpm for 45 seconds, the silk films are set to dry. The procedure leaves a crystalline film whose thickness is proportional to the concentration used in the spin coating procedure.

Numerical Simulations.

CST Microwave Studio was used for the FDTD simulations. Commercial software (CST Microwave Studio) was used for the FDTD simulations. A non-uniform mesh was used to improve accuracy in the vicinity of the nanorods where the field concentration and variations were the greatest. For the simulations of the isolated nanorod, the size of a unit cell with periodic boundary conditions was increased until the near-field amplitude spectra converged and further increases resulted in negligible variations.

Example 1

Nanoantenna Arrays

As disclosed herein, the inventors demonstrate that the engineered nanoantenna arrays can support spectrally well-defined resonances with strong local fields. Furthermore, plasmonic resonances in these nanoantenna arrays can be fine-tuned to specific spectral regions of interest with high spatial reproducibility. Recently, enhanced absorption signals have been observed from individual nanoantennas (Jensen et al., (2000); Applied Spectroscopy 54:371-377., Kundu et al., (2008) Chemical Physics Letters. 452:115-119; Neubrech et al., (2008) Physical Review Letters 101: 157403; Bukasov et al., (2009). Analytical Chemistry 81:4531-4535). However, a surprising new phenomena arises as a result of the collective resonant excitation of the spatially and geometrically organized nanoantenna in specific pattern ensembles. In the nanoantenna arrays as disclosed herein, where the nanoantenna (or plasmonic nanostructures) are organized in a predefined pattern on the nanoantenna array as opposed to configured at random, the radiative dipolar coupling and the interference of the multiple scattering from antennas in the array can be utilized for the spectral narrowing of the far field response.

More importantly, calculations demonstrate that these collective resonances are linked to the strongly enhanced near-field intensities. In this manner, much stronger coupling between the incident field and the transition dipole moments of the proteins can be achieved compared to the individual antennas and/or chemically prepared supports.

As disclosed herein, the inventors have demonstrated an ultra-sensitive collectively enhanced IR absorption (CEIRA) spectroscopy technique allowing direct identification of vibrational signatures of single protein monolayers of silk fibroin. Measurement of vibrational signatures with zeptomole level protein detection limits are achieved due to the $10^4$-$10^5$ signal enhancements. Absorption signals far surpassing those of the individual nanoantennas are shown with high reliability and reproducibility. Experimentally observed asymmetric absorption spectra and relative tuning of the vibrational absorption bands are explained using a Non-Equilibrium Greens Function (NEGF) technique (Datta S (2004) Nanotech. 15:S433-S451; Omenetto et al., (2008) Nature Photonics. 2:641-643.20-21). The near-field character of the enhanced signals is mapped by progressive loading of the nanoantenna with varying thicknesses of protein films. The large signal-to-noise ratios obtained here with CEIRA spectroscopy enables functional studies of monolayer protein films, a question of fundamental importance in biochemistry and biophysics.

Silk Fibroin:

The protein is silk fibroin is used herein as the protein to be analyzed, as it has attracted considerable attention because of its exceptional mechanical and optical properties (Omenetto et al., (2008) Nature Photonics. 2:641-643.). Apart from its intrinsic properties, the ability to form uniform layers with excellent thickness control (Lawrence et al., (2008) J. Mater. Sci. 43:6967-6985) makes silk protein an ideal model system for systematic studies of the infrared enhancement mechanisms in biomolecules.

Mechanisms of Collective Nanoplasmonics:

Nanoantenna arrays were initially engineered to comprise nanorod antennas supporting spectrally narrow collective plasmon excitations at mid-infrared frequencies, specifically at the amide-I (1660 cm$^{-1}$) and amide-II (1537 cm$^{-1}$) vibrational normal modes of the protein backbone. The lithographically fabricated structures are then coated with protein molecules whose vibrational dipole moments act as a load to the nanoantenna. Nanoantenna arrays, driven by an infrared light source, efficiently funnel the incident light to their load through the collectively enhanced plasmonic excitations. This collective behavior is controlled by the local electromagnetic field driving each nanoantenna. For an individual nanoantenna, the local field is simply the incident field that excites the localized surface plasmons (LSP) serving as the electric dipoles. In an array, on the other hand, the local field includes (i) the incident electric field, and (ii) the field created by the other induced dipoles:

$$E_{loc,i} = E_{inc,i} + E_{dipole,i} = E_0 e^{i\vec{k}\cdot\vec{r}_i} + \sum_{i\neq j} \vec{c}_{ij} \cdot \vec{P}_j e^{ikr_{ij}} \quad (8)$$

where, $E_0$ and $k=2\pi/\lambda$ are the amplitude and the wavevector of the incident wave. $\vec{P}_j$ is the induced polarization of the j-th antenna in the array while $\vec{c}_{ij}$ represents the long range dipolar interaction matrix without the phase term (see discussion related to "Dipole interaction matrix" as disclosed herein). The strength of the second term is controlled by the ensemble arrangement due to the phase component. For an arrangement where the induced dipolar field interactions are almost in phase, the local fields can become extremely large. Therefore, arrays of antennas generate a collective response resulting in strongly enhanced near-field excitations compared to the individual antenna.

Example 2

Individual and Collective Resonances of Plasmonic Nanoantennas

The plasmonic nanoantenna arrays for enhanced collective response were engineered herein based on the individual antenna behavior. To obtain individual response with a good signal to noise ratio using a conventional Fourier-transform infrared (FTIR) microscope, the nanoantennas were randomly positioned on the support of the array. As previously demonstrated by the inventors, the random arrangement of the nanoantenna array cancels out any diffractive behavior (Yanik et al., (2008) Appl. Phys. Lett. 93:081104). As shown in FIG. 9, the spectral measurements are independent from the randomization process and clearly reflect the individual antenna response. FIG. 1A demonstrates the infrared reflectance measurements from randomized arrays consisting of varying length and a fixed width (230 nm) of nanorods pointing in the same direction on an area of 100×100 μm$^2$. The structures are fabricated on silicon supports using electron beam lithography. A thin titanium adhesion layer is first deposited by electron beam evaporation, followed by ~70 nm thick gold layer. After lift-off, well-defined rod shaped structures were formed as shown in the scanning electron microscope (SEM) image of an individual nanoantenna (inset). For incident light polarized parallel to the long axis of the rods (//-polarized), the nanoantenna resonance follows a linear scaling relation (FIG. 1B). This scaling behavior could be understood from antenna theory concepts. A traditional half-wave dipole antenna of length L has a tiny feed-gap in between two segments of length $\lambda/4$ at which the antenna is connected to its load. When the feed-gap impedance is matched to the impedance of the load, induced current is maximized in the antenna and the load circuit. Accordingly, resonance occurs at a wavelength corresponding to the total length of the two $\lambda/4$ segments, (i.e. $L=\lambda_{Res}/2$). A nanorod antenna is fabricated as single particle with no feed-gap and the impedance matching condition is automatically met. As a result, the resonant excitation wavelength of a nanorod antenna with length L occurs approximately at $\lambda_{Res}=2Ln_{eff}$. Here, $n_{eff}$ is the effective refractive index, accounting for the inhomogeneous dielectric environment (support and air) surrounding the antenna. Slight deviations from the ideal half-wave dipole antenna behavior are due to the increasing penetration depth of the incident radiation at IR frequencies and decreasing aspect ratio of the long axis versus the short axis. Complete resonance which is overlapping of the plasmonic excitations with the vibrational amide-I and amide-II bands occurs for the nanoantenna length L=1100 nm. For incident light that is polarized perpendicular to the rod long axis, plasmon resonances are not excited over the spectral region of interest (FIG. 1A). The cross sectional near-field profile of the individual nanoantenna shown in FIG. 2A is obtained by 3-dimensional finite difference time domain (3D FDTD) simulations. Enhanced field intensities with a factor of ~$10^2$-$10^3$ are observed for the //-polarized incident light near the tips of the nanoantenna. Although these enhancement factors are quite impressive, single monolayer measurements require even higher near-field intensities. This cannot be simply achieved by changing the nanoantenna geometry (Crozier et al., (2003) J. Applied Physics 94:4632-4642).

Collective excitations in well engineered antenna ensembles, on the other hand, can be exploited to achieve dramatically enhanced near-field intensities with much narrower far field spectral responses (Meier et al., (1985) J. Optical Society of America B 2:931-949; Lamprecht et al., (2000) Physical Review Letters 84:4721-4724.; Zou et al., (2004). J. 120:10871-10875; Augie et al., (2008) Physical Rev. Letts 101:143902; Zou et al., (2005) Chem. Physical Letts. 403:62-67). In a periodically arranged nanoantenna array with a period d, long range dipolar interactions among the nanoantennas become dominant over the localized near-field couplings for separations more than several tens of nanometers. At a fixed incident wavelength, the interaction term (given by the second component in Eq. (1)) accumulates larger phase delays when propagating between the antennas with increasing lattice spacing. The narrow resonance occurs for d slightly smaller than a critical periodicity $d_c$ where the light fields corresponding to the diffractive grating order (i,j) change from evanescent to radiative:

$$d_c \approx \frac{\sqrt{i^2 + j^2}}{n_{Si}} \lambda_{incident} \quad (9)$$

Figure 2B:
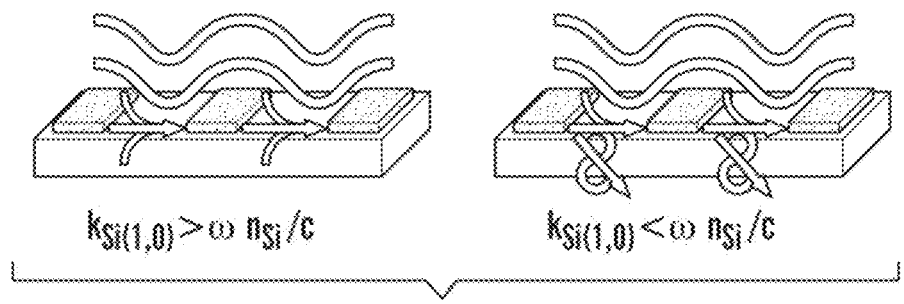

Here, $n_{Si}$ is the refractive index of the support and (i,j) are the diffraction grating orders. Collective excitations are created when the dipolar interactions among the antennas are almost in-phase just before the appearance of the grating order resulting in radiation damping (FIG. 2B). Tuning of the individual antenna LSPs to this incident wavelength strongly enhances the collective response and results in efficient funneling of the incident light into much stronger near-field excitations (Meier et al., (1985) J. Optical Society of America B 2:931-949; Lamprecht et al., (2000) Physical Review Letters 84:4721-4724.; Zou et al., (2004). J. 120: 10871-10875; Augie et al., (2008) Physical Rev. Letts 101: 143902; Zou et al., (2005) Chem. Physical Letts. 403:62-67). This behavior is well captured by the FDTD simulations presented in FIG. 2a. An order of magnitude stronger near-field intensities than those of individual antennas are observed at slightly shorter wavelengths than $\lambda_{Si(1,0)}$. Here, $\lambda_{Si(1,0)}$ is the critical wavelength where the (1,0) grating order of the silicon interface becomes radiative at a given lattice periodicity ($\lambda_{Si(1,0)} = n_{Si}d$). This collectively enhanced near-field behavior is reflected as a narrowing of the far-field spectral response due to the suppression of the radiation damping with the confinement of the electromagnetic field within the array (Lamprecht et al., (2000) Physical Review Letters 84:4721-4724).

Figure 3A:
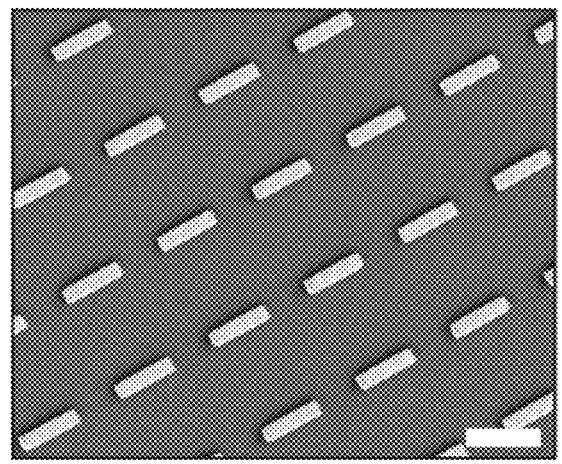
FIGS. 3A-3C shows the spectral characteristics of the periodic nanorod arrays.
Figure 3B:
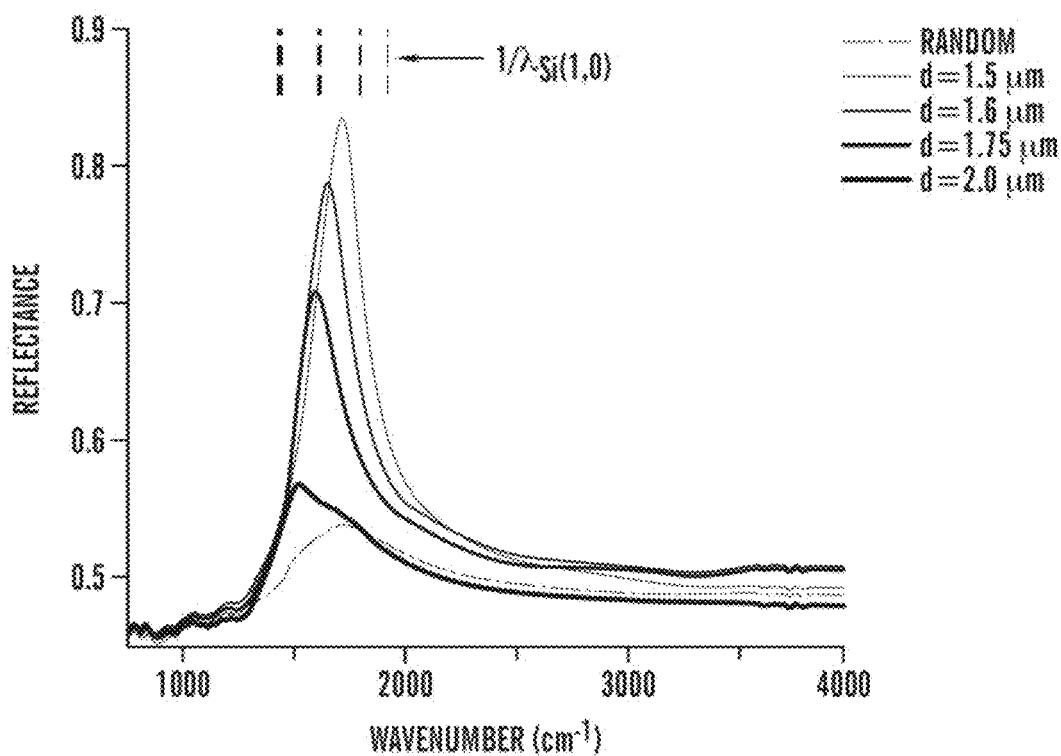
Figure 3C:
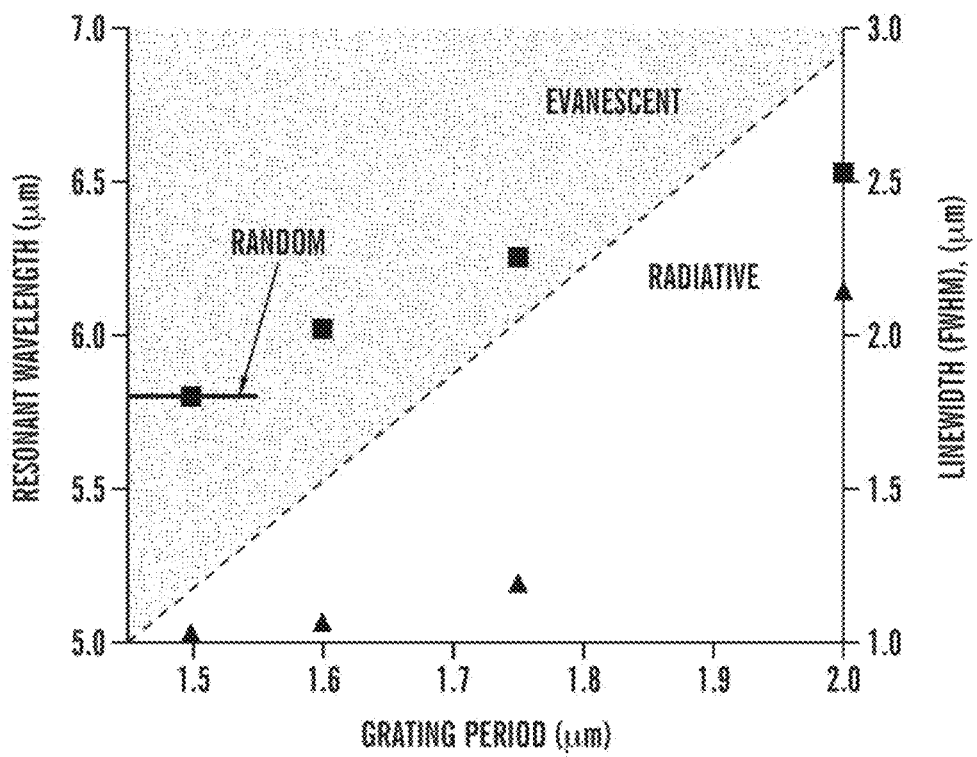

To enhance absorption signals, arrays are optimized using far field reflectance measurements by spectrally tuning the narrow resonances to the protein vibrational bands. FIG. 3a shows an SEM image of a fabricated periodic array of rod shaped antennas. The arrays consist of 1100 nm long rods with varying periodicities ranging from 1.5 µm to 2.0 µm, as well as a random set that serves as a control to probe the individual antenna response. The resulting reflectance spectra are shown in FIG. 3B. For periodicities smaller than 2 µm, collective resonance peaks are above the (1,0) grating order cutoff of the silicon interface (dashed line in FIG. 3C) where the field is evanescent (d<$d_c$). This results in narrower plasmonic far field resonances with respect to individual nanoantenna as shown in FIG. 3C. A progressive blue shift is expected for greater separations as the coupling among antennas is reduced, and the optical response converges back to that of an isolated particle. For d>$d_c$, the grating order field changes from being evanescent to radiative form in nature which is associated with strong damping of the collective resonance and broadening of the line-width. In fact, at 2 µm periodicity, resonance occurs at a wavelength below the grating cut-off (d>$d_c$) and results in a broader linewidth. In comparison with the randomized arrays, the arrays with 1.5 µm and 1.6 µm periodicities have significantly narrower resonance line-widths (~1 µm versus 2.75 µm for the individual particle behavior). As shown in FIG. 3C, the 1.6 µm periodic array offers the best combination of narrow line-width and spectral overlap with the protein amide-I band at 1660 $cm^{-1}$.

Example 3

SEIRA Enhancement by Collective Resonances

Direct identification of the vibrational signatures of the protein monolayers is achieved by utilizing this collective excitations. Here, the protein layer is applied to the nanoantenna array surface by uniform spin coating of a thin film of silk fibroin (as described in the material and methods section herein). As mentioned before, a unique advantage of silk is that it allows fine control over the protein film thickness by varying its concentration in solution (Omenetto et al., (2008), Nature Photonics. 2:641-643). Homogeneous films were coated on the nanorod antenna array as thin as 2 nm, corresponding to essentially a single protein monolayer. Atomic force microscopy (AFM) is used to confirm the uniformity and the thickness of the film. Initially, the scanning of the tip is performed in contact mode to scratch away the film down to the silicon support. Subsequent measurements at reduced force are then used to determine the film thickness (FIG. 4A). A combination of AFM and profilometer measurements confirmed the linear dependence of the film thickness on solution concentration.

Figure 4B:
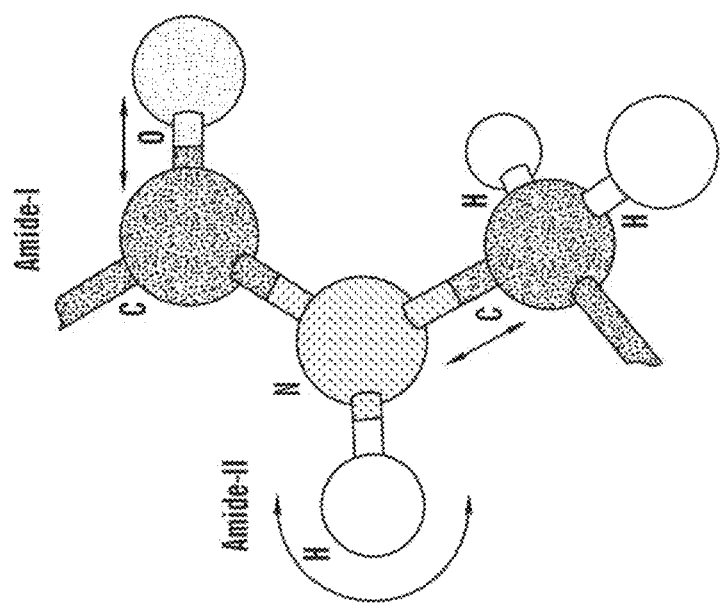
FIG. 4B shows amide-I and amide-II vibrational modes of the protein back bone.
Figure 4A:
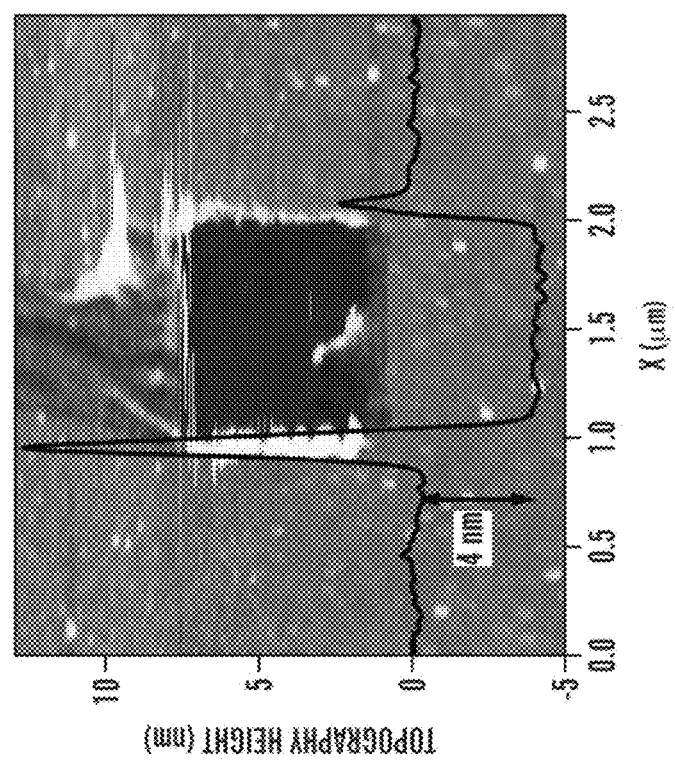
FIG. 4A shows the CEIRA signal of silk films.
Figure 4D:
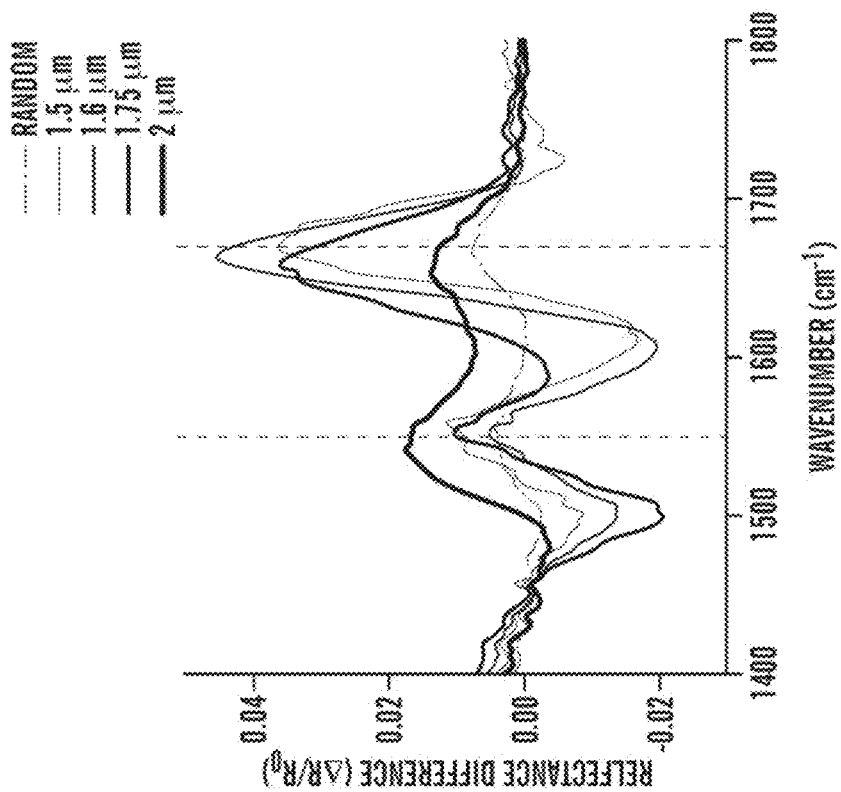
FIG. 4D shows difference absorption spectra of the arrays whose spectral characteristics before protein coating are given in FIG. 3B.
Figure 4C:
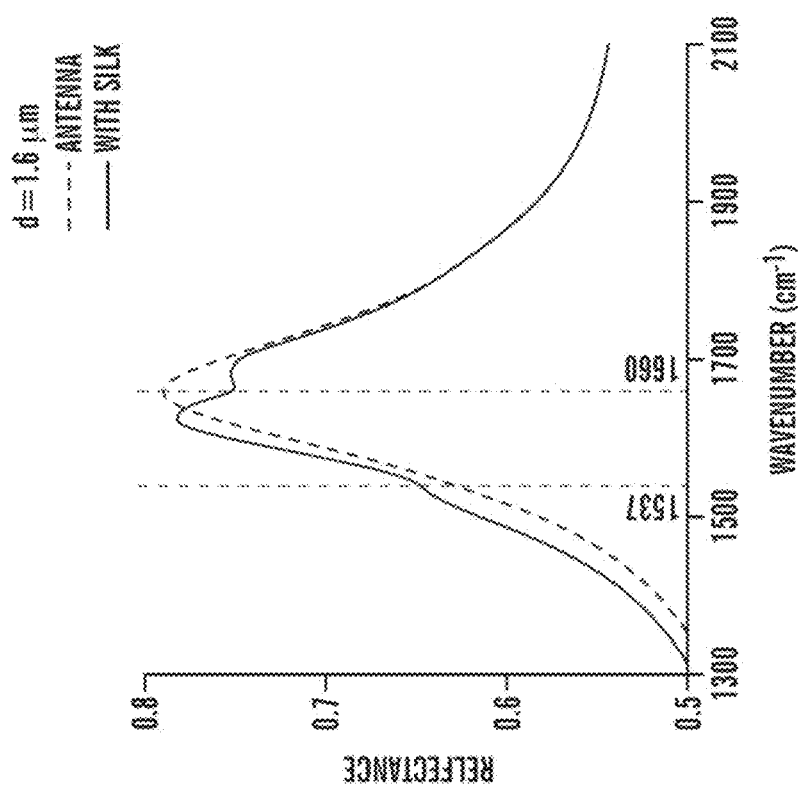
FIG. 4C shows the reflectance spectra from the 1.6 µm periodic array before (dashed line) and after coating of 2 nm thick protein film (solid line). Dashed vertical lines indicate the positions of the protein amide-I and II absorption peaks.

As shown in FIG. 4B, protein absorption bands are clearly noticeable within the optical spectra collected from the protein-coated antenna arrays with 1.6 µm periodicity. Dips in the plasmonic response as a result of the amide I and II absorption bands are indicated in the figure at 1660 and 1537 $cm^{-1}$, respectively. Capacitive loading of the antenna with the protein layer results in slight red shifting of the plasmonic resonances (Alu et al., (2008), Nature Photonics. 2:307-310; Schnell et al., (2009), Nature Photonics. 3:287-291) (dashed curve in the figure). This shift is corrected using a polynomial fitting procedure in difference spectrum measurements ($\Delta R/R_0 R = R_{before}/R_0 - R_{after}/R_0$, where $R_0$ is the reflection signal from reference mirror). FIG. 4C demonstrates the difference spectra of the periodic and the randomized arrays. The enhanced absorption signals well above the noise level are observed for the antenna arrays with narrow line-width (1.6 µm periodicity). Control measurements were performed on the bare silicon support with protein films of the same thickness in a region far from any fabricated nanoantennas. No absorption features were observed from the control samples. The observed signal ($\Delta R/R_0$) of 6.8% in the periodic structures is nearly an order of magnitude higher than that of the randomized array, where the difference signals were 0.9%. This observation is in agreement with the enhanced near-field intensities predicted by the FDTD simulations (FIG. 2A).

In order to calculate the near-field enhancement factor, we compared the "enhanced" signal collected from the 1.6 µm periodic array to the expected reflectance signal from a 2 nm thick silk film on bare silicon support. Since the signal from protein films on bare silicon is below the noise level, instead we performed IR reflection absorption spectroscopy (IR-RAS) measurements to obtain the expected value of the absorption signal for a normally incident light. The frequency dependent dielectric function of the silk film was experimentally determined by fitting the measured IRRAS signal to a Lorentzian oscillator model (Tolstoy et al., (2003), Handbook of Infrared Spectroscopy of Ultrathin Films (John Wiley & Sons Inc, Hoboken, N.J.), pp. 243-286). For a thin film (i.e. t<<λ) deposited on a metal support, the reflectance signal is approximately given by (Enders D & Pucci A (2006), Applied Physics Letters 88:184104):

$$\frac{R(\theta)}{R_0(\theta)} \approx 1 - 4t\frac{\omega}{c}\frac{\sin^2\theta}{\cos\theta}\text{Im}\left\{\frac{-1}{\varepsilon_2}\right\}, \quad (10)$$

where, $\theta$ is the angle of incidence, t is the film thickness and $\varepsilon_2 = \varepsilon_{2,Re} + i\varepsilon_{2,Im}$ is the dielectric function of the silk layer. IRRAS measurements are performed at a grazing angle (80°) for 2 nm thick protein film coated on a 100 nm thick gold layer deposited on a silicon support. The incident light was polarized in the plane of incidence. The resonant frequencies, oscillator strengths and full-width half maxima of the Lorentz oscillator model for $\varepsilon_2$, $$\varepsilon_2 = \varepsilon_\infty + \sum_{j=1}^{m} \frac{S_j}{\omega_{0,j}^2 - \omega - i\omega\gamma_j} \quad (11)$$

were varied in order to obtain a fit with the data using Eq. 3. An estimated difference absorption signal of $4.7\times10^{-2}\%$ is obtained by using three-layer Fresnel equations and $\varepsilon_2$ fitted through the IRRAS measurements. For an accurate estimate of the enhancement factor, the following factors were determined (see discussion related to "Dipole interaction matrix" as disclosed herein). The enhanced signal mainly comes from a small quantity of molecules at the close vicinity of the $N^2$ nanorod tips (N=63 is the number of rows and columns). Secondly, in contrast to the studies conducted with self-assembled monolayers (SAMs) (Osawa M, et al, (1991) J. Phys. Chem. 95:9914-9919; Jensen et al., (2000). Applied Spectroscopy 54:371-377; Williams et al., (2003) J. Phys. Chem. B 107:11871-11879; Enders D & Pucci A (2006) Appl. Phys. Letts. 88:184104; Kundu J, (2008) Chemical Physics Letters. 452:115-119; Neubrech et al, (2008) Phys. Rev. Letts 101:157403; Bukasov et al., (2009) Analytical Chem. 81:4531-4535), here the protein molecules are physisorbed (see FIG. 9) which results in the following differences. (i) Unlike the SAMs, the transition dipole moments of the physisorbed proteins have no fixed orientation with respect to the metal surface normal. Accordingly, expect that approximately one third of the transition dipoles of the molecules at the nanorod tips contribute to the absorption signal (see discussion related to "Dipole interaction matrix" as disclosed herein). (ii) Additionally, unlike in chemisorption, lack of molecular binding to the metal surface rules out any contribution of the chemical effects. (iii) Finally, given that the silk film is only 2 nm thick, it is unlikely that the physical deposition method results in the same degree of uniform coverage over the 70 nm high vertical sidewalls of our nanorods as would be possible with a SAM method. With these in consideration, the estimated the signal enhancement to be within the range of $10^4$-$10^5$ (see discussion related to "Dipole interaction matrix" as disclosed herein). Such large enhancements allow us to detect absorption signals even in the raw spectral measurements from monolayer protein films with a commercial FTIR microscope. The detection volume of the antenna was calculated by considering the lateral area of the nanotips and the thicknesses of the monolayer protein film. Given that the density of the protein is 1.4 g/cm$^3$ (Warwicker (1954), Acta Crystal; 7:565-571.) and the molecular weight is approximately 375 kDa (Sashina et al., (2006) Russian J. Appl. Chem. 79:869-876), the inventors estimate that the measured absorption signals are obtained from about 300 zepto-moles for the entire array, corresponding to only 145 silk molecules per antenna (see Materials and Methods section). The large signal to noise ratios achieved in our measurements indicate that we should be able to observe vibrational signatures from even smaller quantities of protein molecules down to a few tens of zepto-moles.

Figure 5A:
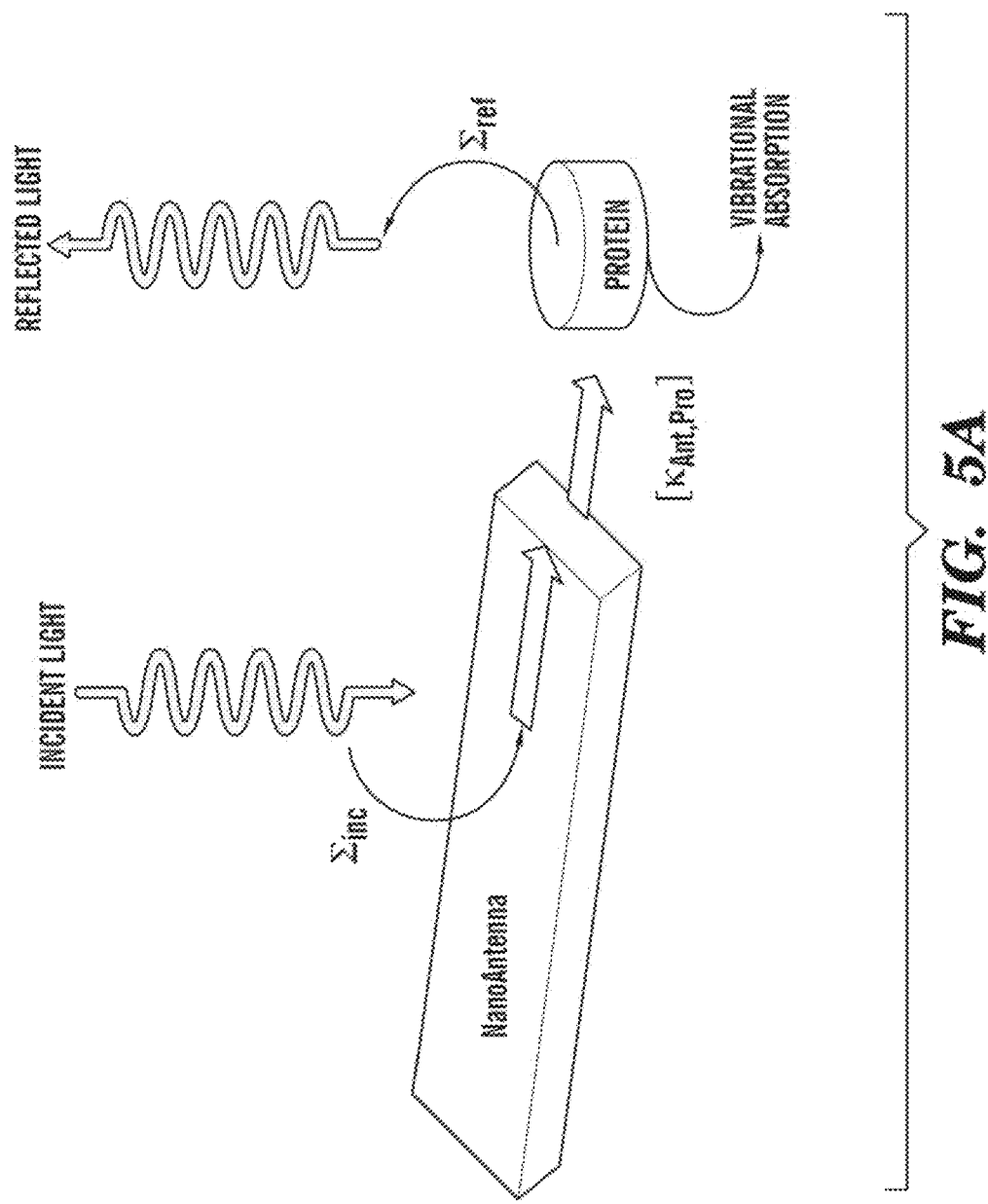
FIGS. 5A-5C is a schematic illustrating the model.
Figure 5C:
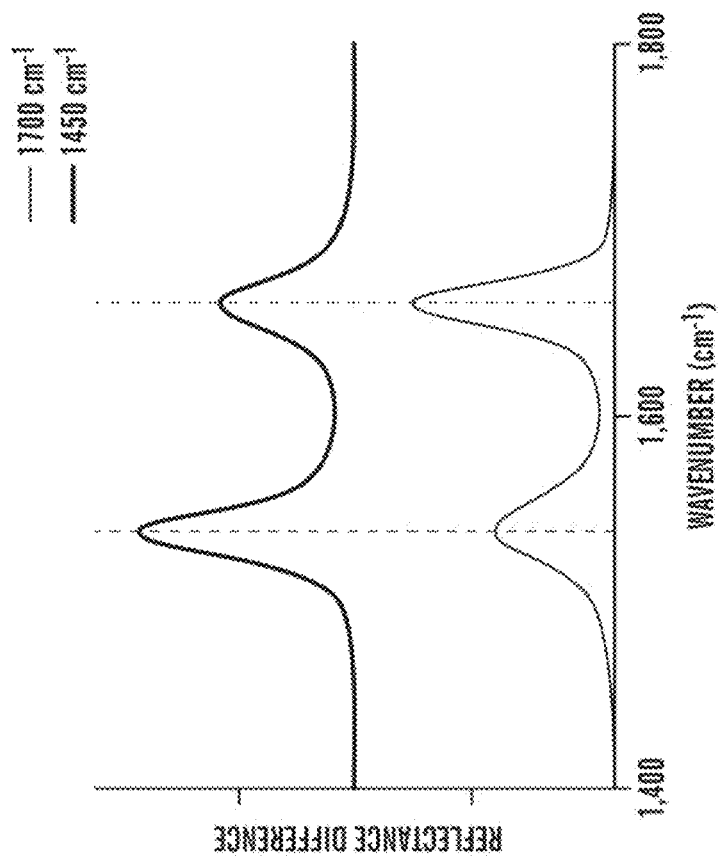
Figure 5B:
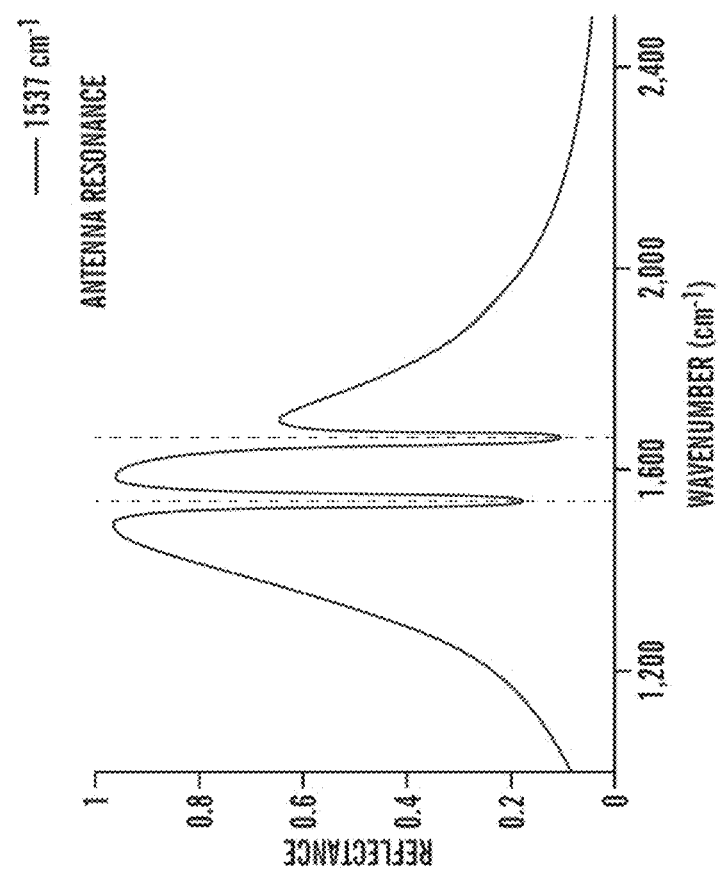

In addition to the strong enhancements observed for the collective resonances, variations in the absorption lineshapes as the spectral overlap were observed between the antenna resonances and those of the protein amide bands are varied. This experimental observation can be explained using a model based Non-Equilibrium Green's Function formalism which has been successfully applied in molecular/nano-electronics (Yanik et al., (2007); Phys. Rev. B 76:045213; Datta S et al., (2004); Nanotech. 15:S433-S451). The strength of the NEGF formalism is that it provides a natural framework for describing the wave nature of the elementary excitations (electrons, phonons, vibrons, etc) in the presence of incoherent and dissipative processes. Conceptually, the system is partitioned into a nanoantenna and a protein load driven by the excitation of the plasmonic resonances as shown in FIG. 5A. Direct absorption of the incident light by the protein load is neglected since this absorption is expected to be very weak. The coupling of the incident light to the nanoantenna is expressed using a self energy matrix [$\Sigma_{inc}$] whose anti-Hermitian component $\Gamma_{inc}$= [$\Sigma_{inc}$−$\Sigma_{inc}^+$] is the broadening of the plasmonic antenna resonance due to the radiative coupling. Vibrational absorptions of the molecules are incorporated into the antenna/ protein Hamiltonian [$H_{Ant+Load}$] using a coupling matrix [$\kappa_{Ant-Pro}$]. This matrix is designed to give unit transmission in spectral regions far from the absorption bands. A combination of Lorentz oscillator dips in the matrix strength are employed to account for the absorption bands at the spectrally related regions. Reflected light is calculated through the second self energy term [$\Sigma_{ref}$] with $\Gamma_{ref}$=[$\Sigma_{ref}$−$\Sigma_{ref}^+$], which takes into account the open boundary condition in a similar fashion to the perfectly matching layers (PML) used in FDTD simulations. Reflected light intensity is obtained by R=tr($\Gamma_{inc}G_{Ant+Load}\Gamma_{ref}G_{Ant+Load}^+$). Here, [$G_{Ant+Load}$]= $[(\hbar\omega)I - H_{Ant+Load} - \Sigma_{inc} - \tau_{ref}]^{-1}$ is the Green's function of the antenna/protein system coupled to the open boundaries and [I] is the identity matrix. Retarded Green's function [$G_{Ant+Load}$] is a frequency dependent non-Hermitian matrix incorporating complex self-energy terms through which the radiative/non-radiative decaying of the plasmonic excitations are taken into account. The model absorption lines are defined as Lorentz oscillators at 1660 cm$^{-1}$ and 1537 cm$^{-1}$ with a width of 30 cm$^{-1}$. As shown in FIG. 5B, for the amide-II band, when there is an exact match between the plasmonic antenna resonance and the absorption band, the spectral lineshape is Lorentzian. For slightly detuned absorption resonance, as such for the amide-I, an asymmetric Fano type line-shape is clearly noticeable. The relative strength of the absorption resonances is due to the relative coupling strength of the incident infrared radiation to the protein vibration band. As expected, with the detuning of the antenna resonance the relative absorption strength of the vibration bands can be modulated (inset in FIG. 5C).

Example 4

Silk Film as a Near-Field Probe

Figure 6A:
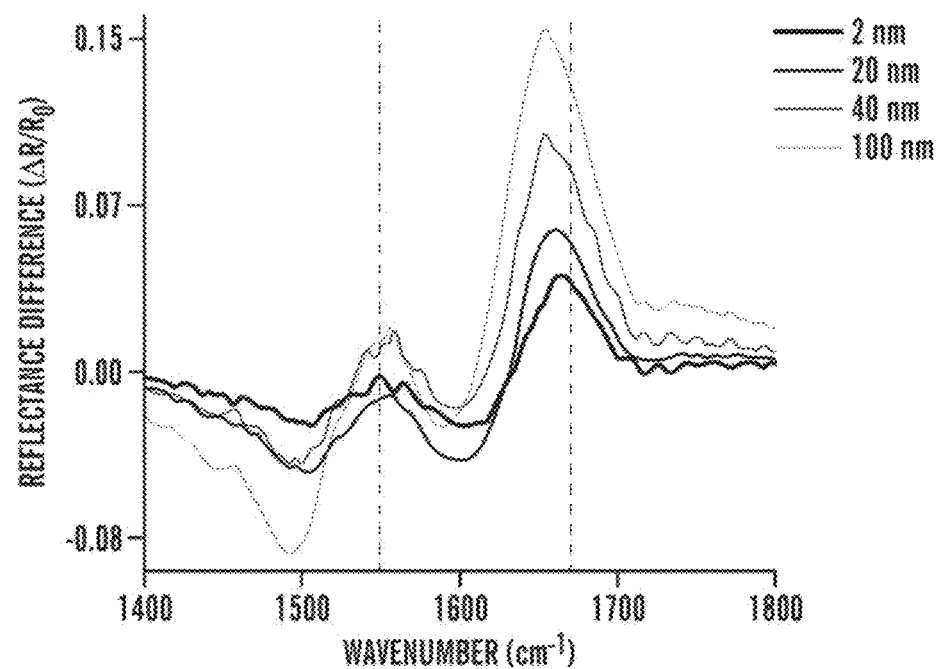
FIGS. 6A-6B shows silk as a near-field probe.
Figure 6B:
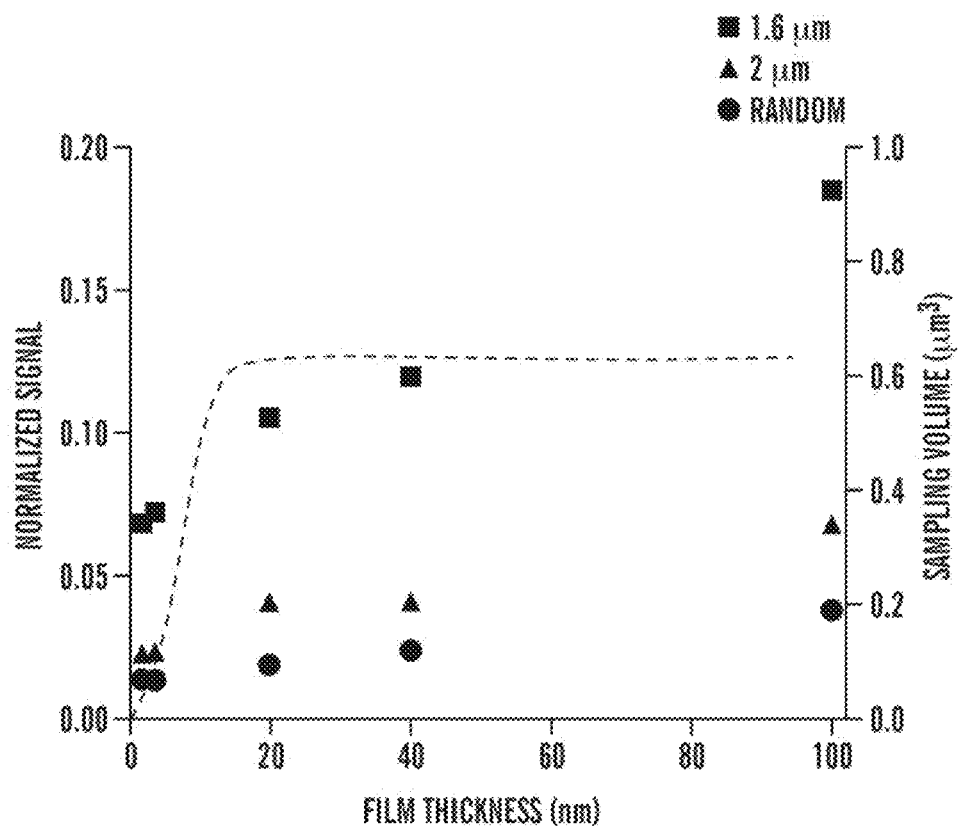

The ability to control the thickness of the silk protein films from several nanometers to several microns provides a unique opportunity to probe the near-field behavior of the nanorod antenna. Due to the rapid decaying of the strongly enhanced near-fields with distance from the nanorod surfaces (as can be seen in the FDTD simulations in FIG. 2A), saturation of the enhancement is expected to occur for films as thin as 40 nm. While the numerical calculations offer insight into this observation, the inventors used silk films as a near-field probe and experimentally demonstrate the surface nature of the enhancement by varying the film thicknesses (2, 4, 20, 40 and 100 nm) on identically patterned nanoantenna arrays. FIG. 6A shows the difference absorption spectra for the 1.6 μm periodic array with L=1100 nm. Measurements are also taken from a periodic structure with 2 μm periodicity and a randomized array for the same rod length. The strength of the absorption signal (amide-I) is plotted as a function of the film thickness in FIG. 6B for all the structures (signals are normalized to take into account the difference of nanoantenna numbers in each array). Enhancement in the absorption signal strength is significant with increasing protein film thickness from 2 to 20 nm, but it appears to saturate as the thickness reaches to 40 nm. This behavior is in contrast to a steady linear dependence one would expect from Beer-Lambert's law for very thin films (see discussion related to "Dipole interaction matrix" as disclosed herein for details). Beyond 100 nm film thickness, bulk infrared absorption signals from thick protein films become observable. The other critical observations in FIG. 6 are as follows. Both of the periodic arrays with collective resonance display markedly higher signals than the randomized arrays, in agreement with the discussion presented above. The consistency of the data from periodic samples emphasizes the repeatability of the CEIRA measurements on the lithographically patterned supports. Finally, experimentally measured enhancement saturation resulting from decaying near-field intensity distribution is confirmed by numerically calculating sampling volumes (for the 1.6 μm periodic array). For a given silk film thickness, t, the volumes are computed from the FDTD by summing over the simulation grids, which are within a distance t from the rod surface and have a near-field intensity greater than $1/e^2$ of the average maximum. The agreement between the calculated mode volumes and the absorption signal saturation strongly emphasizes the surface nature of the CEIRA effect.

Herein provides a nanoantenna array for use in a surface enhanced spectroscopy technique (CEIRA), were the nanoantenna array comprising a redefined pattern of nanoantennas (or plasmonic nanostructures) results in collective plasmonic excitations, which is created by tailoring of the dipolar interactions by specific shapes and spatial organization of the nanoantennas on in the engineered nanoantenna arrays. Up to $10^5$-fold enhancement of vibrational/absorptional signatures of the monolayer thick protein films is obtained with high signal to noise ratios. In particular, the nanoantenna arrays as disclosed herein have been demonstrated to be useful for the detection of 300 zepto-moles of proteins for the entire nanoantenna array, corresponding to only 145 molecules per antenna. With progressive loading, the near-field plasmonic behavior of the metallic nano-rod antenna was resolved. The inventors also developed a Greens function model which explains the experimentally observed asymmetric absorption spectra due to the detuned coupling between the plasmonic excitations and the molecular vibrations.

Example 5

Nanoantenna Arrays with Embedded Plasmonic Nanostructures

The inventors have also surprisingly discovered that significantly longer plasmon lifetimes and stronger near-field enhancements can be achieved by embedding the plasmonic nanostructures, such as the nanoantennas into the support of the nanoantenna array. The inventors demonstrated that embedding the plasmonic nanostructures, such as the nanoantennas in the same plane, or below the surface of the support results in a more homogeneous dielectric background, allowing stronger diffractive couplings among plasmonic particles leading to strong suppression of the radiative damping. Using embedded plasmonic nanostructures, such as the nanoantennas, results in near-field enhancements well beyond than those achievable with isolated nanoparticles. Such nanoantenna arrays, including those with raised or embedded plasmonic nanostructures enhances fields obtained in these structures and are useful for biosensing and non-linear photonics applications.

The inventors demonstrate further improvements in the near-field enhancements/line-widths by embedding the plasmonic nanostructures in a nanoantenna array beneath the surface of the support. Far-field extinction measurements confirm the strong diffractive coupling between the particles and the resulting narrow plasmonic lineshapes. Numerical modeling using the three dimensional Finite Difference Time Domain (3D-FDTD) method (see CST Microwave Studio, Computer Simulation Technology, Darmstadt, Germany, at world-wide-web at "cst.com") indicates that strong near-field enhancements complement these sharp extinction features.

Figure 10A:
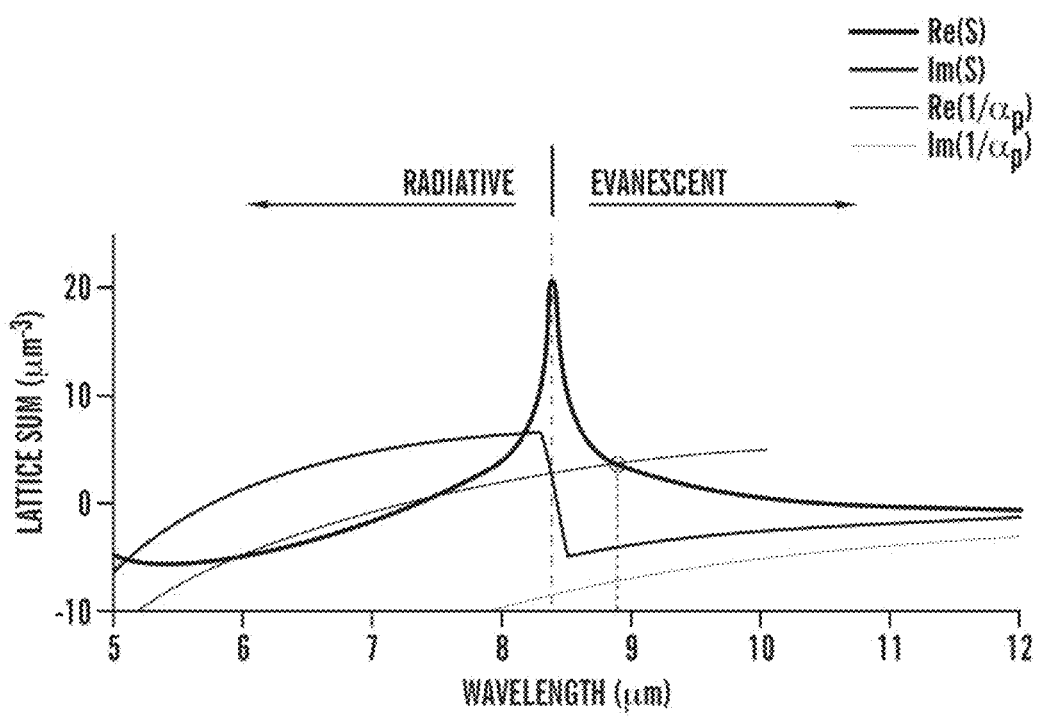
FIGS. 10A-10D show the narrow extinction resonances in periodic arrays of nanoparticles.

In FIG. 10A the nanoparticle polarizability, $\alpha_p$, and the retarded dipole sum, S, are shown with respect to the wavelength of the incident light, which is normally incident and polarized perpendicular to the chain axis (along the long axis of the nanorods). The particles are modeled as gold ellipsoids, with the dielectric function computed from a Lorentz-Drude model (Rakic, et al., Appl. Opt. 37, 5271-5283 (1998); Palik, et al., Handbook of Optical Constants of Solids II (Academic, Orlando, Fla., 1985)). In order to account for the finite size of the particle, $\alpha_p$ is computed using the modified long wavelength approximation (MLWA) (Meier et al., Opt. Lett. 8 581-583 (1983); Jensen, J. Clust. Sci. 10 (1999)). Computation of S involves evaluating an infinite summation. This was done numerically with the sum terminated at N=400 particles.

As shown in FIG. 10, the real part of the inverse nanoparticle polarizability (e.g., $Re(1/\alpha_p)$) monotonously increases starting from a negative value and crosses to the positive domain at the LSPR wavelength of a single nanoparticle. The lattice sum, S, shows a more complex behavior. For large particle separations, $C_{ij}$ is dominated by the far-field term which is a real positive number. Hence, for a periodic chain, the real part of the lattice sum S (red curve) diverges at the diffraction condition ($kr_{ij}=2\pi m$) (Zou et al., Nanotech. 17, 2813-2820 (2006); Markel et al., J. Phys. B: At. Mol. Opt. Phys. 38, L115-L121 (2005); Lamprecht et al., Phys. Rev. Lett., 84 (2000); Auguié et al., Phys. Rev. Lett. 101, 143902 (2008)). This is visible as a sharp maximum in the figure at the grating transition wavelength (dashed vertical line). Im(S) (see FIG. 10A) exhibits a rapid sign change around this grating transition wavelength. Imaginary part of the lattice sum, Im(S), is positive (negative) when the grating order is radiative (evanescent) resulting in increased (decreased) radiative damping. The sudden appearance of the new grating order causes a dramatic increase in the radiated power from the array, which is closely associated with the Wood anomalies and Rayleigh's explanation (Rayleigh, Proc. Royal Soc. London A, 79 399-416 (1907)). As shown in FIG. 10A, cancelation of the real terms in the dominator in Eq. (10) occurs at a wavelength (dotted vertical line) slightly longer than the grating transition wavelength, where the real part of $1/\alpha_p$ (see FIG. 10A) crosses the real part of lattice sum (ReS) as indicated by circle in FIG. 10A. A maximum both in the imaginary and the modulus of the particle's complex polarizability (corresponding to resonance in extinction spectrum) is observed at this crossing wavelength, which is slightly red-shifted from the LSP resonance of the individual nanoparticle. More interestingly, the imaginary part of S is negative at the array resonance wavelength (FIG. 10A) and partially cancels the imaginary parts of $1/\alpha_p$ (Im $1/\alpha_p$ in FIG. 10A). This partial cancellation results in linewidth narrowing of the far-field extinction resonance and longer plasmon lifetimes due to the suppression of the radiative damping. With increasing plasmon lifetimes, enhanced intensities in the near-field are expected as a result of field confinement in the array plane. In well engineered arrays, significant improvements in plasmon lifetimes (Lamprecht et al., Phys. Rev. Lett., 84 (2000)) and near-field enhancements are possible (Adato et al. Proc. Nat. Acad. Sci. USA 106 19227-19232 (2009).)

For extended plasmon lifetimes and enhanced near-fields, an important consideration is that dipolar couplings among nanoparticles should be through a homogeneous dielectric background (Auguié et al., Phys. Rev. Lett. 101, 143902 (2008), Bendaña et al., Opt. Express 17 18826-18835 (2009)). In practice, however, nanoparticle arrays are fabricated on supports. For light propagating above and below the support, this refraction index mismatch results in different phase velocities and conditions for constructive interference. Even then, significantly narrower far-field extinction resonances, enhanced near-fields (Adato et al., Proc. Nat. Acad. Sci. USA 106 19227-19232 (2009)) and extended lifetimes (Lamprecht et al., Phys. Rev. Lett., 84 (2000)) are observed in arrays where the nanoparticles are fabricated on a support (FIG. 11B)). However, further improvements in collective plasmonic characteristics can be achieved for arrays buried in a homogeneous background. The embedded particle geometry proposed in this article (FIG. 11) provides a largely homogeneous dielectric environment to overcome the large index mismatch limitation in conventional particle arrays.

Although index matching oils can be used to obtain a homogeneous background in experiments aimed at investigating the basic physics of the collective resonance effect (Auguié et al., Phys. Rev. Lett. 101, 143902 (2008)), the embedded geometry proposed here offers several practical advantages. Firstly, greater freedom in the choice of support is possible, as the range of refractive indices of index matching oils is limited. This is an important consideration at the mid-infrared frequencies examined here where the support is silicon, with a refractive index of 3.46. Regarding biomolecule detection applications, care must be taken that the fluid used is hospitable to biological substances. This is not a concern in the embedded geometry. Finally, where enhancement in the support is desired, e.g. for photovoltaic and nonlinear photonic applications, the embedded geometry offers a clear advantage as will be shown with FDTD simulations.

Example 6

Fabrication of Nanoantenna Arrays with Embedded Nanostructures and Measurement

Figure 11A:
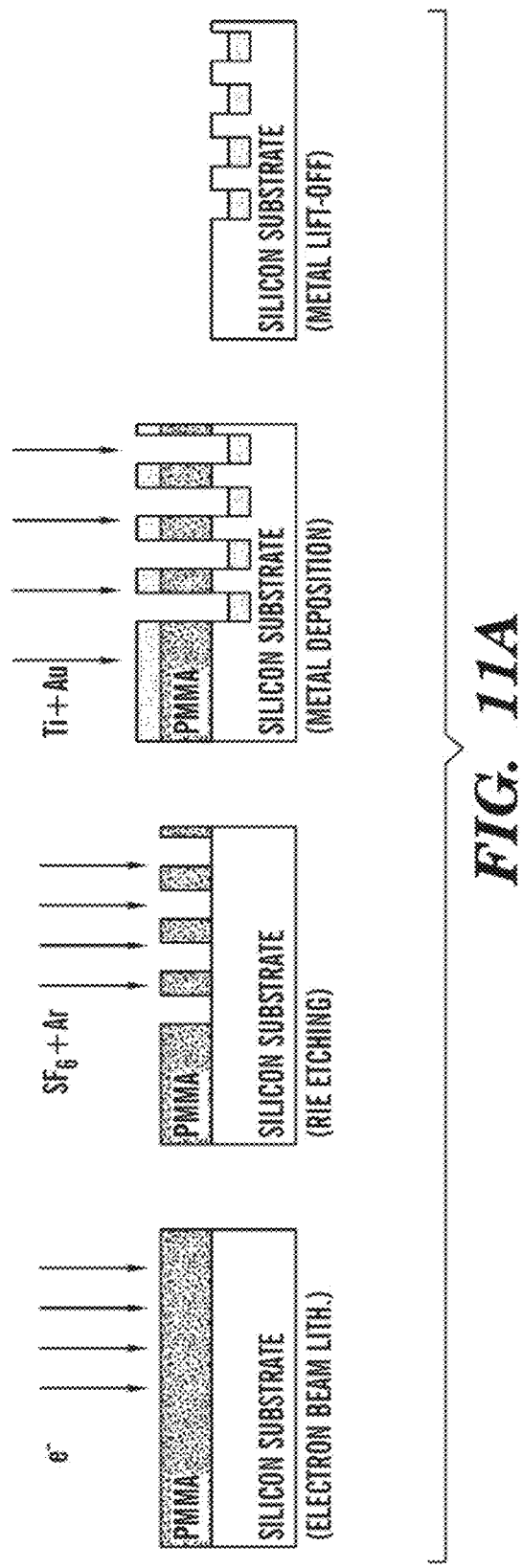
FIGS. 11A-11D show embodiments for different embedded nanostructure geometry and fabrication of nanoantenna arrays with embedded nanoantennas (e.g., embedded nanostructures).
Figure 11B:
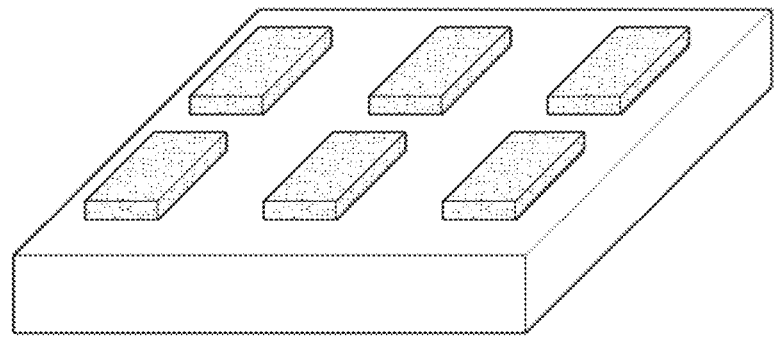
Figure 11C:
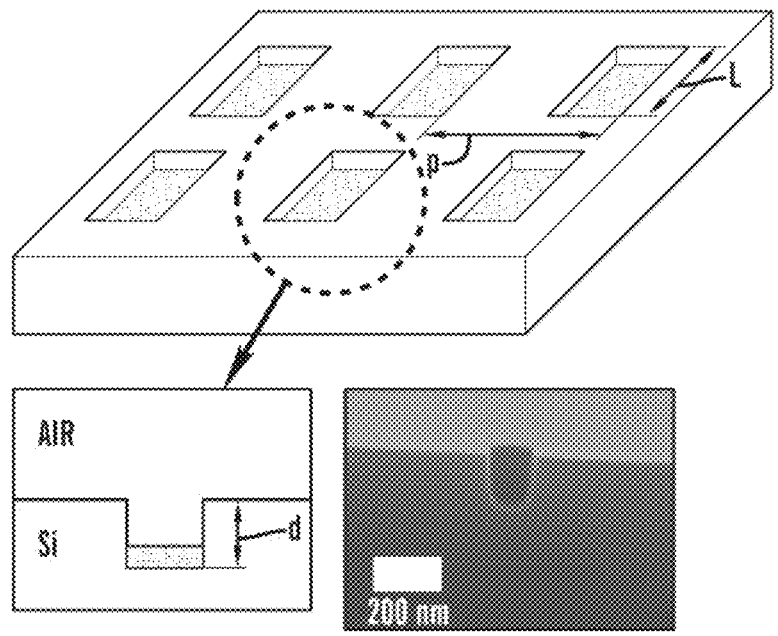
Figure 11D:
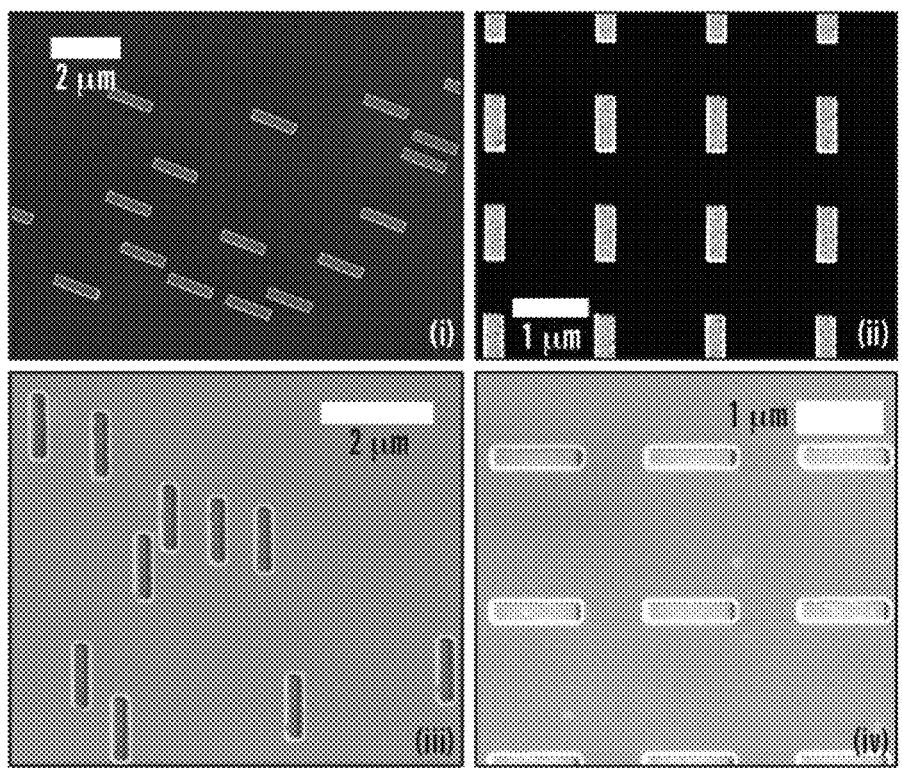

A fabrication scheme was established to embedded the nanostructures in the array support for a homogenous dielectric background as summarized in FIG. 11A. One can use any fabrication method, although one can also use a single layer e-beam lithography, reactive ion etching (RIE) and a following lift-off process. We start by performing e-beam lithography on silicon supports using a positive e-beam resist poly(methylmethacrylate) (PMMA). The nanohole pattern is transferred to the silicon support by a dry etching process using PMMA as a mask. The scanning electron microscope (SEM) image of a cleaved sample in the inset of FIG. 11C shows that etching is directional with vertical side-wall profile. The etch depths examined here is 200 nm. Before the removal of the PMMA mask, a directional e-beam metal deposition is performed with a thin Ti (5 nm) adhesion and Au (95 nm) metal layers. Lifting off the remaining resist results in well formed nanorods effectively buried beneath the support surface as shown in FIG. 11D (iii-iv). On support particle arrays are also fabricated (FIG. 11D (i-ii)) to compare the effect of the homogenous versus inhomogeneous background on the collective resonances.

In order to characterize the resonant behavior of the nanoparticle arrays, we perform transmission measurements using an IR microscope and Fourier Transform Infrared (FTIR) spectrometer. Spectra are collected over the wavelength region of 1.67-15.38 μm (6000-650 cm-1) using a Mercury Cadmium Telluride (MCT) detector. Polarized light is incident on the particle array from the support side and collected with 0.4 NA, 15× reflection optics objectives. The fabrication method and the experimental conclusions as disclosed herein (implemented in mid-infrared spectral regime) can be readily extended to visible and near-infrared frequencies by using an appropriate etching processes on a desired support. The method of fabrication typically results in air holes (e.g., voids) above the embedded particles. In some embodiments, these voids can be filled with an appropriate wavelength permeable or penetratable material. As demonstrated herein using FDTD analysis, the effect of the air holes is not significant. In fact, near-field distribution of the embedded rods is found to be similar to that of a particle in a fully homogeneous background.

Example 7

Individual Particle Resonances from Embedded Nanostructures

To obtain plasmon resonances in the mid-infrared spectral region, the inventors fabricated rod shaped particles, which support resonances similar to those of an ideal dipole antenna at wavelengths given by (Crozier, et al., J. Appl. Phys. 94, 4632-4642 (2003); Cubukcu et al., Appl. Phys. Lett. 95, 201101 (2009); Novotny, Phys. Rev. Lett. 98, 266802 (2007)).

$$\lambda_{Res} = (2n_{eff}/m)L + C. \qquad (11)$$

Here, L is the rod length, $n_{eff}$ is the refractive index of the dielectric background and m is an integer corresponding to the order of the plasmonic standing wave pattern on the surface of the rod. C is a fitting parameter due to the finite width of the nanorods, which is $C \approx 4Rn_{eff}/m$ for a cylindrical rod with cross sectional radius R and hemispherical ends (Cubukcu et al., Appl. Phys. Lett. 95, 201101 (2009); Novotny, Phys. Rev. Lett. 98, 266802 (2007)). In order to determine the individual particle response, we fabricated large arrays of randomly (but consistently oriented) particles. The random arrangement cancels out any consistent coupling among nanoparticles and allows the individual particle response to be measured at high signal to noise ratios in an interferometer [Adato et al., Proc. Nat. Acad. Sci.

USA 106 19227-19232 (2009), Yanik, et al., Appl. Phys. Lett. 93, 081104 (2008)). In order to obtain consistent particle geometry throughout the random arrays, the pattern was designed to ensure that all particles were separated by at least 200 nm edge to edge. This prevented particle overlap and allowed a clean lift-off process. Experiments have shown that the array design does not affect the position of the resonance peaks (Adato et al., see the supporting information at world-wide-web at "pnas.org/content/106/46/19227/suppl/DCSupplemental"), confirming a faithful measurement of the individual particle behavior. Spectral response of the resonance transforms to a Gaussian line-shape as the effects of particle coupling in a periodic pattern are replaced with randomly phased dipolar interactions (Adato et al. see the supporting information at world-wide-web at "pnas.org/content/106/46/19227/suppl/DCSupplemental", Auguié et al., Opt. Lett. 34 401-403 (2009)).

The lithographically patterned rods are highly rectangular, with constant heights of 100 nm, and widths of 300 nm. The rod length, L, was the only parameter of the particle geometry varied in the experiments. The linear dependence of the resonant wavelength on the rod length is clearly evident in our experimental data for m=1 and m=3 modes, as shown in FIG. 12A. Here, the mode corresponding to m=2 is missing due to the absence of a dipole moment required to couple the incident light to this excitation. For the m=1 mode, a close fit to the dipolar antenna behavior using Eq. 11 is observed for an effective refractive index of $n_{eff}$=3.11 (dashed black curve). Similarly, for the m=3 mode, fitting of the experimentally observed resonance wavelengths to the dipolar antenna formula resulted in $n_{eff}$=3.09 (dashed blue curve).

Figure 12B:
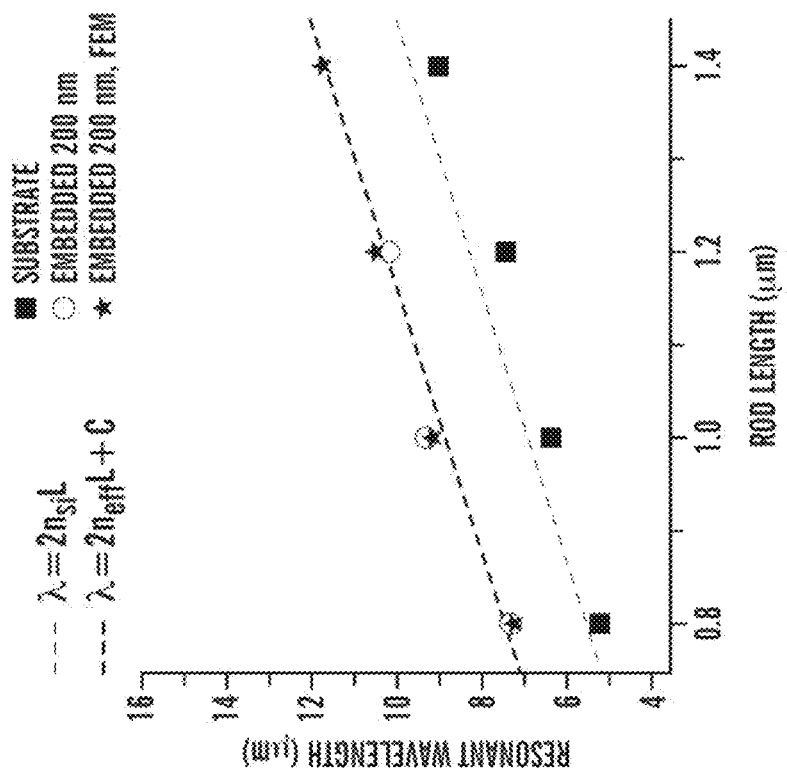
FIGS. 12A-12B shows the difference of resonance of an embedded or an on-support (e.g., raised) nanostructure.
Figure 12A:
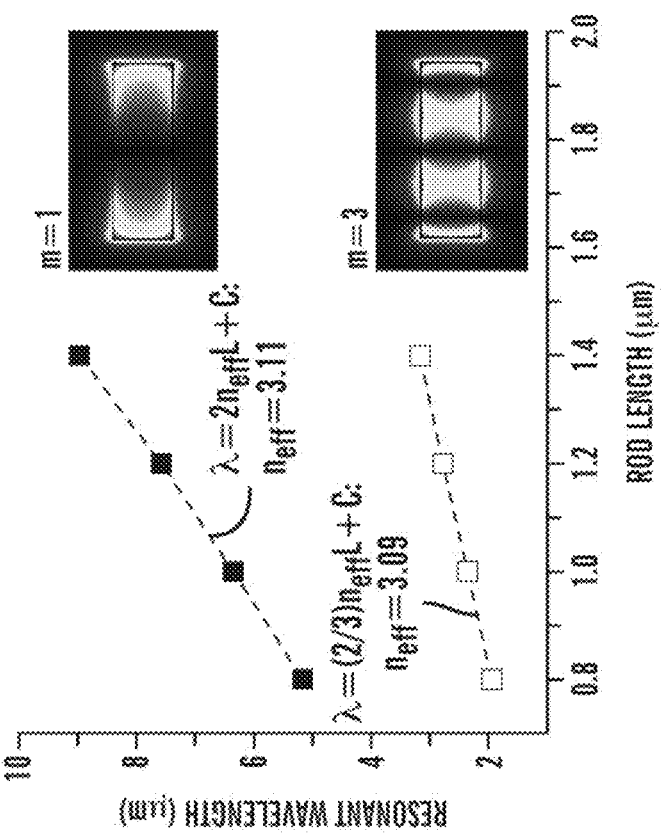

In FIG. 12B, the effect of the embedding procedure on the single particle for m=1 order resonance is illustrated. Resonance wavelengths are shown for varying rod lengths and compared for on-support and 200 nm deep embedded rods. The resonant wavelengths for the embedded rods are strongly red-shifted in comparison with those deposited directly on the Si support. In addition, they deviate from those expected for an ideal half-wave dipole antenna in a Si dielectric background (Eq. (11) with C=0 indicated by green dashed line). To confirm this observation, Finite Element Method (FEM) simulations (black stars) was performed. Experimentally observed peak positions are in very good agreement with our FEM calculations. A linear fit to the FEM data using Eq. (11) results in values of 3.51 and 1.86 µm for $n_{eff}$ and C, respectively. The constant term in the fit, C implies a rod with 265 nm diameter cross section, which is in close agreement with the actual width, 300 nm, of the rectangular rods. This indicates that finite width of the particle is not negligible for embedded nanorods and results in red-shifting.

Example 8

Collective Resonances from Embedded Nanostructures in a Nanoantenna Array

Figure 13B:
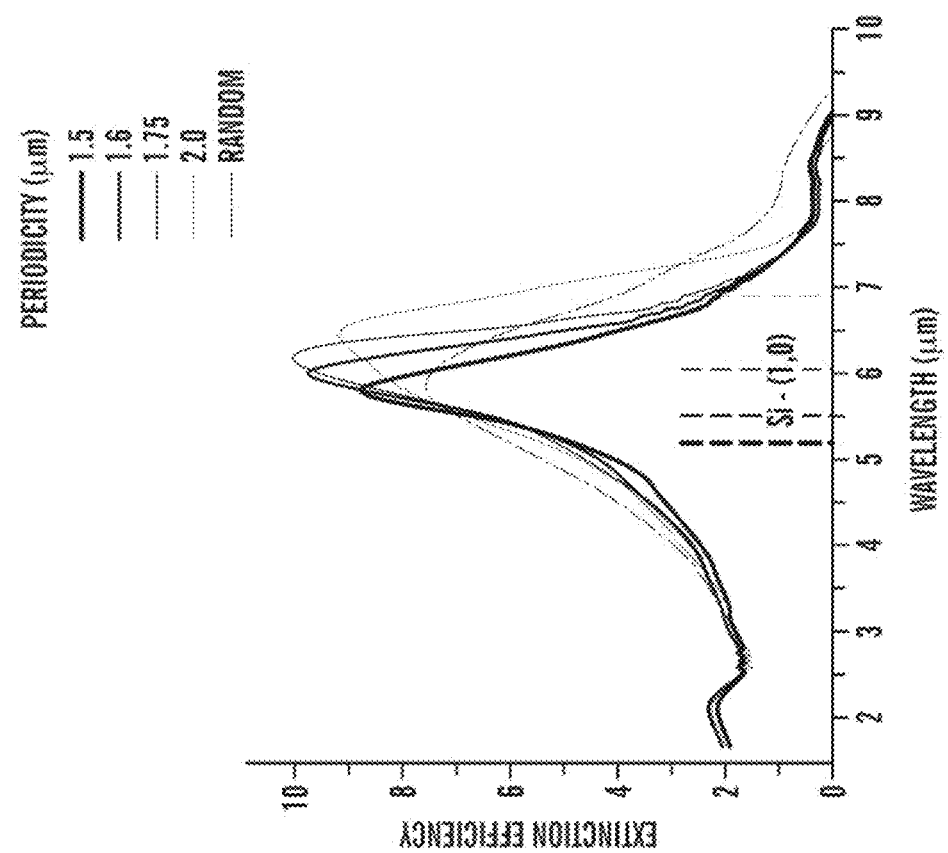
FIG. 13A-13B shows extinction spectra for embedded and on-support nanostructures with changing periodicity.
Figure 13A:
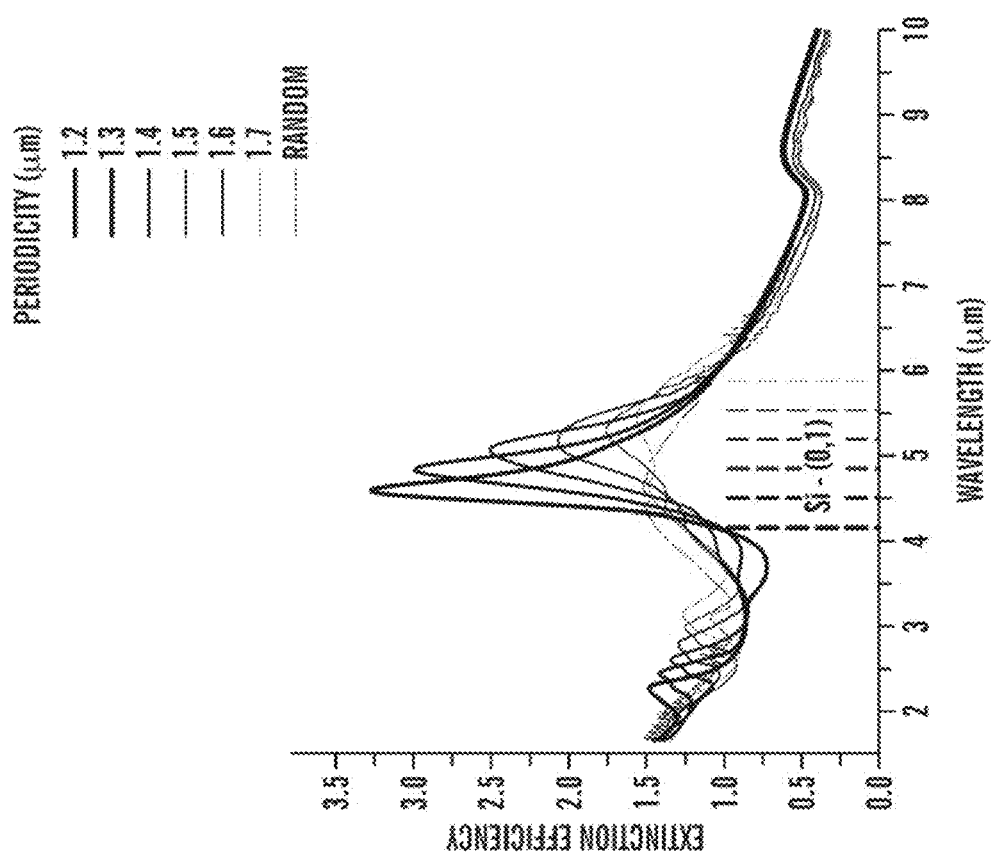

Significantly narrower resonances as well as enhanced extinction efficiencies are demonstrated for well optimized periodic arrays (in square lattice), buried d=200 nm beneath the silicon surface (FIG. 13). The resonance wavelengths/linewidths as well as the extinction efficiencies strongly depend on the array periodicity, a sign for stronger diffractive and plasmonic coupling compared to the on-support arrays. The results here are presented for embedded nanorod particles with L=500 nm and on-support nanorods with L=1100 nm such that the individual particle resonance wavelengths are comparable. In well optimized arrays, a quality factor improvement of $Q_{array}/Q_{ind}$=4.6 over that of an individual nanoparticle is observed due to the suppression of the radiative losses (FIG. 13A)). As shown in FIG. 13B (adapted from Adato et al. Proc. Nat. Acad. Sci. USA 106 19227-19232 (2009)), narrowing of plasmon resonances of on-support arrays is weaker than that of the periodic arrays embedded in a silicon support. Improvements in quality factors for on-support arrays are limited to $Q_{array}/Q_{ind}$=2 due to weaker collective excitation of plasmons. Although this figure may seem to be modest, the fact that near field enhancements are correlated with but not linearly proportional with quality factor improvements must be also taken into consideration (Della Valle et al., Phys. Rev. B 79 113410 (2009), Klar et al., Phys. Rev. Lett. 80 4249-4252 (1998)). In fact, in an earlier article, we have obtained an order of magnitude improved absorption signals for a quality factor improvement of only $Q_{array}/Q_{ind}$=2 leading to signal enhancements of $10^4$-$10^5$ with zepto mole level sensitivities (Adato et al. Proc. Nat. Acad. Sci. USA 106 19227-19232 (2009)). Thus, higher quality factor improvements obtained in this article ($Q_{array}/Q_{ind}$=4.6) could lead to even greater near-field enhancements as we show in the FDTD analysis below. As shown in FIG. 13A), additional resonances at shorter wavelengths are observed for the embedded arrays. These resonances are associated to the diffractive (Wood's) anomalies. They are controlled by the array periodicity and show no variation in their line-widths. The plasmonic excitation modes (both m=1 and m=3) are spectrally far from these shorter wavelength resonances thus plasmons have no effect on these anomalies. Such short wavelength anomalies are absent in the extinction measurements obtained from on-support arrays as a result of diminished diffractive couplings (FIG. 13D).

Figure 14A:
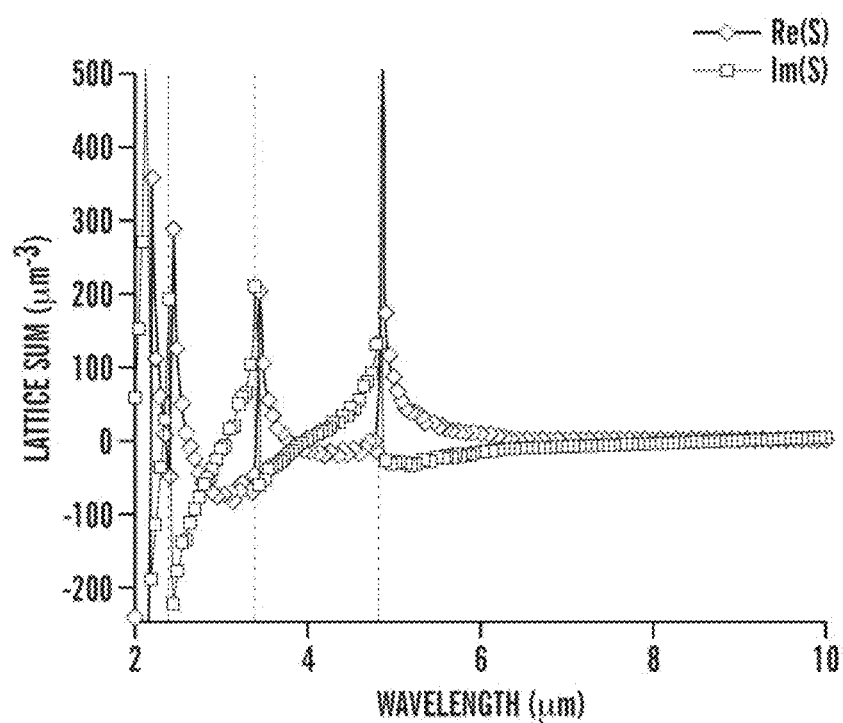
FIGS. 14A-14D shows the strong effect of nanoantenna array periodicity with embedded nanostructures on extinction spectra.
Figure 14B:
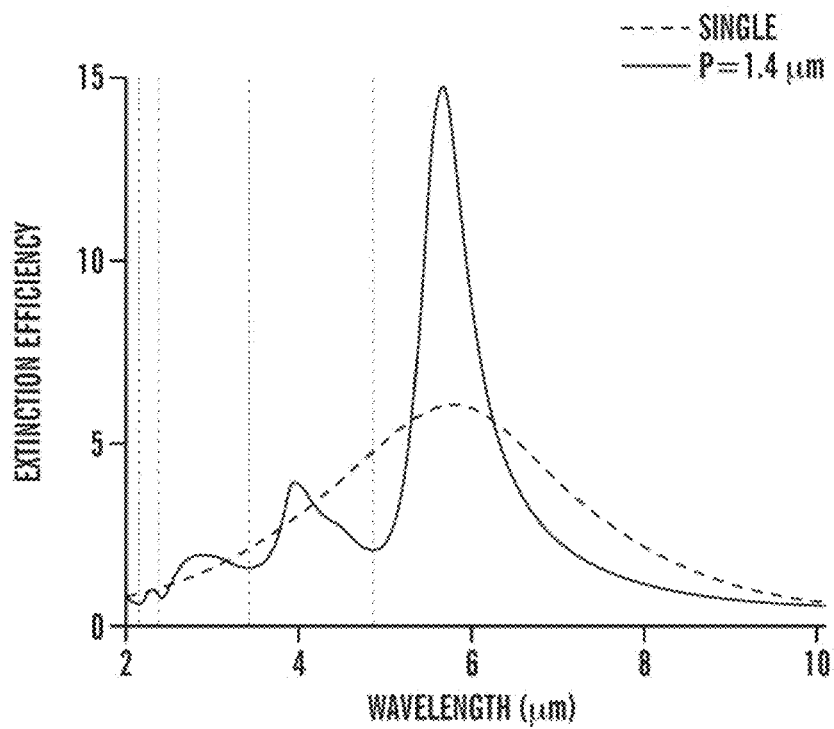
Figure 14C:
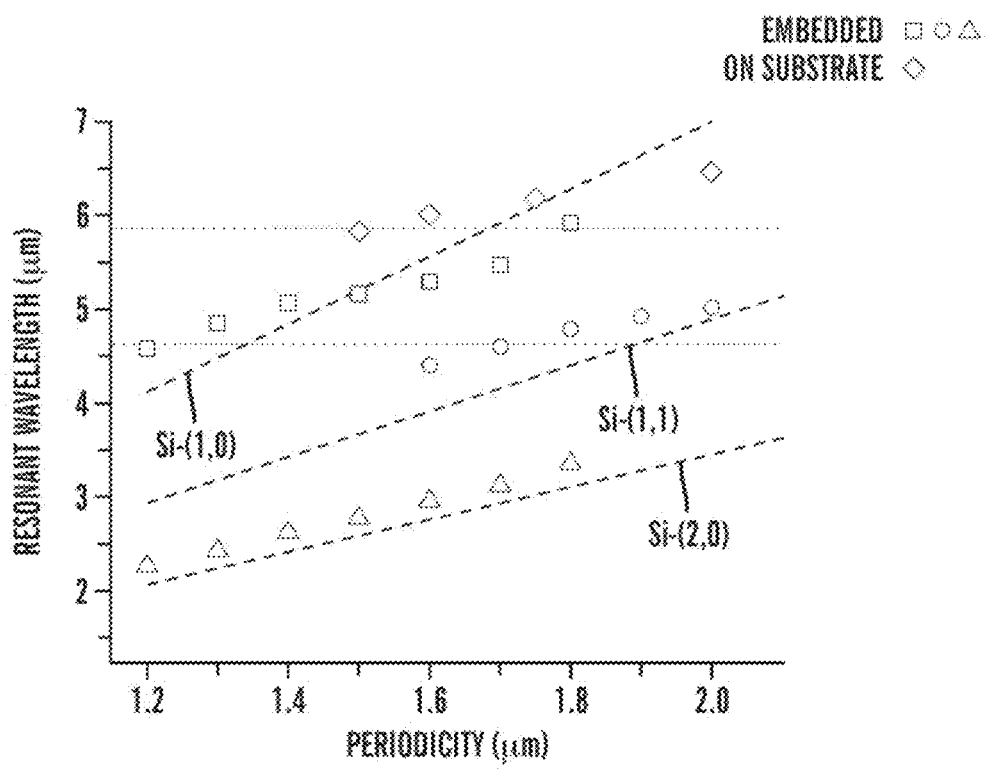

FIG. 14A, 14B presents an analysis of these higher order resonances using CD method for a two-dimensional array consisting of nanorods completely surrounded with silicon medium (L=800 nm). Appearance of the higher grating orders results in a sudden sign change and a sharp maximum in the imaginary and the real parts of the lattice sum S, respectively (FIG. 14A). As shown in FIG. 14B, dips in extinction efficiencies are observed at these grating transition wavelengths $\lambda_{Si/Air-(i,j)} = n_{Si/Air} p/\sqrt{i^2+j^2}$, where p is the array periodicity, $n_{Si/Air}$ is the index of silicon/air, and (i,j) is the two-dimensional grating diffraction order. In FIG. 14C, experimentally obtained resonance wavelengths are plotted for varying array periodicities for embedded (red points) and on-support (blue points) arrays. For embedded nanostructures in the arrays, the spectral locations of the resonances are controlled by the array periodicity and closely follow the analytically derived grating transition wavelengths (dashed lines) corresponding to Si-(0,1), Si-(1,1) and Si-(0,2) grating orders. Slight deviation from the analytical model is likely due to the finite NA (0.4) of the IR-objective resulting in a beam spread.

Figure 10B:
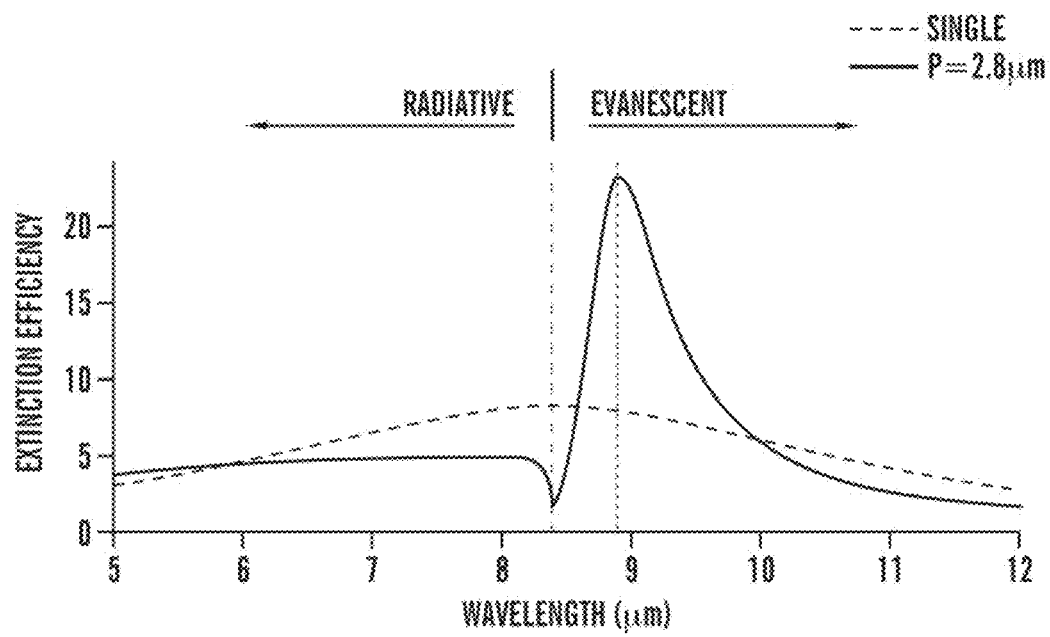
Figure 10C:
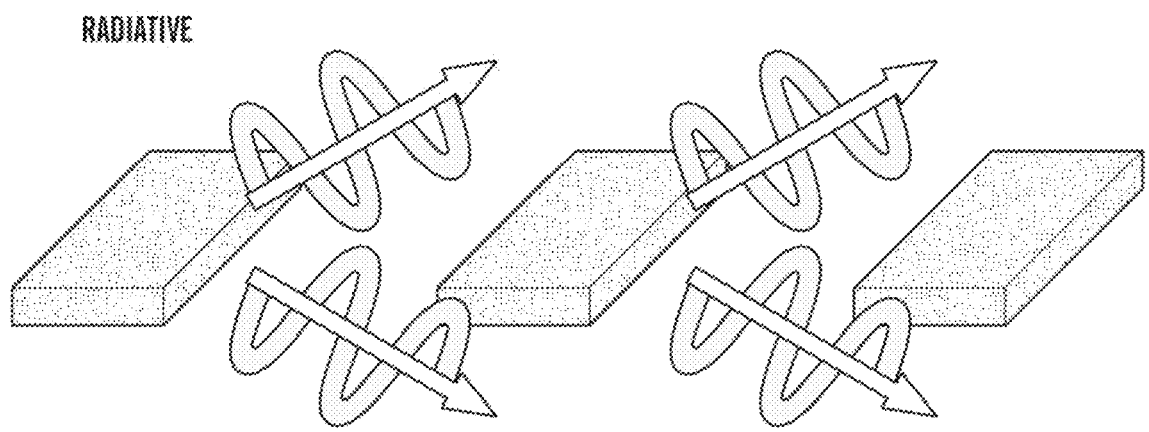
Figure 10D:
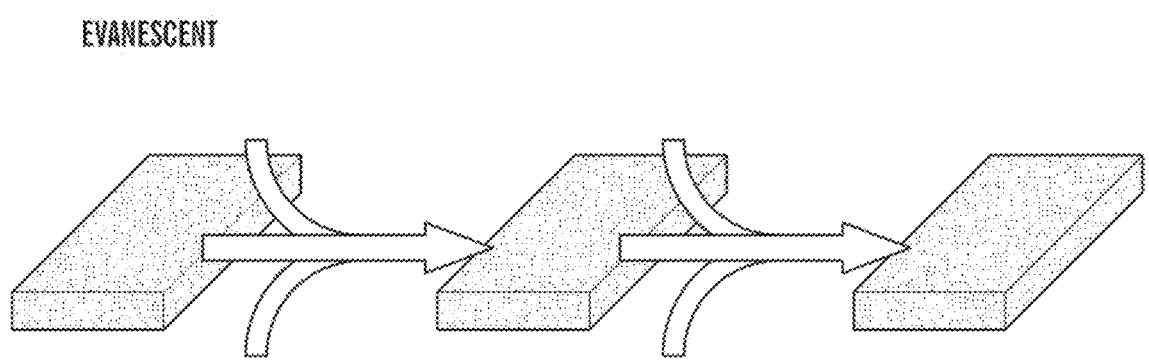
Figure 14D:
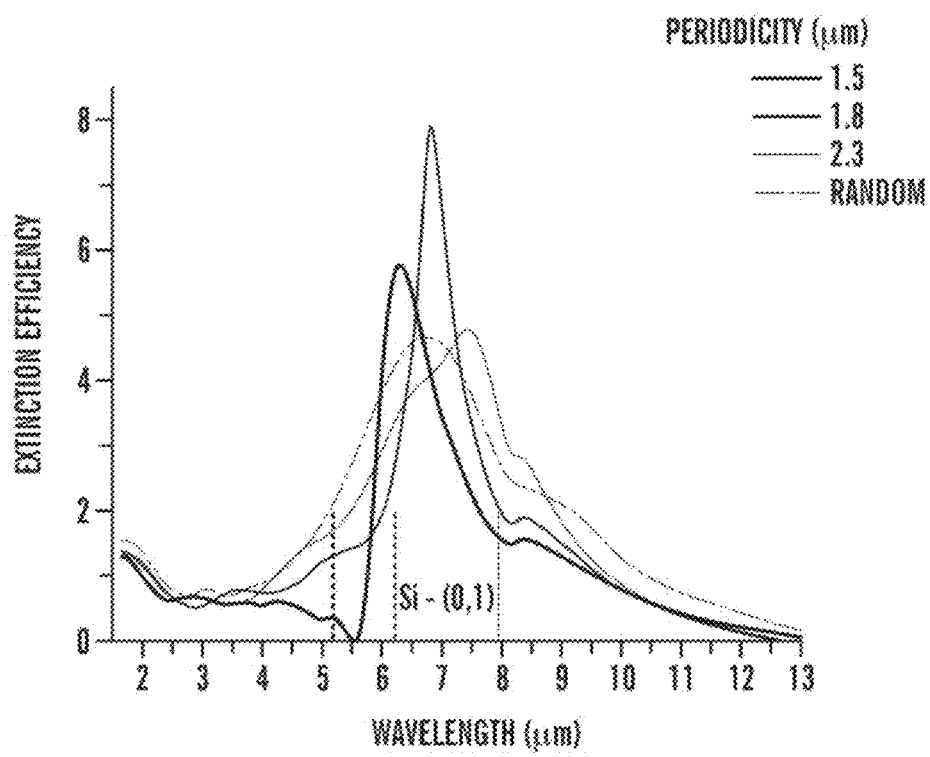
Figure 16B:
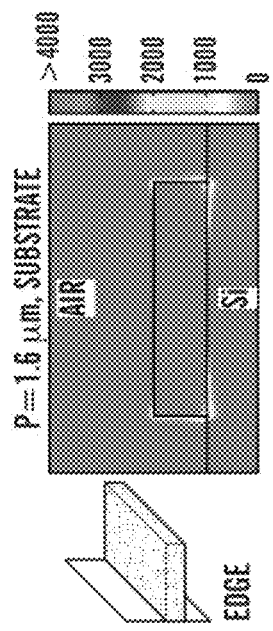
FIGS. 16A-16E show spatial distributions of the near-field intensity enhancements ($|E/E_0|^2$ where $E_0$ is the incident pulse amplitude at the corresponding frequency) for an isolated nanorod particle.
Figure 16C:
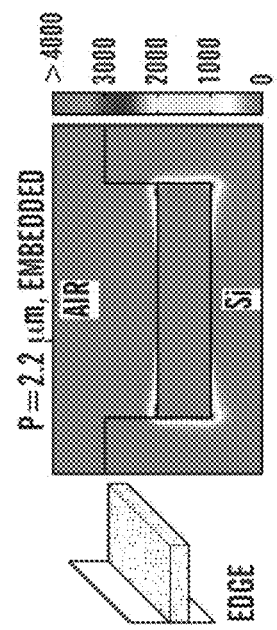
Figure 16A:
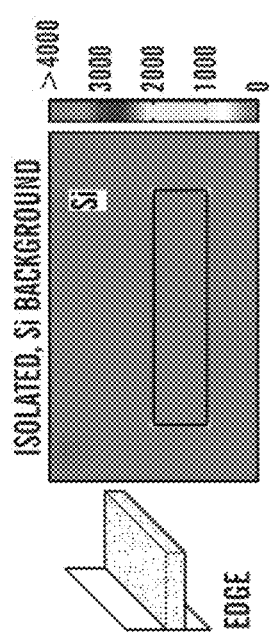
Figure 16E:
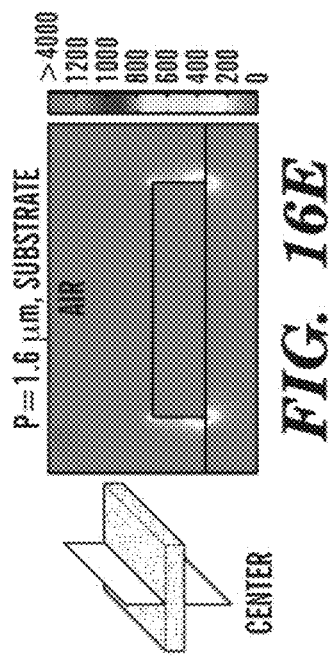
Figure 16D:
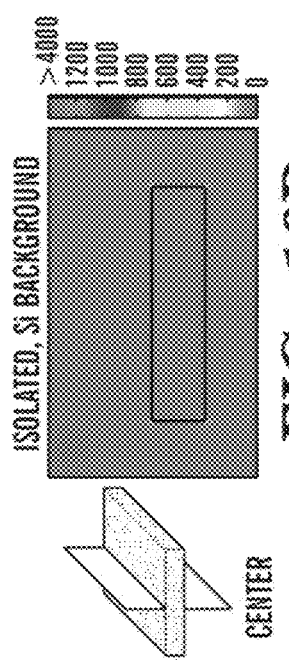
Figure 16F:
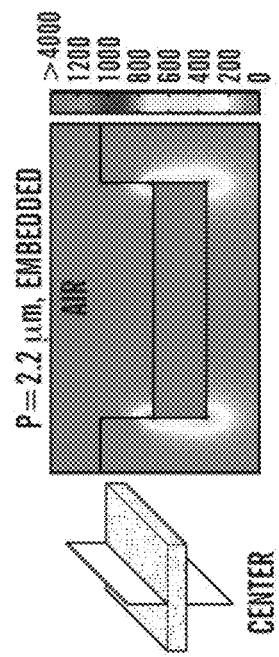
FIG. 16F shows the spatial distribution in the center vertical plane of an isolated nanorod particle in a periodic array embedded in 200 nm beneath the silicon support. Note the different color scales for edge (FIGS. 16A-16C) and center vertical planes (FIGS. 16D-16F) indicated in red in the cartoons to the left.

On the other hand, resonance wavelengths of the on-support arrays do not show significant variation with changing periodicity (blue points) as a result of weaker diffractive coupling among particles. Instead, they slightly deviate from the random on-support array resonance (dotted blue line). FIG. 14D shows extinction spectra obtained from periodic arrays consisting of 800 nm long rods embedded 200 nm beneath the silicon surface. A sharp dip in extinction efficiencies, corresponding to a nearly perfect transmission, is clearly visible in the extinction spectrum for the embedded array with a periodicity of 1.5 μm (red curve in FIG. 14D). This sharp dip, a sign for strong diffractive coupling as shown in FIG. 10B), occurs when the real part of the lattice sum S is a maximum (as discussed herein in Example 5). Such a feature is not observed in extinction spectra obtained from the nanorod arrays directly fabricated on the silicon supports.

Example 9

Enhanced Near-Field Intensities with Collective Plasmonics of a Nanoantenna Array with Embedded Nanostructures Far-field characteristics such as resonance linewidths and extinction efficiencies are a strong indicator of the near field behavior of the plasmonic excitations in relation to the plasmon lifetimes. Due to the suppression of the radiation damping with the confinement of the electromagnetic field within the array (extended plasmon lifetimes), narrowing of the far-field extinction resonances are observed. This narrowing is associated with the enhancement of the near-fields with respect to those of individual nanorods. In particular, when the array's diffractive resonances occur at a wavelength near the plasmon resonance of the individual particle, the collective plasmonic response is most pronounced. Near-field enhancements well beyond than those achievable with a single isolated particle are observed with optimized periodic arrays (Adato et al. Proc. Nat. Acad. Sci. USA 106 19227-19232 (2009)). Considering that embedded nanoparticle arrays have even narrower resonances, much stronger near-field intensities are expected with respect to on-support fabricated arrays. This prediction is confirmed with 3-D FDTD simulations performed for the embedded structures consisting of 800 nm long rods buried 200 nm beneath the silicon surface as well as arrays of same size nanorods fabricated on-silicon support. The particles are modeled as 100 nm thick gold rods without the Ti adhesion layer used in the experiments. The calculated extinction efficiencies (shown in FIG. 15) illustrate the dramatic influence of the array periodicity on the resonance linewidths. The maximum amplitude of the extinction peak varies with the proximity of the array diffractive resonance to the particle LSPR (Auguié et al., Phys. Rev. Lett. 101, 143902 (2008)). The stronger extinctions for the embedded rods (FIG. 15A) with respect that of the on-support ones are associated with the stronger diffractive couplings. The highest quality factors are observed at $\lambda$=7.81 μm (5.68 μm) for the embedded (on-support) arrays for the array with the periodicity of 2.2 μm (1.6 μm). The differences in resonance wavelengths of the embedded and on-support arrays are due to the differences in effective refractive indices. In agreement with our experimental observations (FIG. 13), narrowing of the resonance linewidths is much more pronounced in embedded arrays with respect to on-support ones.

The near-field intensities for individual nanorods in optimized arrays with the narrowest line-widths are shown in FIG. 16. Both embedded and on-support periodic arrays show marked improvements in near field enhancements with respect to the isolated nanorods. However, strongest overall near-field enhancements are observed for embedded structures as a result of longer plasmon lifetimes. For the arrays fabricated on silicon surface, the enhanced near-fields are mainly concentrated in a small region at the base of the nanorod. For the embedded geometry, a peak enhancement of 6,439 is obtained which extends over a large region outside the metal, while the enhancement of the on-support rod geometry is reduced to 3,579 outside the metal with lesser extent. The field distribution of the embedded structure is highly symmetric and closely resembles to that of the particle in homogeneous background. This implies the minimal effect of the air gap on the plasmon resonance. The large field enhancement extends over several tens of nanometers into the support as well as into the air gap.

For biodetection applications, the field enhancement in the air gap would be of primary interest. Despite the fact that the available region for target biomolecules is limited to the air gap region, the embedded geometry still offers advantages over on-support geometry. To quantify the effect, the inventors have computed the integrated near-field intensity over the exposed surface of the embedded and on-support structures within a region extending 5 nm from the metal surface. The integrated intensity for the embedded geometry over this region is at least 2.2 time greater that of the on-support rods. Thus, despite the smaller exposed region, the embedded geometry of the nanostructures is more advantageous due to the larger overall field enhancement. Finally, the large enhancement in the dielectric medium (e.g., a silicon support in this example) could also be extremely attractive for photovoltaic and nonlinear photonic applications.

In summary, it is demonstrated herein that plasmon lifetimes and extinction efficiencies can be controlled by tuning the retarded dipolar couplings among nanoantennas in periodic arrays. Using embedded nanostructures embedded below the surface of a support in a nanoantenna array results in longer plasmon lifetimes and higher extinction efficiencies as compared to on-support, or raised nanostructures on the nanoantenna array. The inventors have analyzed the experimental observations through analytical derivations and also through 3-D FDTD simulations. Herein it is demonstrated that embedded nanostructures in a nanoantenna array results in stronger radiative couplings associated with the more homogeneous dielectric background present in the embedded nanostructure arrays. Through numerical simulations, the correlation between the extended lifetimes of the plasmons and the enhancement of the near field intensities is confirmed. Near-field enhancements well beyond than those achievable with isolated nanoparticles are predicted. The introduced fabrication method and proposed structure could be readily extendable to visible and near-infrared frequencies. Additionally, the nanoantenna arrays as disclosed herein, including nanoantenna arrays with embedded plasmonic nanostructures have inherent flexibility, and can be tailored by one of ordinary skill in the art for use in plasmonic applications utilizing large field enhancements as well as narrower resonances.

REFERENCES

All the references disclosed herein in the specification and the claims are incorporated herein in their entirety by reference.

1. Ozbay, E. *Science* 2006, 311, 189-193.
2. Genet, C.; Ebbesen, T. W. *Nature* 2007, 455, 39-46.
3. Maier, S. Plasmonics: *Fundamentals and Applications* 2007, Springer, N.Y.
4. Barnes, W. L.; Dereux, A.; Ebbesen, T. W. *Nature* 2003, 424, 824-830.
5. Lal S.; Link S.; Halas N. J. *Nature Photonics* 2007, 1, 641-648
6. Yanik, A. A; Wang, X.; Erramilli, S.; Hong, M. K.; Altug, H. *Appl. Phys. Lett.* 2008, 93, 081104.

7. Artar, A.; Yanik A. A.; Altug, H. *Appl Phys Lett.* 2009, 95, 051105.
8. Yanik, A. A.; Huang, M.; Artar, A.; Chang, T. Y.; Altug, H. *Appl. Phys. Lett.* 2010, 96, 021101.
9. Kinkhabwala, A.; Yu, Z.; Fan, S.; Avlasevich, Y.; Mullen, K.; Moerner, W. E. *Nature Photonics,* 2009, 3 654-657.
10. Levene, M. J.; Korlach, J. S.; Turner, W.; Foquet, M.; Craighead, H. G.; Webb, H. G. *Science* 2003, 299, 682-686.
11. Kneipp, K.; Wang, Y.; Kneipp, H. Perelman, L. T.; Itzkan, I; Dasari, R. R.; Feld, M. S. *Phys. Rev. Lett.* 1997, 78, 1667-1670.
12. Nie, S.; Emory, S. R. *Science* 1997, 275, 1102-1106.
13. Lal, S.; Grady, N. K.; Goodrich, G. P.; Halas, N. J *Nano Lett.* 2006, 6, 2338-2343.
14. McFarland, A. D.; Young, M. A.; Dieringer, J. A.; Van Duyne, R. P. *J. Phys. Chem. B* 2005, 109, 11279-11285.
15. Shamsaiea, A.; Heima, J.; Yanik, A. A.; Irudayaraj, J. *Chemical Physics Letters* 2008, 461, 131-135.
16. Kim S.; Jin J.; Kim Y-J.; Park I-Y.; Kim Y; Kim S-W. *Nature* 2008, 453, 757-760.
17. Adato, R.; Yanik, A. A.; Amsden, J. J.; Kaplan, D. L.; Omenetto, F. G.; Hong, M. K.; Erramilli, S.; Altug, H. *PNAS* 2009, 106, 46, 19227-19232
18. Oulton, R. P.; Sorger, V. J.; Zentgraf, T.; Ma, R. M.; Gladden, C.; Dai, L.; Bartal, G.; Zhang, X. *Nature* 2009, 461, 629-632.
19. Noginov, M. A.; Zhu, G.; Belgrave, A. M.; Bakker, R.; Shalaev, V. M.; Narimanov, E. E.; Stout, S.; Herz, E.; Suteewong, T.; Wiesner, U. *Nature* 2009, 460, 1110.
20. Taubner, T.; Korobkin, D.; Urzhumov, Y.; Shvets, G.; Hillenbrand, R. *Science* 2006, 313, 5793, 1595.
21. Fang, N.; Lee, H.; Sun, C.; Zhang, X. *Science* 2005, 308, 5721, 534-537.
22. Smith, D. R.; Pendry, J. B.; Wiltshire, M. C. K. *Science* 2004, 305, 788-792.
23. Shalaev, V. M.; Cai, W.; Chettiar, U. K.; Yuan, H. K.; Sarychev, A. K.; Drachev, V. P.; Kildishev, A. V. *Optics Letters* 2005, 30, 24, 3356.
24. Chen, H. T.; Padilla, W. J.; Cich, M. J.; Azad, A. K.; Averitt, R. D.; Taylor, A. J *Nature Photonics* 2009, 3, 148.
25. MacDonald, K. F.; Sa'mson, Z. L.; Stockman, M. I.; Zheludev, N. I.; *Nature Photonics* 2009, 3, 55.
26. Brewer, G. R. *Electron beam technology in microelectronic fabrication* 1980, Academic Press, Newyork.
27. Melngailis, J. *J. Vac. Sci. Technol. B* 1987, 5, 2, 469-495.
28. Auguié, B.; Barnes, W. L. *Phys. Rev. Lett.* 2008, 101, 143902.
29. Sun, X.; Zhuang, L.; Zhang, W.; Chou, S. Y. *J. Vac. Sci. Technol. B* 1998, 16, 6, 3922-3925.
30. Solak, H. H.; Ekinci, Y. *J. Vac. Sci. Technol. B* 2007, 25, 6, 2123-2126.
31. Henzie, J.; Lee, J.; Lee, M. H.; Hasan, W.; Odom, T. W. *Annual Review of Physical Chemistry* 2009, 60, 147-165.
32. Boltasseva, A. *J. Opt. A: Pure Appl. Opt.* 2009, 11, 114001
33. Aksu, S.; Altug, H. *Mater. Res. Soc. Symp. Proc.* 2010, Vol. 1208E.
34. Haynes C. L.; Van Duyne R P. *J. Phys. Chem. B,* 2001, 105 5599-5611
35. Prikulis, J.; Hanarp, P.; Olofsson, L.; Sutherland, D.; Kall, M. *Nano Lett.* 2004, 4, 1003-1007.
36. Savas, T. A.; Schattenburg, M. L.; Carter, J. M.; Smith, H. I. *J. Vac. Sci. Technol.* 1996, B14, 4167.
37. Burger, G. J.; Smuldersa, E. J. T.; Berenschota, J. W.; Lammerinka, T. S. J.; Fluitmana J. H. J.; Imaib, S. *Sensors and Actuators A: Physical* 1996, 54, 1-3, 669-673.
38. Egger, S.; Hie, A.; Fu, Y.; Chongsathien, J.; Kang, D. J.; Welland, M. E. *Nano Lett.* 2005, 5, 15-20.
39. Gross, L.; Schlittler, R. R.; Meyer, G.; Vanhaverbeke, A.; Allenspach, R. *Appl. Phys. Lett.* 2007, 90, 093121.
40. Vazquez-Mena, O.; Villanueva, G.; Savu, V.; Sidler, K.; van den Boogaart, M. A. F.; Brugger, J. *Nano Lett.* 2008, 8, 11, 3675-3682.
41. Tourovskaia, A.; Barber, T.; Wickes, B. T.; Hirdes, D.; Grin, B.; Castner, D. G.; Healy, K. E.; Folch, A. *Langmuir* 2003, 19, 4754-4764
42. Novotny, L. *Phys. Rev. Lett.* 2007, 98, 266802.
43. Lee, K-S.; El-Sayed, M. A. *J. Phys. Chem. B,* 2006, 110 19220-19225
44. Adato, R.; Yanik, A. A.; Wu, C. H.; Shvets, G.; Altug, H. *Optics Express* 2010, 18, 5, 4526-4537
45. Zou, S.; Schatz, G. C. *Nanotech.* 2006, 17, 2813-2820.
46. Markel, V. A. *J. Phys. B: At. Mol. Opt. Phys.* 2005, 38, 115-121.
47. Lamprecht, B.; Schider, G.; Lechner, R.; Ditlbacher, H.; Krenn, J.; Leitner, A.; Aussenegg, F. *Phys. Rev. Lett.* 2000, 84, 4721.
48. Kravets, V. G.; Schedin, F.; Grigorenko, A. N. *Phys. Rev. Lett.* 2008, 101, 087403.
49. Huang, M.; Yanik, A. A.; Chang, T. Y.; Altug, H. *Optic Express* 2009, 17, 26, 24224-24233.
50. Yablonovitch, E. *Phys Rev Lett.* 1987, 58, 2059-2062.
51. John, S. *Phys Rev Lett.* 1987, 58, 2486-2489.
52. Altug, H.; Englund, D.; Vuckovic, J. *Nature Phys.* 2006, 2, 484-487.
53. Yanik, A. A; Adato R.; Erramilli S.; Altug, H. *Optics Express* 2009, 17, 20900-209 10.
54. Cubukcu, E.; Capasso, F. *Appl. Phys. Lett.* 2009, 95, 201101.
55. Harris, D. C *Materials for infrared windows and domes: properties and performance* 1999, SPIE, Washington.
56. Miller, D. A. B. *Proceedings of the IEEE* 2000, 88, 6.
Alu A, & Engheta N (2008) Tuning the scattering response of optical nanoantennas with nanocircuit loads. *Nature Photonics.* 2:307-310.
Artar A, Yanik A A & Altug H (2009) Fabry-Perot nanocavities in multilayered plasmonic crystals for enhanced biosensing. *Appl. Phys. Lett.* 95:051105
Ataka K, & Heberle J (2007) Biochemical spplications of surface-enhanced infrared absoprtion spectroscopy *Analytical Bioanalytical Chemistry* 308:47-54.
Augie B & Barnes W L (2008) Collective resonaces in gold nanoparticle arrays. *Physical Review Letters* 101:143902.
Bukasov R, & Shumaker-Parry J S (2009) Silver nanocrescents with infrared plasmonic properties as tunable supports for surface enhanced infrared absorption spectroscopy. *Analytical Chemistry* 81:4531-4535
Chen C K, Heinz T F, Ricard D, & Shen Y R (1983) Surface-enhanced second-harmonic generation and Raman scattering. *Physical Review B* 27:1965-1979.
Crozier K B Sundaramurthy A, Kino G S, & Quate C F (2003) Optical antennas: Resonators for local field enhancement. *Journal of Applied Physics* 94:4632-4642.
Datta S (2004) Electrical resistance: An atomistic view. *Nanotech.* 15:S433-S451
Enders D & Pucci A (2006) Surface enhanced infrared absorption of octadecanethiol on wet-chemically prepared Au nanoparticle films. *Applied Physics Letters* 88:184104
Frey H G, Witt S, Felderer K, & Guckenberger R (2004) High-resolution imiaging of single fluorescent molecules with the optical near-field of a metal tip. *Physical Review Letters* 93:200801

Genet C, & Ebbesen T W (2007) Light in tiny holes. *Nature* 455:39-46.

Jensen T R, Van Duyne R P, Johnson S A & Maroni V A (2000) Surface-enhanced infrared spectroscopy: a comparison of metal island films with discrete and non-discrete surface plasmons. *Applied Spectroscopy* 54:371-377.

Kneipp K, Wang Y, Kneipp H, Perelman L T, Itzkan I, Dasari R R, Feld M S (1997) Single molecule detection using Surface-Enhanced Raman Scattering (SERS). *Physical Review Letters* 78:1667-1670.

Kundu J, Le F, Norlander P, & Halas N J (2008) Surface enhanced infrared absorption (SEIRA) spectroscopy on nanoshell aggregate supports. *Chemical Physics Letters.* 452:115-119

Lal S, Link S, & Halas N J (2007) Nano-optics from sensing to waveguiding. *Nature Photonics* 1:641-648.

Lamprecht B, Schider G, Lechner R T, Ditlbacher H, Krenn J R, Leitnre A & Aussenegg F R (2000) Metal nanoparticle gratings: influence of dipolar interaction on the plasmon resonances. *Physical Review Letters* 84:4721-4724.

Lawrence B D, Omentetto F G, Chi K & Kaplan D L (2008) Processing methods to control silk fibroin film biomaterial features. *J. Mater. Sci.* 43:6967-6985.

Meier M, Wokaun A & Liao P F (1985) Enhanced fields on rough surfaces: dipolar interactions among particles of sizes exceeding the Rayleigh limit. *Journal of the Optical Society of America B* 2:931-949

Neubrech F, Pucci A, Cornelius T W, Karim S, Garcia-Extarri A & Aizpurua J (2008) Resonant plasmonic and vibrational coupling in a tailored nanoantenna for infrared detection. *Physical Review Letters* 101:157403.

Omenetto F G, & Kaplan D L (2008) A new route for silk. *Nature Photonics.* 2:641-643.

Osawa M, Ikeda M (1991) Surface-enhanced infrared absorption of p-Nitrobenzoic acid deposited on silver island films: contributions of electromagnetic and chemical mechanisms. *Journal of Physical Chemistry.* 95:9914-9919

Sashina E S, Bocheck A M, Novoselov N P, & Kirichenko D A (2006) *Russion Journal of Applied Chemistry* 79:869-876.

Schnell M, Garcia-Etxarri A, Huber A J, Crozier K, Aizpurua J, & Hillenbrand R (2009) Controlling the near-field oscillations of loaded plasmonic nanoantennas. *Nature Photonics.* 3:287-291

Tolstoy V P, Chemyshova I V, Skyrshevsky V A (2003) in Handbook of Infrared Spectroscopy of Ultrathin Films (John Wiley & Sons Inc, Hoboken, N.J.), pp. 243-286.

Warwicker J O (1954) The crystal structure of silk fobroin. *Acta Crystal* 7:565-571.

Williams S M, Stafford A D, Rodriguez K R, Rogers T M & Coe J V (2003) Accessing surface plasmons with Ni microarrays for enhanced IR absorption by monolayers. *J. Phys. Chem. B* 107:11871-11879.

Yanik A A, Klimeck G, and Datta S (2007) Quantum transport with spin dephasing: A Nonequilibrium Green's Function approach. *Phys. Rev. B* 76:045213.

Yanik A A, Wang X, Erramilli S, Hong M K, & Altug H (2008) Extraordinary midinfrared transmission of rectangular coaxial nanoaperture arrays. *Appl. Phys. Lett.* 93:081104.

Zou S, Janel N, & Schatz G C (2004) Silver nanoparticle array structures that produce remarkably narrow plasmon lineshapes. *Journal of Chemical Physics* 120:10871-10875.

Zou S, Schatz G C, (2005) Silver nanoparticle array structures that produce giant enhancements in electromagnetic field. *Chemical Physical Letters* 403:62-67.

E. Ozbay, "Plasmonics: Merging photonics and electronics at nanoscale dimensions," Science 311, 189-193 (2006).

S. Lal, S. Link, and N. J. Halas, "Nano-optics from sensing to waveguiding," Nature Photon. 1, 641-648 (2007).

M. I. Stockman, V. M. Shalaev, M. Moskovits, R. Botet, T. F. George, "Enhanced Raman scattering by fractal clusters: Scale invariant theory," Phys. Rev. B 46 2821 (1992).

K. Kneipp, Y. Wang, H. Kneipp, L. T. Perelman, I. Itzkan, R. R. Dasari, and M. S. Feld, "Single molecule detection using surface-enhanced Raman scattering (SERS)," Phys. Rev. Lett. 78, 1667-1670 (1997).

R. Adato et al. "Ultra-sensitive vibrational spectroscopy of protein monolayers with plasmonic nanoantenna arrays," Proc. Nat. Acad. Sci. USA 106 19227-19232 (2009).

F. Neubrech, A. Pucci, T. W. Cornelius, S. Karim, A. Garcia-Extarri, and J. Aizpurua, "Resonant plasmonic and vibrational coupling in a tailored nanoantenna for infrared detection," Phys. Rev. Lett. 101, 157403 (2008).

E. J. Sanchez, L. Novotny, and X. S. Xie, "Near-field fluorescence microscopy based on two-photon excitation with metal tips," Phys. Rev. Lett. 82, 4014-4017 (1999).

V. E. Ferry, L. A. Sweatlock, D. Pacifici, and H. A. Atwater, "Plasmonic nanostructure design for efficient light coupling into solar cells," Nano Lett. 8, 4391-4397 (2008).

A Artar, A. A. Yanik and H. Altug, "Fabry-Perot nanocavities in multilayered plasmonic crystals for enhanced biosensing," Appl. Phys. Lett. 95 051105 (2009).

A. A. Yanik, R. Adato, S. Erramilli and H. Altug, "Hybridized nanocavities as single-polarized plasmonic antennas," Opt. Express 17 20900 (2009).

J. Homola, S. S. Yee, and G. Gauglitz, "Surface plasmon resonance sensors: review," Sens. Actuators B 54, 3-15 (1999)

I. M. White and X. Fan, "On the performance quantification of resonant refractive index sensors," Opt. Express 16, 1020-1028 (2008).

K-S. Lee and M. A. El-Sayed, "Gold and silver nanoparticles in sensing and imaging: sensitivity of plasmon response to size, shape and metal composition," J. Phys. Chem. B 110 19220 (2006).

F. Wang and Y. R. Shen, "General propeties of local plasmons in metal nanostructures," Phys. Rev. Lett. 97 (2006).

C. Sönnichsen, T. Franzl, T. Wilk, G. Von Plessen, and J. Feldmann, "Drastic resuction of plasmon damping in gold nanorods," Phys. Rev. Lett. 88 077402 (2002).

S. Zou and G. C. Schatz, "Theoretical studies of plasmon resonances in one dimensional nanoparticles chains: narrow lineshapes with tunable widths," Nanotech. 17, 2813-2820 (2006).

G. Della Valle, T. Sondergaard, and S. I. Bozhevolnyi, "Efficient suppression of radiation damping in resonant retardation-based plasmonic structures," Phys. Rev. B 79 113410 (2009).

V. A. Markel, "Divergence of dipole sums and the nature of non-Lorentzian exponentially narrow resonances in one-dimensional periodic arrays of nanospheres," J. Phys. B: At. Mol. Opt. Phys. 38, L115-L121 (2005).

B. Lamprecht et al., "Metal nanoparticle gratings: influence of dipolar particle interaction on the plasmon resonance," Phys. Rev. Lett., 84 (2000).

B. Auguié and W. L. Barnes, "Collective resonances in gold nanoparticle arrays," Phys. Rev. Lett. 101, 143902 (2008).

V. G. Kravets, F. Schedin, and A. N. Grigorenko, "Extremely Narrow Resonances based on Diffraction Coupling of Localized Plasmons in Arrays of Metallic nanoparticles," Phys. Rev. Lett. 101 087403 (2008).

Y. A. Urzhumov and G. Shvets, "Applications of nanoparticle arrays to coherent anti-Stokes Raman spectroscopy of chiral molecules," Proc. SPIE, 5927 59271D (2005).

CST Microwave Studio, Computer Simulation Technology, Darmstadt, Germany, http://www.cst.com.

The electric field due to point dipole are given by $A_{ij} \cdot p_j = k^2 \exp(ikr_{ij})\{(r_{ij} \times p_j) \times r_{ij}/r_{ij}^3 + (1-ikr_{ij})[3r_{ij}(r_{ij} \cdot p_j) - r_{ij}^2 p_j]/r_{ij}^5\}$. The first term in the brackets has 1/r dependence and corresponds to the far-field radiation. The second terms are relevant for short range interactions. In order to emphasize the importance of the phase term in the collective scattering process the interaction term is written as $\exp(ikr_{ij})C_{ij} \cdot p_j = A_{ij} \cdot p_j$ in the text.

A. D. Rakic, A. B. Djurisic, J. M. Elazar, and M. L. Majewski, "Optical properties of metallic films for vertical-cavity optoelectronic devices," Appl. Opt. 37, 5271-5283 (1998).

E. D. Palik, ed. *Handbook of Optical Constants of Solids II* (Academic, Orlando, Fla., 1985).

M. Meier and A. Wokaun, "Enhanced fields on large metal particles: dynamic depolarization," Opt. Lett. 8 581-583 (1983).

T. Jensen, L. Kelly, A. Lazarides and G. C. Schatz, "Electrodynamics of noble metal nanoparticles and nanoparticle clusters," J. Clust. Sci. 10 (1999).

L. Rayleigh, "On the dynamical theory of gratings," Proc. Royal Soc. London A, 79 399-416 (1907).

X. M. Bendaña and F. J. Garcia de Abajo, "Confined collective excitations of self-standing and supported planar periodic particle arrays," Opt. Express 17 18826-18835 (2009).

K. B. Crozier, A. Sundaramurthy, G. S. Kino, and C. F. Quate, "Optical antennas: resonators for local field enhancement," J. Appl. Phys. 94, 4632-4642 (2003).

E. Cubukcu and F. Capasso, "Optical nanorod antennas as dispersive one-dimensional Fabry-Perot resonators for surface plasmons," Appl. Phys. Lett. 95, 201101 (2009).

L. Novotny, "Effective wavelength scaling for optical antennas," Phys. Rev. Lett. 98, 266802 (2007).

A. A. Yanik, X. Wang, S. Erramilli, M. K. Hong, and H. Altug, "Extraordinary midinfrared transmission of rectangular coaxial nanoaperture arrays," Appl. Phys. Lett. 93, 081104 (2008).

R. Adato et al., "Ultra-sensitive vibrational spectroscopy of protein monolayers with plasmonic nanoantenna arrays—Supporting information," http://www.pnas.org/content/106/46/19227/suppl/DCSupplemental B. Auguié and W. L. Barnes, "Diffractive coupling in gold nanoparticle arrays and the effect of disorder," Opt. Lett. 34 401-403 (2009).

T. Klar et al., "Surface-plasmon resonances in single metallic nanoparticles," Phys. Rev. Lett. 80 4249-4252 (1998).

The invention claimed is:

1. A nanoantenna array device comprising;
   a. a flexible support selected from a thin film support, a sticky support or elastic support, wherein the flexible support can conform to be fitted inside a predefined shape, void or recess, or wrapped on the outside of an element;
   b. a plurality of plasmonic nanostructures on the flexible support, the plasmonic nanostructures
      (i) having predefined three-dimensional-shapes, each plasmonic nanostructure having a substantially consistent shape of an upper surface and a surface contacting the flexible support, where the upper surface is consistently flat and the side walls are perpendicular to the surface of the flexible support and have a vertical wall profile for localized plasmon resonance; and
      (ii) arranged in a predefined periodic pattern with respect to the flexible support for diffracting an incident electromagnetic radiation, wherein the incident electromagnetic radiation forms a diffraction order that is evanescent where the wavelength of the incident electromagnetic radiation is longer than the predefined pattern's periodicity, and wherein the incident electromagnetic radiation forms a diffraction order that is radiative where the wavelength of the incident electromagnetic radiation is shorter than the predefined pattern's periodicity; and
      (iii) separated by a periodicity of between $\lambda/2$-$2\lambda$ or $\lambda/4$-$5\lambda$, wherein $\lambda$ refers to the wavelength of an electromagnetic radiation; and
      (iv) each plasmonic nanostructure having a consistent height of between 10-200 nm, and a consistent surface geometry.

2. The nanoantenna array of claim 1, wherein the plurality of plasmonic nanostructures are
   (i) raised on the surface of the flexible support, and/or
   (ii) depressed below the surface of the flexible support.

3. The nanoantenna array of claim 2, wherein the plurality of plasmonic nanostructures depressed below the surface of the flexible support are layered with a material that is non-wavelength penetrating or can be penetrated by an incident wavelength of electromagnetic radiation.

4. The nanoantenna array of claim 2, wherein the nanostructures on the surface of the support have minimal or no particle scattering within 20 nm of each of the plasmonic nanostructures.

5. The nanoantenna array of claim 2, wherein the predefined pattern of nanostructures comprises plasmonic nanostructures of three-dimensional different shapes.

6. The nanoantenna array of claim 1, wherein the predefined pattern of nanostructures is selected from the group consisting of: a periodic pattern, a non-periodic pattern, a uniform pattern, a lattice, a non-random pattern, and a super-periodic pattern.

7. The nanoantenna array of claim 1, wherein the flexible support is a non-conductive layer.

8. The nanoantenna array of claim 1, wherein the predefined three-dimensional shapes of the plasmonic nanostructures are shapes selected from the group consisting of: nanorod, nanorectangle, nanosquare, nanodisc, nanocircle, nano-oval, nanotriangle, cross-shaped, nanowires, or irregular shaped.

9. The nanoantenna array of claim 1, wherein the plasmonic nanostructures are separated by a periodicity of between 100-10,000 nm.

10. The nanoantenna array of claim 1, further comprising an adhesive layer, wherein the adhesive layer is between the flexible support and the plurality of plasmonic nanostructures.

11. The nanoantenna array of claim 1, wherein the plasmonic nanostructures comprise at least one plasmonic material or a nonplasmonic material.

12. The nanoantenna array of claim 1, wherein the plasmonic nanostructures are coupled to one or more other plasmonic nanostructures.

13. The nanoantenna array of claim 1, wherein the plasmonic nanostructures comprise a plurality of layers of two or more different plasmonic materials.

14. The nanoantenna array of claim 1, wherein the plasmonic nanostructures are arranged in a predefined pattern as a function of their localized plasmon resonance.

15. The nanoantenna array of claim 1, wherein the flexible support has a substantially planar surface.

16. The nanoantenna array of claim 1, wherein the nanostructure has a consistent height of between 10-120 nm.

17. The nanoantenna array of claim 1, wherein thin film support is selected from; parylene C film or PDMS or LDPE.

18. The nanoantenna array of claim 1, wherein the combination of the shape of the nanostructures and the predefined pattern of the nanostructures results in near-field enhancements.

19. The nanoantenna array of claim 1, wherein the combination of the shape of the nanostructures and the predefined pattern of the nanostructures results in absorption enhancement, where absorption is controlled by the localized plasmon resonance.

20. The nanoantenna array of claim 1, wherein the flexible support can be stretched to actively tune the periodicity of the nanostructures.

21. The nanoantenna array of claim 20, wherein the flexible support can be stretched to alter the periodicity of the nanostructures in the x-axis, or the y-axis or the x- and y-axis.

22. The nanoantenna array of claim 1, wherein the flexible support can be stretched to change the shape of the nanostructures.

23. The nanoantenna array of claim 1, wherein the flexible support can be stretched to between 1%-20% of its original size.

24. The nanoantenna array of claim 1, wherein the consistent height is between 70 nm and 160 nm.

25. The nanoantenna array of claim 24, wherein the consistent height is approximately 150 nm.

26. The nanoantenna array of claim 24, wherein the consistent height is approximately 100 nm.

27. At least two nanoantenna array devices, each nanoantenna array device comprising;
a. a flexible support selected from a thin film support, a sticky support or elastic support, wherein the flexible support can conform to be fitted inside a predefined shape, void or recess, or wrapped on the outside of an element;
b. a plurality of plasmonic nanostructures on the flexible support, the plasmonic nanostructures
(i) having predefined three-dimensional-shapes, each plasmonic nanostructure having a substantially consistent shape of an upper surface and a surface contacting the flexible support, wherein the upper surface is consistently flat and the side walls are perpendicular to the surface of the flexible support and have a vertical wall profile for localized plasmon resonance; and
(ii) arranged in a predefined periodic pattern with respect to the flexible support for diffracting an incident electromagnetic radiation, wherein the incident electromagnetic radiation forms a diffraction order that is evanescent where the wavelength of the incident electromagnetic radiation is longer than the predefined pattern's periodicity, and wherein the incident electromagnetic radiation forms a diffraction order that is radiative where the wavelength of the incident electromagnetic radiation is shorter than the predefined pattern's periodicity; and
(iii) separated by a periodicity of between $\lambda/2$-$2\lambda$ or $\lambda/4$-$5\lambda$, wherein $\lambda$ refers to the wavelength of an electromagnetic radiation; and
(iv) each plasmonic nanostructure having a consistent height of between 10-200 nm, and a consistent surface geometry,
wherein each nanoantenna device is substantially identical.

* * * * *